US008696749B2

United States Patent
Lyons et al.

(10) Patent No.: US 8,696,749 B2
(45) Date of Patent: *Apr. 15, 2014

(54) ARTIFICIAL INTERVERTEBRAL DISC

(75) Inventors: Matthew Lyons, Franklin Lakes, NJ (US); Stephen M. Green, Syracuse, NY (US); Matthew A. Keary, Etna, NY (US)

(73) Assignee: Blackstone Medical, Inc., Lewisville, TX (US)

( * ) Notice: Subject to any disclaimer, the term of this patent is extended or adjusted under 35 U.S.C. 154(b) by 2103 days.

This patent is subject to a terminal disclaimer.

(21) Appl. No.: 10/891,635

(22) Filed: Jul. 15, 2004

(65) Prior Publication Data

US 2004/0267369 A1    Dec. 30, 2004

Related U.S. Application Data

(63) Continuation-in-part of application No. 10/423,414, filed on Apr. 25, 2003, now Pat. No. 6,960,232.

(60) Provisional application No. 60/375,842, filed on Apr. 25, 2002.

(51) Int. Cl.
    *A61F 2/44*   (2006.01)
(52) U.S. Cl.
    USPC .................. 623/17.16; 623/17.15; 623/17.12
(58) Field of Classification Search
    USPC ........................................ 623/17.11–17.16
    See application file for complete search history.

(56) References Cited

U.S. PATENT DOCUMENTS

| | | | |
|---|---|---|---|
| 3,953,566 A | | 4/1976 | Gore |
| 4,309,777 A | | 1/1982 | Patil |
| 4,349,921 A | | 9/1982 | Kuntz |
| 4,554,914 A | | 11/1985 | Kapp et al. |
| 4,759,769 A | | 7/1988 | Hedman et al. |
| 4,911,718 A | | 3/1990 | Lee et al. |
| 4,932,975 A | | 6/1990 | Main et al. |
| 4,997,432 A | | 3/1991 | Keller |
| 5,002,576 A | * | 3/1991 | Fuhrmann et al. ......... 623/17.15 |
| 5,071,437 A | | 12/1991 | Steffee |
| 5,123,926 A | | 6/1992 | Pisharodi |
| 5,171,281 A | | 12/1992 | Parsons et al. |
| 5,236,460 A | | 8/1993 | Baber |
| 5,258,031 A | | 11/1993 | Salib et al. |
| 5,306,310 A | | 4/1994 | Siebels |

(Continued)

FOREIGN PATENT DOCUMENTS

| | | |
|---|---|---|
| EP | 0 538 183 | 4/1993 |
| EP | 0 610 837 A1 | 8/1994 |

(Continued)

OTHER PUBLICATIONS

International Search Report of PCT/US2003/12872 (1 page).

(Continued)

*Primary Examiner* — David Isabella
*Assistant Examiner* — Dinah Baria
(74) *Attorney, Agent, or Firm* — Baker & McKenzie LLP

(57) ABSTRACT

The present invention is directed to the field of prosthetic devices. More particularly, one embodiment of the present invention is directed to an artificial disc that can be used as a replacement for an intervertebral disc (e.g., a human intervertebral lumbar disc, a human intervertebral cervical disc and/or a human intervertebral thoracic disc).

62 Claims, 47 Drawing Sheets

(56) References Cited

U.S. PATENT DOCUMENTS

| | | |
|---|---|---|
| 5,314,477 A | 5/1994 | Marnay |
| 5,320,644 A | 6/1994 | Baumgartner |
| 5,370,697 A | 12/1994 | Bungartner |
| 5,401,269 A | 3/1995 | Buttner-Janz et al. |
| 5,480,447 A | 1/1996 | Skiba |
| 5,507,816 A | 4/1996 | Bullivant |
| 5,507,823 A | 4/1996 | Walston et al. |
| 5,534,030 A | 7/1996 | Navvarro et al. |
| 5,545,229 A | 8/1996 | Parsons et al. |
| 5,549,679 A | 8/1996 | Kuslich |
| 5,674,294 A | 10/1997 | Bainville et al. |
| 5,674,296 A | 10/1997 | Bryan et al. |
| 5,676,701 A | 10/1997 | Yuan et al. |
| 5,683,465 A | 11/1997 | Shinn et al. |
| 5,702,449 A | 12/1997 | McKay |
| 5,702,450 A | 12/1997 | Bisserie |
| 5,865,846 A * | 2/1999 | Bryan et al. ............... 128/898 |
| 5,899,941 A | 5/1999 | Nishijima et al. |
| 6,001,130 A | 12/1999 | Bryan et al. |
| 6,063,121 A * | 5/2000 | Xavier et al. .............. 623/17.15 |
| 6,156,067 A | 12/2000 | Bryan et al. |
| 6,264,695 B1 | 7/2001 | Stoy |
| 6,419,706 B1 | 7/2002 | Graf |
| 6,425,919 B1 | 7/2002 | Lambrecht |
| 6,482,235 B1 | 11/2002 | Lambrecht |
| 6,582,466 B1 | 6/2003 | Gauchet |
| 6,582,468 B1 | 6/2003 | Gauchet |
| 6,626,943 B2 | 9/2003 | Eberlein et al. |
| 6,692,495 B1 | 2/2004 | Zacouto |
| 6,743,511 B2 | 6/2004 | Dittrich et al. |
| 6,749,635 B1 | 6/2004 | Bryan |
| 6,960,232 B2 | 11/2005 | Lyons et al. |
| 6,966,931 B2 * | 11/2005 | Huang ....................... 623/17.16 |
| 7,066,960 B1 * | 6/2006 | Dickman ................... 623/17.16 |
| 7,074,240 B2 * | 7/2006 | Pisharodi .................. 623/17.15 |
| 7,291,171 B2 * | 11/2007 | Ferree ....................... 623/17.11 |
| 7,517,363 B2 * | 4/2009 | Rogers et al. ............. 623/17.11 |
| 2002/0035400 A1 | 3/2002 | Bryan et al. |
| 2002/0128715 A1 | 9/2002 | Bryan et al. |
| 2002/0151979 A1 | 10/2002 | Lambrecht |
| 2002/0189622 A1 | 12/2002 | Cauthen, III et al. |
| 2003/0135277 A1 | 7/2003 | Bryan et al. |
| 2003/0199982 A1 | 10/2003 | Bryan |
| 2004/0054411 A1 | 3/2004 | Kelly et al. |
| 2004/0098131 A1 | 5/2004 | Bryan et al. |
| 2005/0131544 A1 * | 6/2005 | Kuras et al. .............. 623/17.13 |
| 2008/0015698 A1 * | 1/2008 | Marino et al. ............ 623/17.15 |
| 2008/0133013 A1 * | 6/2008 | Duggal et al. ............ 623/17.16 |

FOREIGN PATENT DOCUMENTS

| | | |
|---|---|---|
| FR | 2 787 014 | 6/2000 |
| FR | 2 787 015 | 6/2000 |
| WO | WO 91/13598 | 9/1991 |
| WO | WO 94/04100 | 3/1994 |
| WO | WO 99/62439 | 12/1999 |
| WO | WO 00/13619 | 3/2000 |
| WO | WO 01/12107 | 2/2001 |
| WO | WO 01/28464 | 4/2001 |

OTHER PUBLICATIONS

Supplementary European Search Report of EP 03 72 6462 (3 pages).
English Language Abstract of FR 2 787 014.
English Language Abstract of FR 2 787 015.
English Language Abstract of EP 0 538 183.
English Language Abstract of WO 94/04100.
English Language Abstract of WO 91/13598.
English Language Abstract EP 0 610 837 A1.

* cited by examiner

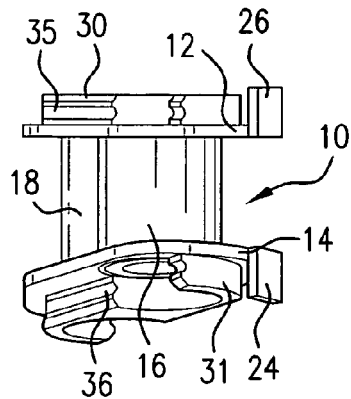
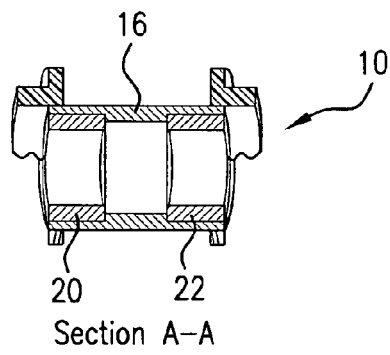
FIG.2A   FIG.2B
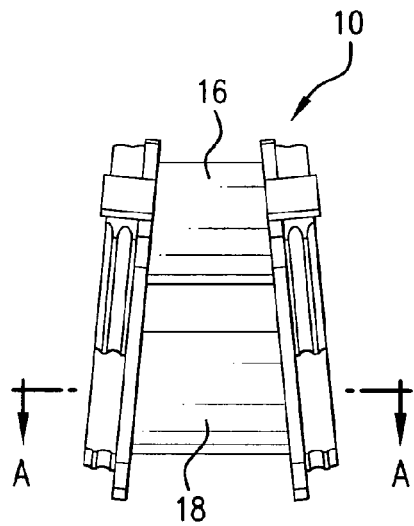
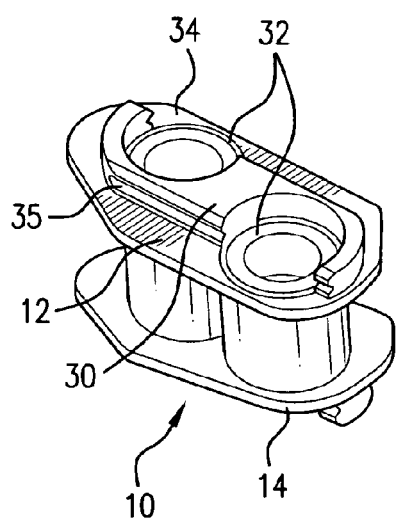
FIG.2C   FIG.2D
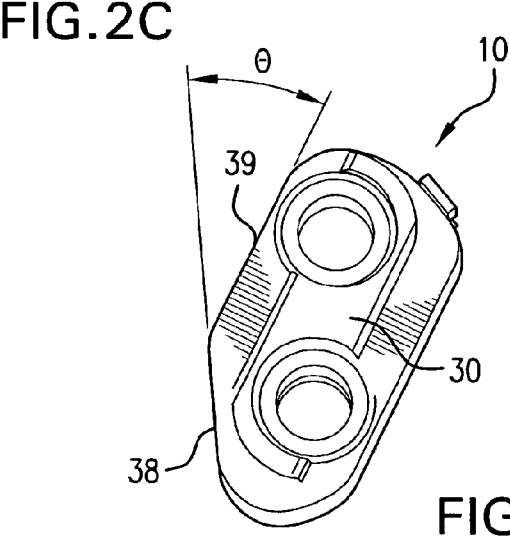
FIG.2E

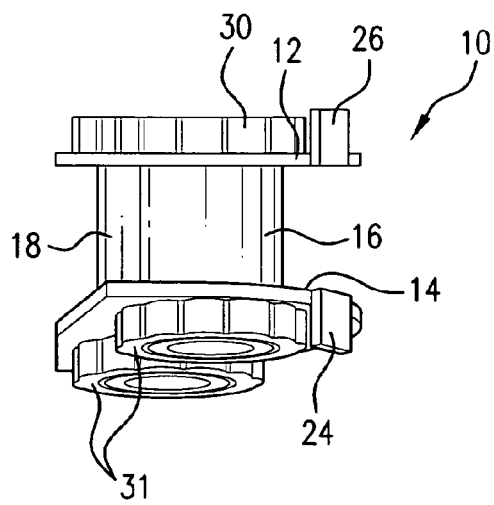
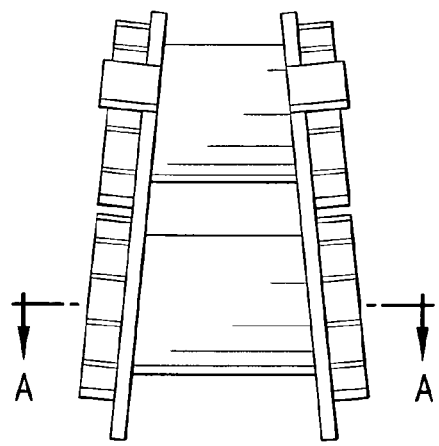
FIG.3A  FIG.3B
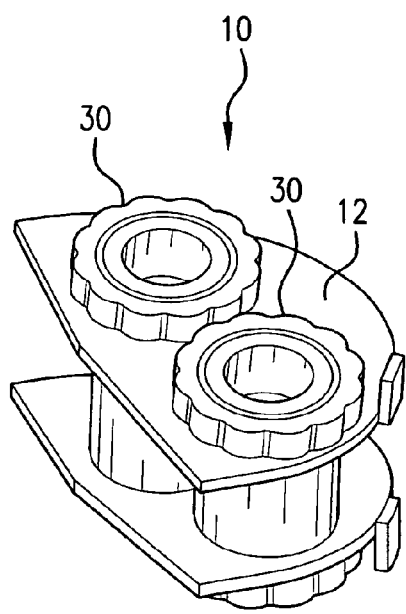
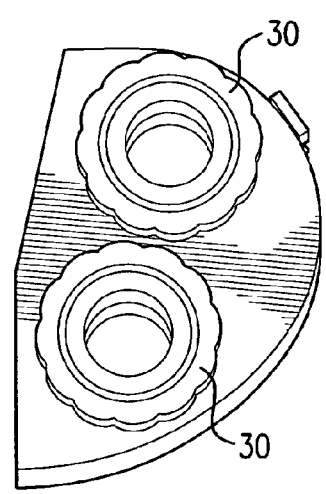
FIG.3C  FIG.3D

Section A-A

Section A-A

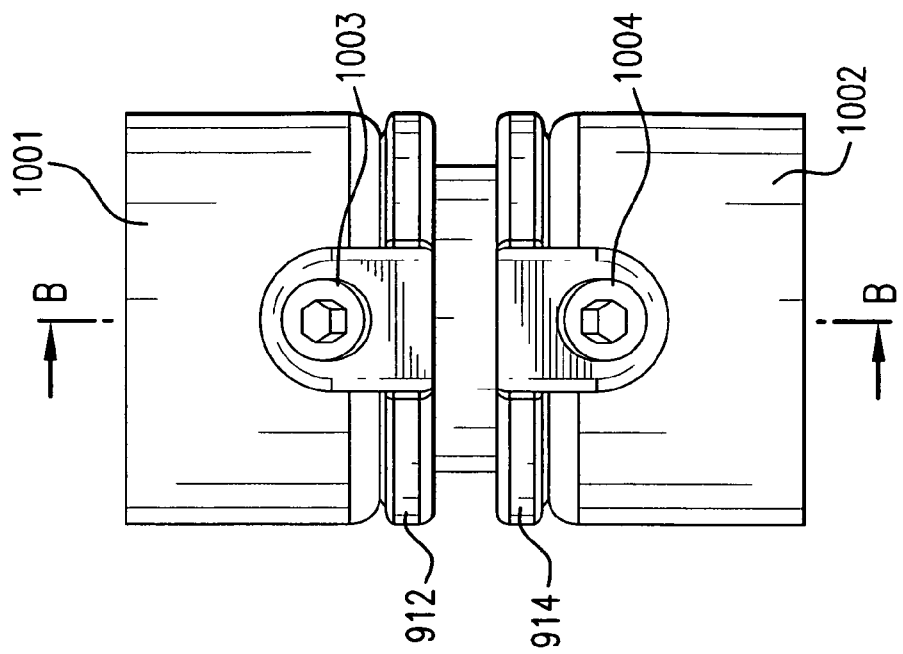
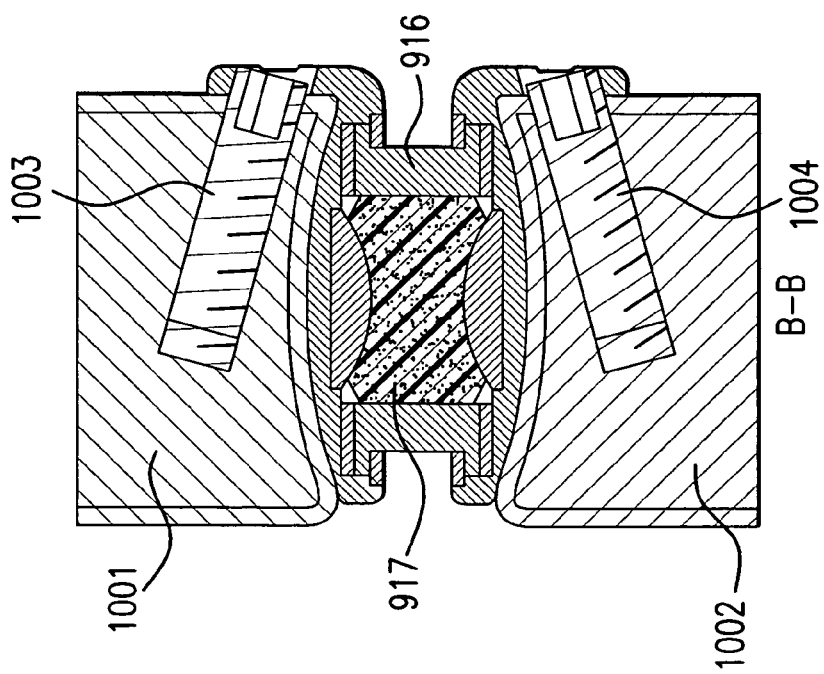
FIG. 10D
FIG. 10C

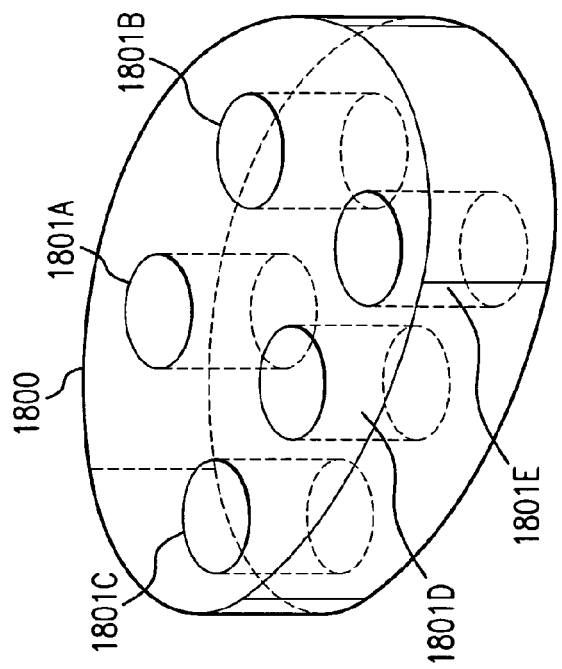
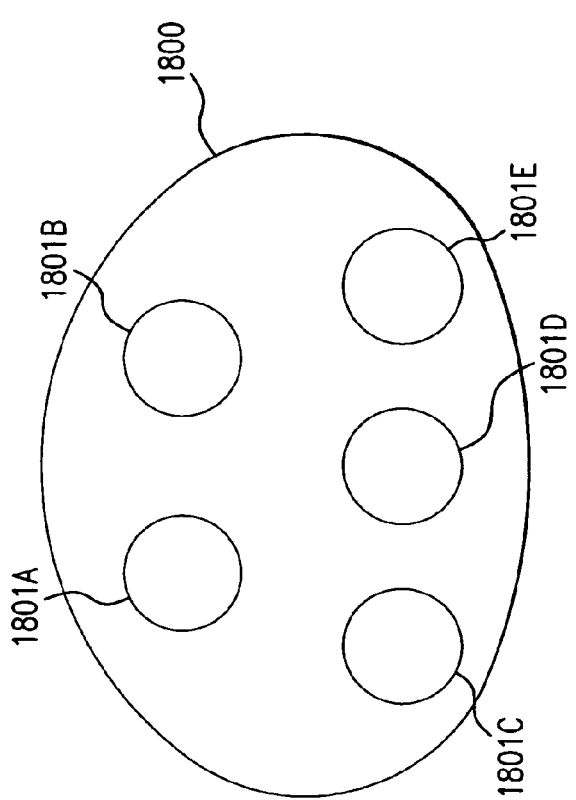
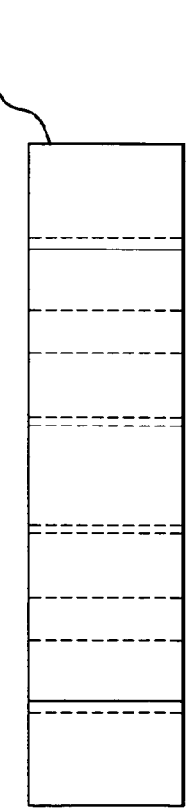
FIG.18C
FIG.18A
FIG.18B

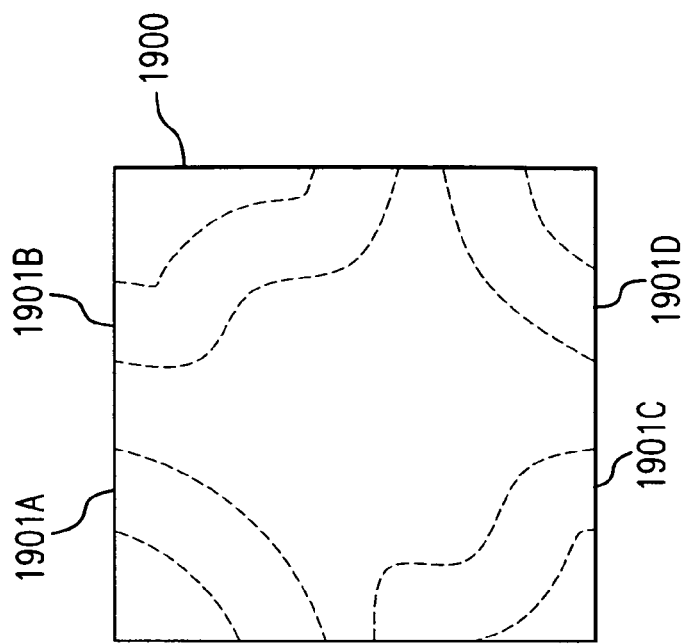
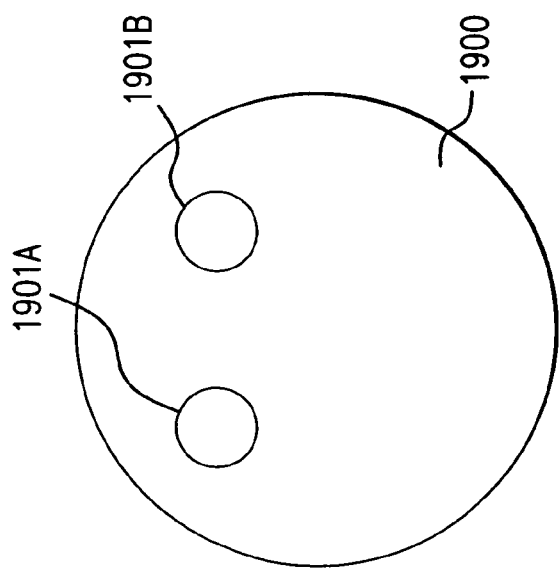

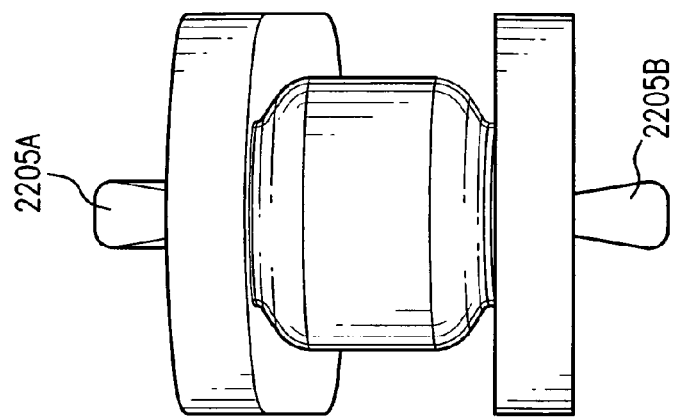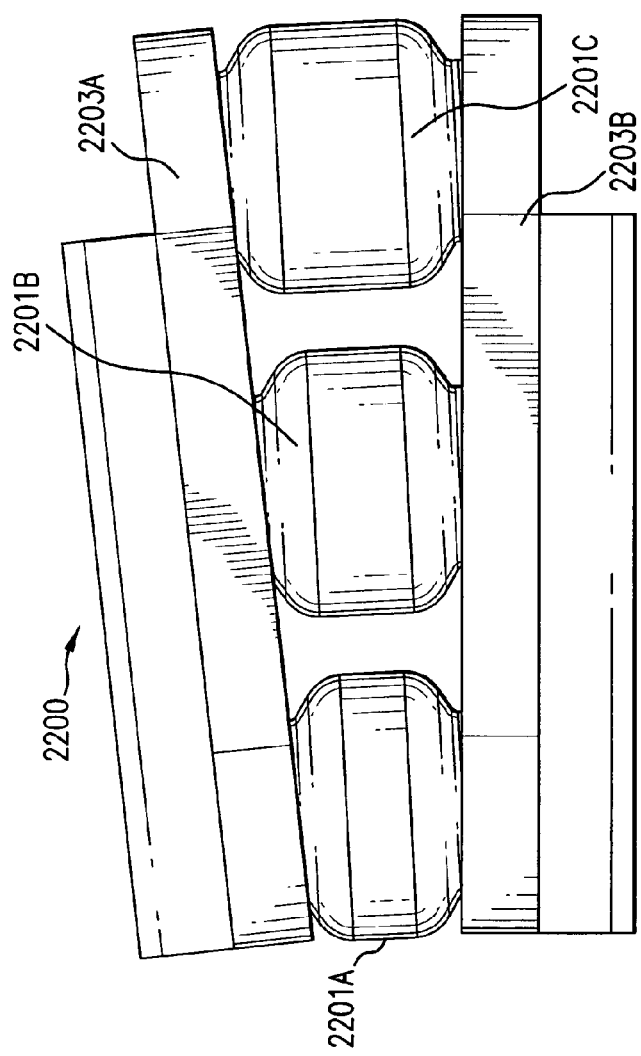

ARTIFICIAL INTERVERTEBRAL DISC

CROSS-REFERENCE TO RELATED APPLICATIONS

This application claims the benefit under 35 U.S.C. 119(e) of U.S. Provisional Application Ser. No. 60/375,842 filed Apr. 25, 2002 and claims the benefit under 35 U.S.C. 120 and is a continuation-in-part of U.S. application Ser. No. 10/423,414, filed Apr. 25, 2003 now U.S. Pat. No. 6,960,232.

FIELD OF THE INVENTION

The present invention is directed to the field of prosthetic devices. More particularly, one embodiment of the present invention is directed to an artificial disc that can be used as a replacement for an intervertebral disc (e.g., a human intervertebral lumbar disc, a human intervertebral cervical disc and/or a human intervertebral thoracic disc).

For the purposes of the present application the term "column" (e.g., as in ePTFE column) is intended to refer to a solid, partially hollow or hollow structure having any desired aspect ratio and any desired cross-section (cross-sectional shape and/or cross-sectional area). In one example (which example is intended to be illustrative and not restrictive) such a column may have a high length to width aspect ratio (i.e., the column may be "elongated"). In another example (which example is intended to be illustrative and not restrictive) such a column may have a low length to width aspect ratio (i.e., the column may be "squat"). In another example (which example is intended to be illustrative and not restrictive) the walls of the column may be thick enough to provide a substantial degree of inflexibility to the column. In another example (which example is intended to be illustrative and not restrictive) the walls of the column may be thin enough to provide a substantial degree of flexibility to the column. In other examples (which examples are intended to be illustrative and not restrictive) such a column may have a cross-section which is circular, oval, square or "kidney-shaped".

Further, for the purposes of the present application the term "filler" (e.g., as in column filler) is intended to refer to a substance disposed within a space or void which partially or fully fills the volume of the space or void.

Further still, for the purposes of the present application the term "composite structure" is intended to refer to a hollow or partially hollow column including a filler disposed therein.

Further still, for the purposes of the present application the term "ePTFE" is intended to refer to: (a) a PTFE material that has been expanded and sintered; or (b) a PTFE material that has been expanded, formed, attached to another material (e.g., fusion welded) and sintered.

BACKGROUND OF THE INVENTION

As an alternative to spinal fusion techniques, numerous attempts have been made to design an artificial disc to replace, for example, an intervertebral lumbar disc that has become damaged or otherwise unhealthy.

SUMMARY OF THE INVENTION

One embodiment of the present invention provides an artificial intervertebral disc ("AID") assembly comprised of first and second anchor plates (each of which has a vertebrae contacting side) and at least one composite structure that is fixed to the first and second anchor plates. The composite structure may be comprised of a column of expanded poly (tetraflouroethylene) ("ePTFE"). The column of ePTFE may be at least partially hollow (e.g., having one or more holes therein) and may be filled (fully or partially) with a compressible material, such as an elastomer. For example (which example is intended to be illustrative and not restrictive), the elastomer may include a silicone, a urethane, a thermoplastic elastomer, an elastomer alloy; a polyurethane/polycarbonate alloy, and/or any combination thereof.

Of note, the column filler (e.g., elastomer) may store energy and then return the stored energy back to the physiological system (because the column filler (e.g., elastomer) may allow physiological-like displacement, the column filler (e.g., elastomer) may (like a physiological system) dissipate some strain energy).

Of further note, ePTFE is a material processed from PTFE polymer. ePTFE has a configuration (e.g., a network of nodes and fibrils) that imparts certain expandability, compressibility, and porosity properties to the ePTFE. More particularly, ePTFE is described in U.S. Pat. No. 3,953,566 as follows "in the case of uniaxial expansion the nodes are elongated, the longer axis of a node being oriented perpendicular to the direction of expansion. The fibrils which interconnect the nodes are oriented parallel to the direction of expansion. These fibrils appear to be characteristically wide and thin in cross-section, the maximum width being equal to about 0.1 micron (1000 angstroms) which is the diameter of the crystalline particles. The minimum width may be 1 or 2 molecular diameters or in the range of 5 or 10 angstroms. The nodes may vary in size from about 400 microns to less than a micron, depending on the conditions used in the expansion. Products which have been expanded at high temperatures and high rates have a more homogeneous structure, i.e. they have smaller, more closely spaced nodes and these nodes are interconnected with a greater number of fibrils. These products are also found to have much greater strength." This patent is incorporated herein by reference.

Of still further note, the network of nodes and fibrils of an ePTFE tubular structure allows axial compressive and extensive freedom, while at the same time, allowing relatively high radial strength. It is believed that when the ePTFE tubular structure is internally filled (e.g., with an elastomer), the composite structure presents very similar compressive load/deflection behavior to that of a healthy, intervertebral lumbar, thoracic, or cervical disc. That is, the amount of force needed to compress the ePTFE/elastomer composite structure, increases non-linearly. Further, ePTFE allows for both compression and extension locally within the same structural member, which mimics the behavior of an intervertebral disc in the modes of spinal extension, flexion, and lateral bending.

In a general sense, a compressive coil spring resists deflection according to its spring constant, which establishes a linear relationship between applied load and reactive deflection. It is believed that this linear relationship largely holds true until the point at which adjacent coils of the spring begin to contact one another, a phenomenon called stacking. Once a spring begins to stack, the ability of the spring to compress becomes less and less, resulting in a greater and greater spring constant. When fully stacked, any further load applied is resisted according to the compressive elastic modulus of the spring material itself, not by the torsional properties of the continuous beam that makes up the coils.

Similarly, it is believed that when compressed (e.g., between two plates), a volume of elastomer exhibits a linear load/deflection relationship up until the point at which the elastomer no longer has the room to bulge out radially, or the point at which the material is constrained from migrating to the edges by the interior molecular bonds. At this point, the load increases more rapidly (e.g., per unit deflection) in a phenomenon termed "molecular stacking". While an elastomeric spring typically exhibits a reasonably linear increase in resistance to load application as the deflection increases, the compressive load/deflection behavior of a healthy intervertebral lumbar, thoracic, or cervical disc is somewhat non-linear. That is, the in vivo disc exhibits a continuously increasing stiffness as compressive deflection is increased. This in vivo behavior of increasing spring constant can be mimicked by constraining the elastomeric material radially. By disallowing the elastomer from bulging out freely in the radial direction, the molecular stacking behavior of the "spring" occurs at lower loads and thus, is enhanced. By controlling the degree to which the elastomer is constrained, this enhanced molecular stacking can be controlled, allowing a close match to the in vivo behavior of the intervertebral disc. Using ePTFE, for example, as the constraining member allows for a material which can expand and contract axially with the deflection of the elastomer, while at the same time, maintaining an essentially consistent resistance to radial bulge (in other words, the ePTFE provides good "hoop strength").

In one example (which example is intended to be illustrative and not restrictive), the compressive properties of the artificial intervertebral disc may be tuned to largely match those found in a natural intervertebral disc by utilizing a generally parabolic function. In a specific example applicable to a cervical disc (when deflection is plotted on the x-axis and compressive load is plotted on the y-axis), the parabola generally may be described by the function $y = A\ x^2 + B\ x + C$, where the coefficient A is in the range of 700 to 2000, the coefficient B is in the range of 0 to 1500, and the coefficient C is in the range 0 to 100 (the increasing stiffness is indicated by the increasing slope of the load-deflection curve at higher loads and deflections).

In another embodiment the AID assembly may be constructed of first and second anchor plates, each of which has a vertebrae contacting side, and a plurality of composite structures that are fixed to the first and second anchor plates. In one example (which example is intended to be illustrative and not restrictive) 2-8 composite structures may be fixed to the anchor plates.

In another embodiment the AID assembly may be provided with one or more anchor plates that have one or more undercuts and/or one or more tabs to facilitate the anchoring of the AID assembly to the vertebral bodies. In one example (which example is intended to be illustrative and not restrictive) the tabs may be provided with screw-holes into which bone screws can be inserted to anchor the assembly to the vertebral bodies. In another example (which example is intended to be illustrative and not restrictive) the screw holes and/or the tabs may be angled relative to the vertebrae bodies (e.g., to pull all or part of the AID assembly diagonally against the vertebrae).

In another embodiment the anchor plates may be assembled such that the anchor plates are non-parallel (e.g., in order to provide a profile that substantially corresponds to the lordotic profile of the vertebral bodies/intervertebral space). In one example (which example is intended to be illustrative and not restrictive), the non-parallel angle may be about 5° to about 15°.

In another embodiment a final AID assembly may be comprised of multiple assemblies (e.g., matching left and right assemblies), each assembly having first and second anchor plates and at least one composite structure that is fixed to the anchor plates. In one example (which example is intended to be illustrative and not restrictive) the left and right assemblies may be sized and dimensioned to reside adjacent to each other when positioned in the space between vertebral bodies.

In another embodiment compression ferrules (e.g., radial compression ferrules) may fix the composite structure to the anchor plates. In one example (which example is intended to be illustrative and not restrictive), the ferrules may be fitted inside the column of the composite structure and, as a result of the sizing of the ferrules relative to the sizing of the openings in the anchor plates, the ferrules may impinge against the inner wall of the column and force it outward against the walls of the anchor plates at their openings.

In another embodiment the ferrules may be expanded after fitting inside the column of the composite structure, such expansion being caused, for example, by the advancement of a tapered set screw or another tapered part within the ferrule.

In another embodiment the inner wall of the column of the composite structure may be impinged upon to force it outward against the walls of the anchor plates by means of a tapered set screw or other tapered part advancing within the column and in direct contact with the inside wall of the column.

In another embodiment one or more portions of the column of the composite structure (e.g., the ends) may be formed into any appropriate shape (e.g., may be flared) and a compression flange affixed onto the anchor plate, trapping the ends of the column (e.g., once the column has been inserted through the anchor plates) in order to force the ends of the column axially into frictional engagement with the anchor plates.

In another embodiment one or more portions of the column of the composite structure (e.g., the ends) may be formed into any appropriate shape (e.g., may be flared or flanged such that the end portions of the column wall are reoriented in a plane essentially perpendicular to the longitudinal axis of the column). This may be accomplished by the application of heat and/or pressure to the end portions of the column wall. In one example (which example is intended to be illustrative and not restrictive), pressure may be applied via a fixture capable of stretching the column wall radially and then compressing the column wall axially. After reorienting the ends of the column, a compression flange affixed to the anchor plate may trap each end of the column (e.g., once the column has been inserted through the anchor plates). The compression flanges may axially force the ends of the column into planar frictional engagement with the anchor plates.

In another embodiment one flanged or flared end of the column of the composite structure can be compressed against the bottom surface of the top anchor plate by a compression fit. Likewise, the other flanged or flared end of the column of the composite structure can be compressed against the top surface of the bottom anchor plate by a compression fit.

In another embodiment one flanged or flared end of the column of the composite structure can be compressed against the bottom surface of the top anchor plate by a capture ring. Likewise, the other flanged or flared end of the column of the composite structure can be compressed against the top surface of the bottom anchor plate by a capture ring. This capture ring can either be a unitary part, in which case the column of the composite structure may be inserted through the ring before being flared, or the capture ring can be two or more parts (e.g., separated roughly in half across a diameter) such that the ring may be assembled around the column near the flange before being assembled into the anchor plate, capturing the flange (e.g., after weld and sinter).

In another embodiment the column of the composite structure (e.g., the ePTFE column) and/or the capture ring may be treated (e.g., on one or both mating surfaces) to aid in creating a tight, high-friction fit.

In another embodiment the AID assembly may be comprised of first and second anchor plates (e.g., top and bottom anchor plates) and at least one composite structure including a column (e.g., an ePTFE column) that is fixed to the anchor plates. In one specific example (which example is intended to be illustrative and not restrictive), the ePTFE column, prior to being sintered, may be engaged (for example, at each end) with a respective flange element (e.g., made from a presintered or post-sintered compatible flouropolymer (e.g., FEP, PFA, or PTFE modified to enhance its bonding capabilities)). Each flange element may be, for example, a holed disc, similar to a washer. Each flange element may be brought into tight engagement with the ePTFE column, and then sintered as an assembly. A fixture that provides high pressure on the wall surface of the column and/or the flange element can be employed to enhance the engagement of the ePTFE column with the flange element. Each end of the column so produced (i.e., including the engaged flange element) may hereinafter be referred to as a "composite flange". The final assembly is believed to posses high connective strength at the interface of the engaged parts.

In another embodiment the column of a composite structure (e.g., an ePTFE column) may be bonded (e.g., physically or chemically bonded) to another element made, for example, from PTFE, ePTFE, modified PTFE (e.g., modified to enhance its bonding capabilities), or another compatible flouropolymer such as FEP or PFA, to form a composite flange. For example, the ePTFE column may be heat-sealed, ultrasonically welded and/or fusion welded to another element made, for example, from PTFE, ePTFE, modified PTFE (e.g., modified to enhance its bonding capabilities), or another compatible flouropolymer such as FEP or PFA.

In another embodiment the column of a composite structure (e.g., an ePTFE column) may be impregnated with an elastomer (e.g., urethane or silicone) in order that the impregnated column can be bonded to another compatible structure, thus allowing for termination to the anchor plate.

In another embodiment (e.g., related to a modular design) the column(s) of the composite structure(s) may be terminated (e.g., using any of the above described means) to intermediate end-pieces, which are then affixed to the anchor plates by one or more of a variety of means, thus allowing for interchangeable heights and stiffnesses to provide a custom device for a patient's specific needs. Such customization may be provided, for example (which example is intended to be illustrative and not restrictive), via use of screw(s), threaded mechanism(s), and/or various sized insert(s) or ring(s).

In another embodiment, an artificial intervertebral disc includes a first anchor member, a second anchor member, at least a first dome element with at least one curved face and a composite structure. The first and second anchor members have opposing internal surfaces facing one another. The composite structure includes a column including ePTFE and a column filler including an elastomer. The composite structure is disposed between the opposing internal surfaces of the first anchor member and the second anchor member with the first dome element between at least a portion of the column filler and the internal surface of the first anchor member such that a curved interface exists between the first dome element and the column filler and such that movement of the first anchor member and second anchor member relative to one another causes the first dome element to move relative to the column filler and such that the first dome element has convex curvature that corresponds to a concave curvature of the column filler. The curved interface is spaced apart from the internal surface of the second anchor member and defines an apex, the apex being a point on the first dome element that is spaced from the internal surface of the second anchor member by the shortest distance.

Of note, making a portion of the column of the composite structure relatively hard (and/or connecting the column of the composite structure to a relatively hard flange or other device) may aid in attaching the column of the composite structure to the anchor plates (e.g., a hard material may not have to be clamped down on as hard as a softer material).

Of further note, it is contemplated that each AID assembly of the present invention may be inserted using any desired surgical approach. For example (which example is intended to be illustrative and not restrictive), a posterior approach may be utilized. In another example (which example is intended to be illustrative and not restrictive), a posterior, lateral approach may be utilized. In another example (which example is intended to be illustrative and not restrictive), an anterior approach may be utilized.

BRIEF DESCRIPTION OF THE DRAWINGS

FIG. 2A shows a side elevation view along one side of an AID assembly according to an embodiment of the present invention;

FIG. 2B shows a cross sectional view of an AID according to an embodiment of the present invention;

FIG. 2C shows a side elevation view along another side of an AID assembly according to an embodiment of the present invention;

FIG. 2D shows a perspective view of an AID assembly according to an embodiment of the present invention;

FIG. 2E shows a top plan view of an AID assembly according to an embodiment of the present invention;

FIG. 3A shows a side elevation view along one side of an AID assembly according to an embodiment of the present invention;

FIG. 3B shows a side elevation view along another side of an AID assembly according to an embodiment of the present invention;

FIG. 3C shows a perspective view of an AID assembly according to an embodiment of the present invention;

FIG. 3D shows a top plan view of an AID assembly according to an embodiment of the present invention;

FIG. 10C shows a cross sectional view of an AID assembly (disposed between two vertebrae);

FIG. 10D shows an elevational view of the AID assembly of FIG. 10C (disposed between two vertebrae);

FIGS. 18A-18C show another embodiment of the present invention (FIG. 18A is a top view, FIG. 18B is a side view, and FIG. 18C is a perspective view);

FIGS. 19A and 19B show another embodiment of the present invention (FIG. 19A is a top view and FIG. 19B is a side view);

FIGS. 21A-20C show other embodiments of the present invention;

FIGS. 22A-22E show other embodiments of the present invention;

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

Figure 8:
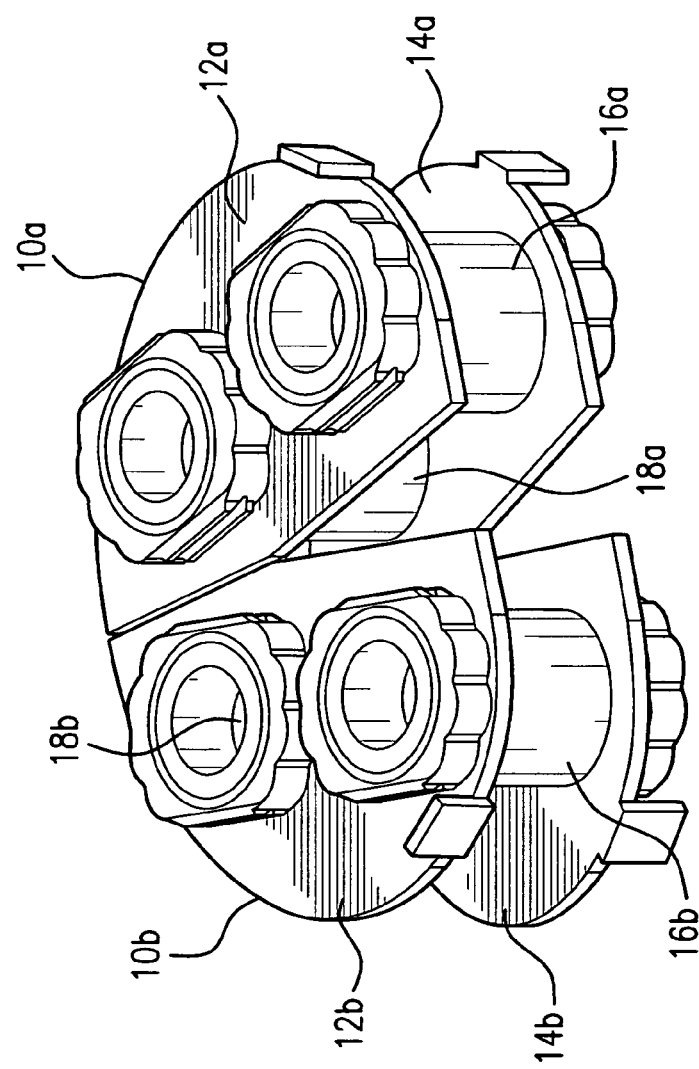
FIG. 8 shows a perspective view of another embodiment of the present invention in which the AID assembly is comprised of a pair of implant components.

As discussed above, the AID of the present invention may be comprised of one or more components or assemblies. In this regard, it is noted that certain Figures show views of assemblies which may be combined (as shown in FIG. 8, for example) to produce a final artificial intervertebral disc.

Figure 1:
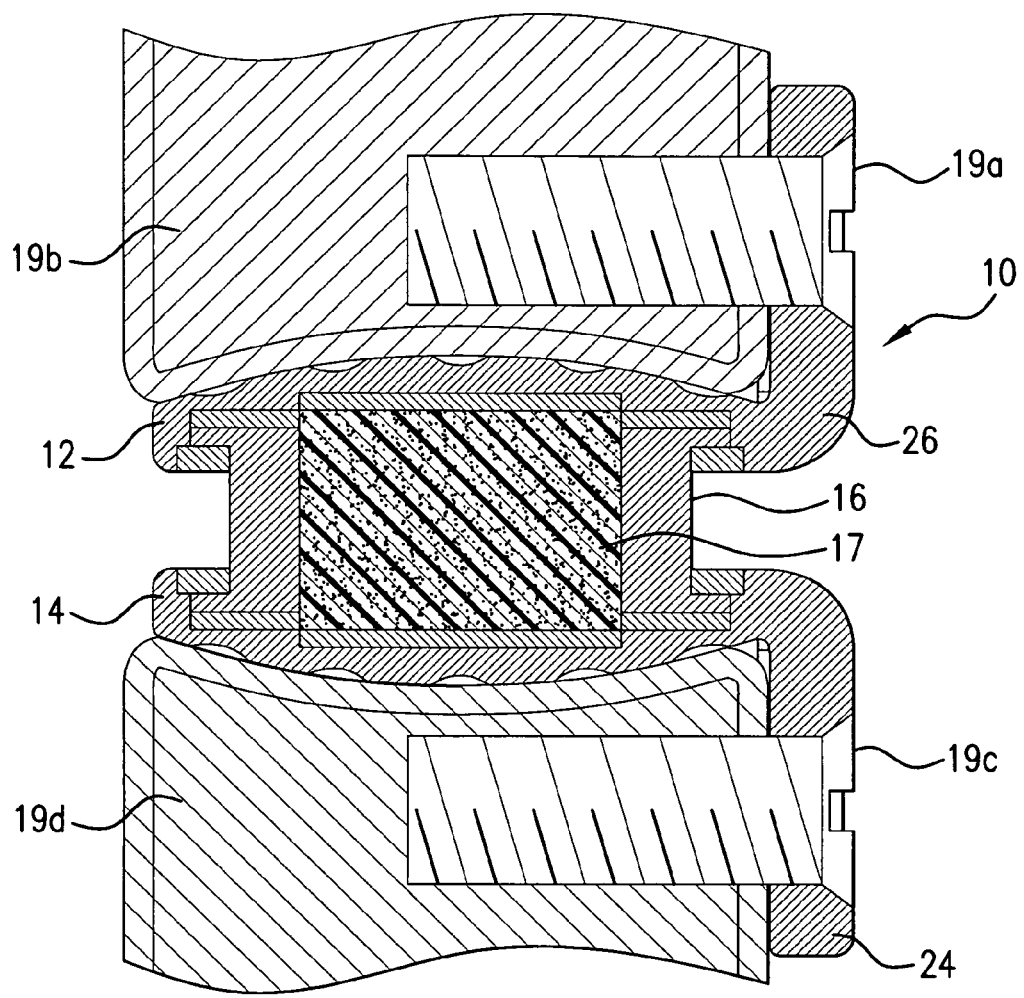
FIG. 1 shows a cross sectional view of an AID assembly according to an embodiment of the present invention.
Figure 4A:
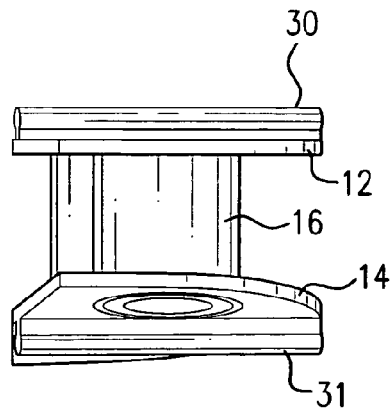
FIG. 4A shows a side elevation view along one side of an AID assembly according to an embodiment of the present invention.
Figure 4B:
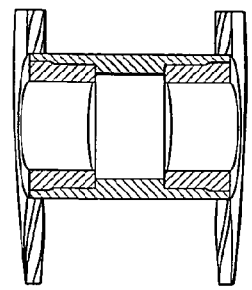
FIG. 4B shows a cross sectional view of an AID assembly according to an embodiment of the present invention.
Figures 4C, 4D:
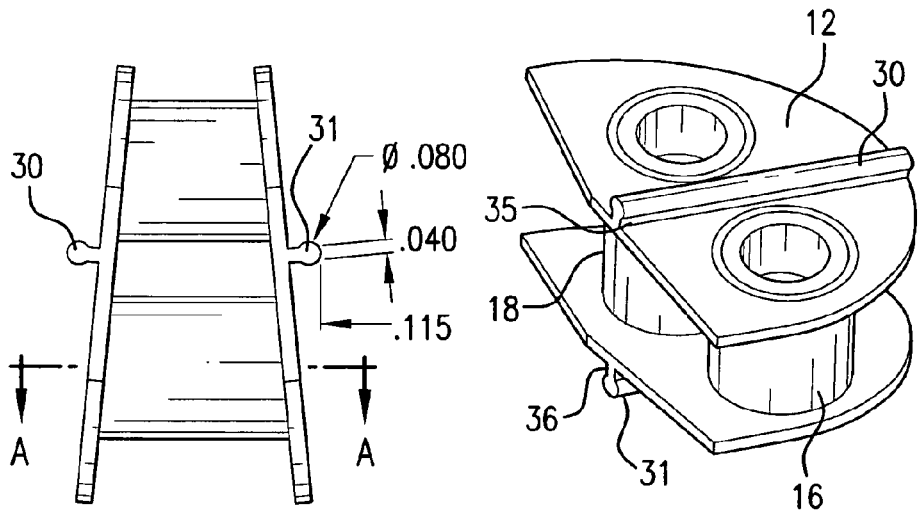
FIG. 4C shows a side elevation view along another side of an AID assembly according to an embodiment of the present invention.
FIG. 4D shows a perspective view of an AID assembly according to an embodiment of the present invention.
Figure 4E:
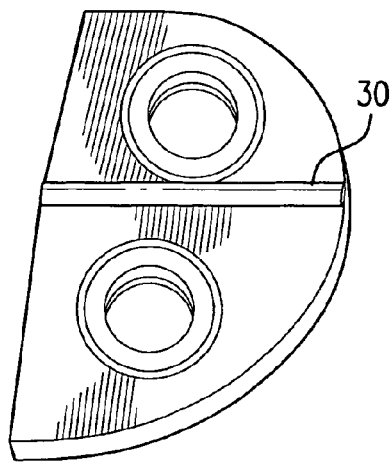
FIG. 4E shows a top plan view of an AID assembly according to an embodiment of the present invention.

Referring now to FIG. 1, an AID assembly according to an embodiment of the present invention is shown. As seen in this Figure, AID assembly 10 is comprised of a first anchor plate 12 and a second anchor plate 14, between which is disposed column 16. Column 16 (which is formed of ePTFE) includes therein column filler 17 (which is formed of an elastomer). Anchor plate 12 includes a mechanism (threaded fastener 19a) for attachment to a vertebral body 19b. Likewise, anchor plate 14 includes a mechanism (threaded fastener 19c) for attachment to a vertebral body 19d.

Referring now to FIGS. 2A-2E, an AID assembly according to another embodiment of the present invention is shown. As seen in these Figures, the AID 10 has a first anchor plate 12, a second anchor plate 14 (both of which may be constructed of titanium, for example), and columns 16, 18 which are constructed of ePTFE. The columns 16, 18 (including therein respective column fillers) serve as spacer elements between the anchor plates 12, 14. As shown in FIGS. 2B & 2D, for example, the end surface 32 of columns 16, 18 terminate flush at the top surface 34 of anchor plate 12 (as well as flush at the bottom surface of anchor plate 14, which configuration is not shown in this view). The outer diameter of the column lies against the inner diameter of the opening in the anchor plate. A compression ferrule 20, 22 is placed within the column at an end thereof, as shown in FIG. 2B. The ferrule is sized to form a snug fit between the ferrule, column, and sidewalls defining the opening of the anchor plate. This forms a firm frictional engagement between the components that locks the columns in place.

In another embodiment, the ends of the columns may be flared and a compression flange affixed onto the anchor plate, trapping the ends of the column (once the column has been inserted through the anchor plates) in order to force the ends of the column axially into frictional engagement with the anchor plates.

Figure 7:
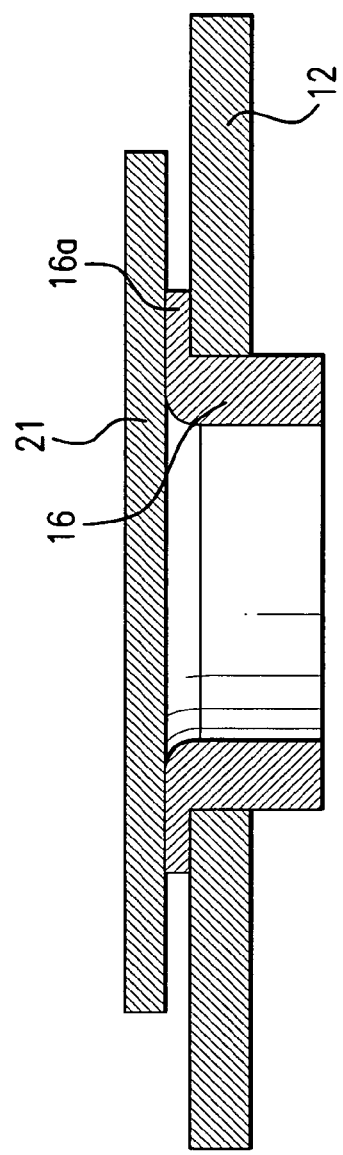
FIG. 7 shows a cross sectional view of a component of an AID assembly according to an embodiment of the present invention.

In yet another embodiment shown in FIG. 7, the ends of the column 16a are flared after extending through the thickness of the anchor plate such that the outer wall of the column lies against the top surface of the anchor plate 12 and the inner wall of the column faces outward axially. A compression flange 21 is affixed to the top surface of the anchor plate, forming a snug fit between the flange, column, and upper surface of the anchor plate. The flange 21 may be fixed to the anchor plate 12 by securing screws through bores provided in the flange and the anchor plate, or by another suitable arrangement, such as by passing bolts through bores provided in the flange and the anchor plate and securing the bolts with washers and nuts. When the flange is affixed in this manner, a firm frictional engagement is formed between these components, which locks the columns in place. An identical method of termination may be implemented at the opposite end of the column and bottom surface of anchor plate 14. In order to flare the end of the column, a slit may be provided at the end of the column, which could facilitate its flaring.

Referring once again to FIGS. 2A-2E, it is seen that in this embodiment there exists a portion 30, 31 of the anchor plate which is elevated beyond the surface, which elevated portion contacts the vertebral endplate. This elevated portion of the anchor plate may be the interface between the anchor plate and the vertebral body. The elevated interface may reside in a corresponding depression or groove formed in the vertebral endplate. The elevated interface may be furnished with an undercut 35, 36 to provide a dovetail fit between the anchor plate and the depression or groove that is formed in the vertebral body. This arrangement may facilitate the initial fixation of the AID assembly (e.g., by allowing the assembly to slide into place) and/or the ultimate fixation (e.g., by allowing bone to grow into the undercut region of the interface feature on the anchor plate). In one embodiment, the undercut 35, 36 may run linearly down the sides of the elevated portion, as in FIGS. 2A-2E. In yet another embodiment, the undercut 35, 36 may run down the center of the plate, as shown in FIGS. 4A-4E, in a configuration, which in its cross section (see FIG. 4C) resembles a light bulb, with a neck portion and a bulbous portion. In yet another embodiment, the undercut 35,36 may pass around the perimeter of the opening in the anchor plate, such as the daisy wheel configuration of FIGS. 3A-3D, or intersect linearly with a truncated daisy wheel configuration as in FIGS. 5A-5E.

The elevated interface may be provided on the anchor plate in order to form an interface between the vertebral bodies and the surface of the anchor plates. That is, over a period of time, the vertebral bodies may grow around the interface on each of the anchor plates, forming a complementary arrangement, which anchors the implant in place.

In this regard, it is noted that during the surgical procedure the surgeon may make the requisite incisions or access the site where the unhealthy or damaged disc is to be removed. After removal of the unhealthy or damaged disc or the unhealthy or damaged portion(s) of the disc, the surgeon may cut grooves in the endplates of the vertebral bodies that were adjacent to the removed disc. The grooves that are cut may be sized and shaped to correspond to the interface on the elevated portion of the anchor plate. Of note, the surgical procedure may also involve removing healthy portion(s) of the patient's disc(s) to the extent required for implantation of the AID assembly.

In one embodiment the compressibility of the implant of the present invention may prove helpful during the implanting procedure. For example, (which example is intended to be illustrative and not restrictive), as the implant is being inserted between the vertebrae, the implant may be compressed to smaller proportions than its uncompressed height. The surgeon can then, prior to releasing the implant from its compressed height, adjust its position to insure that the elevated interface on the anchor plates and the grooves cut into the vertebral bodies are aligned with each other. After the surgeon has ensured this is the case, the implant may be released from its compressed state, so that the elevated interface enters the grooves.

Alternatively, the grooves may be cut in the vertebral body with a matching undercut, such that the anchor plates may be inserted (e.g., from the side, front or back) in a dovetail configuration. This embodiment may allow for positive initial tensile attachment between the anchor plates and the endplates, without having to wait for bony ingrowth.

As shown in the Figures, the anchor plates may be disposed in a non-parallel configuration (in order to account for the lordotic angle of the vertebrae/intervertebral space, for example). This may help insure that the surface of the anchor plate will contact a respective surface of the vertebral bodies to the fullest possible extent. An AID constructed in this manner may exhibit behavior similar to that of the original disc, which also reflected the lordotic angle between vertebral bodies/intervertebral space. In one specific example, the angle may lie in the range of about 5° to about 15°, which (it is believed) should cover the lordotic angles of the vertebral bodies/intervertebral space of most of the population.

Figure 5A:
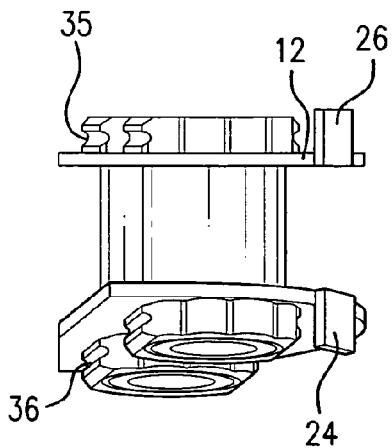
FIG. 5A shows a side elevation view along one side of an AID assembly according to an embodiment of the present invention.
Figure 5B:
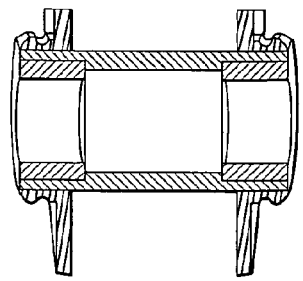
FIG. 5B shows a cross sectional view of an AID assembly according to an embodiment of the present invention.
Figure 5C:
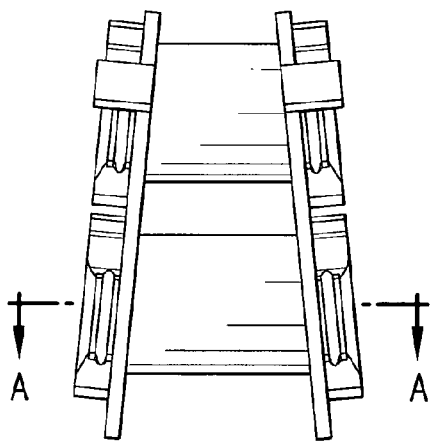
FIG. 5C shows a side elevation view along another side of an AID assembly according to an embodiment of the present invention.
Figure 5D:
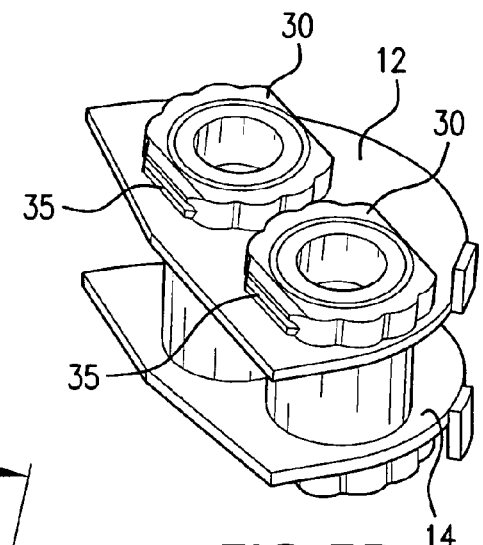
FIG. 5D shows a perspective view of an AID assembly according to an embodiment of the present invention.
Figure 5E:
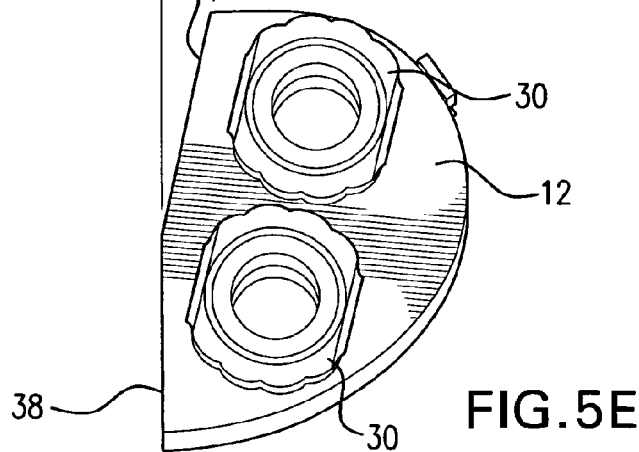
FIG. 5E shows a top plan view of an AID assembly according to an embodiment of the present invention.

Referring now to FIGS. 2E and 5E, for example, it can be seen that anchor plate edges 38 and 39 may form angle $\theta$. This angle may be provided to account for the angle at which the device enters the body. That is, the angle may be provided as a design feature in order to facilitate installation by particular approach, such as a posterior lateral approach, for example. Thus, the device may be designed to have a preselected angle $\theta$ that facilitates a particular approach to installation.

Figure 6:
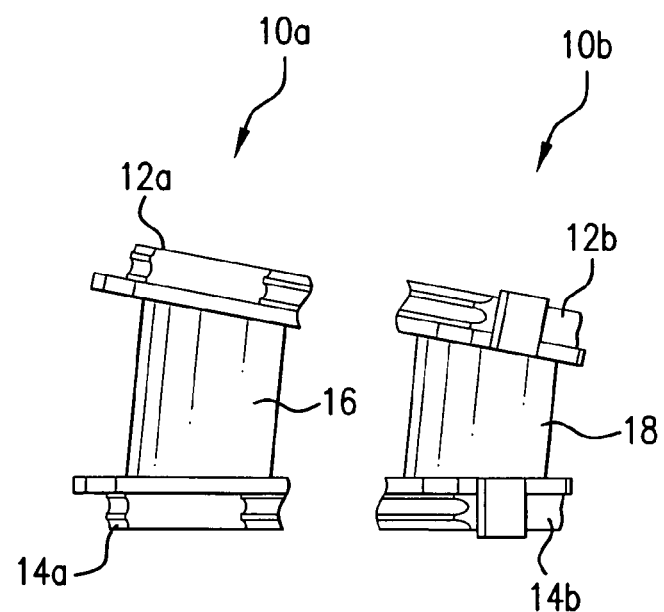
FIG. 6 shows a side elevational view of another embodiment of the present invention in which the AID assembly is comprised of a pair of implant components.

FIG. 6 shows another embodiment of the present invention in which the AID is comprised of a pair of implant components (or assemblies) 10a, 10b. Each component (or assembly) 10a, 10b is provided with anchor plates 12a, 14a, 12b, 14b, and columns 16, 18, fixed to the anchor plates in the manners previously discussed (respective column filler elements, not shown, may also be used). The implant components (or assemblies) may be provided with complementary, matching or corresponding lordotic profiles and may be intended to sit in front of and behind one another (as in this FIG. 6). In other embodiments the components (or assemblies) may be intended to sit laterally adjacent to each other. This arrangement may provide flexibility in the insertion process, allowing one component to be inserted from each side of the spinal cord, for example.

FIG. 8 shows another embodiment of the present invention in which the implant is comprised of a pair of implant components (or assemblies) 10a, 10b. Each component (or assembly) 10a, 10b is provided with anchor plates 12a, 14a, 12b, 14b, and columns 16a, 18a, 16b, 18b fixed to the anchor plates in the manners previously discussed (respective column filler elements, not shown, may also be used). The implant components (or assemblies) may be provided with matching or corresponding lordotic profiles and may be intended to sit laterally adjacent to each other and/or in front of and behind one another. This arrangement may provide flexibility in the insertion process, allowing one component to be inserted from each side of the spinal cord, for example. Of note, this FIG. 8 shows an embodiment comprised of one component (or assembly) similar to the one shown in the views of FIGS. 5A-5E and another component (or assembly)

also similar to the one shown in the views of FIGS. 5A-5E, but with an essentially mirror-image configuration. Multi-component (or multi-assembly) implants corresponding to embodiments shown in the other Figures are, of course, also contemplated by the present invention.

Turning now, for example, to FIGS. 1 to 8, it is seen that the perimeters of the anchor plates may be provided with tabs 24, 26. In one example (which example is intended to be illustrative and not restrictive), the tabs 24, 26 may extend at an angle substantially normal to the plane of the anchor plates. The tabs may also extend at an angle relative to this normal plane in order that the relation between the tab and the anchor plate more closely resembles that relation between the vertebral endplate and the substantially vertical outer surface of the vertebral body. The tabs 24, 26 may have an outer surface and an inner surface that faces in toward the anchor plates. The tabs 24,26 may aid in attaining the correct positioning of the implant relative to the vertebral bodies it is positioned between. In one example (which example is intended to be illustrative and not restrictive), the correct position may be attained when the inner surface of the tabs 24, 26 lie substantially flush against the outer surface of the vertebral bodies. Optionally, the tabs 24, 26 may be provided with through bores, through which fixation devices, such as bone screws, may be inserted in order to lock the implant in place.

Figure 9:
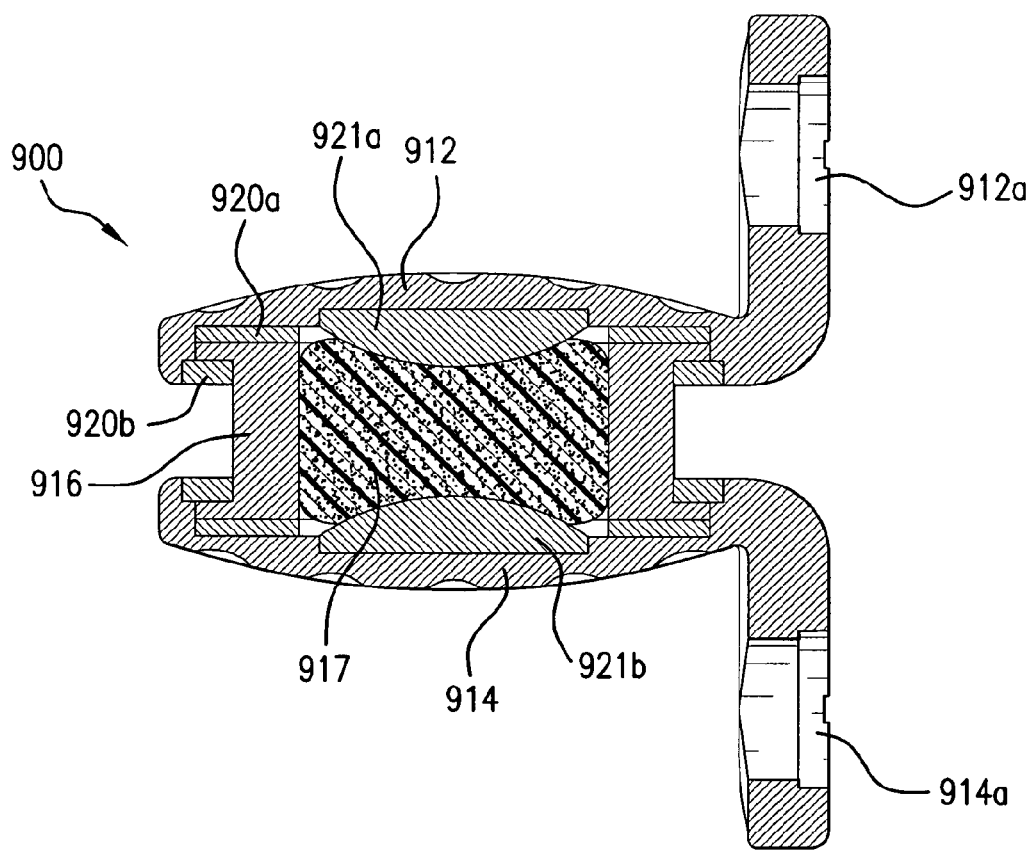
FIG. 9 shows a cross sectional view of another embodiment of the present invention in which the AID assembly utilizes a "dome-core-dome" internal configuration.

Referring now to FIG. 9, another embodiment of the present invention is shown in which the AID assembly utilizes a "dome-core-dome" internal configuration. More particularly, as seen in this Figure, AID assembly 900 is comprised of a first anchor plate 912 and a second anchor plate 914, between which is disposed column 916. Column 916 (which is formed of ePTFE) includes therein elastomer core 917. Column 916 may be attached to first anchor plate 912 and a second anchor plate 914 using any of the mechanisms described in the present application (in the example shown in this FIG. 9, the ePTFE at each end of the column 916 is flared, welded to flange 920a and captured behind capture ring 920b). Anchor plate 912 includes a mechanism (throughbore 912a) to aid in attachment to a vertebral body (not shown) by using a fastener (not shown). Likewise, anchor plate 914 includes a mechanism (throughbore 914a) to aid in attachment to a vertebral body (not shown) by using a fastener (not shown). In another example (which example is intended to be illustrative and not restrictive), the throughbores may include fastener mounting features for holding/orienting fasteners (e.g., bone screws).

Of note, in the embodiment shown in this FIG. 9, elastomer core 917 incorporates concave ends which mate with convex portions of corresponding intermediate elements 921a and 921b. In one example (which example is intended to be illustrative and not restrictive), these intermediate elements 921a and 921b may comprise "domes" formed at least in part from a material selected from the group including (but not limited to): PTFE, UHMWPE, a polyethylene, polished metal, and a high-lubricity, low-wear material. Such a configuration may promote advantageous "shear" translation. In addition, such a configuration may provide advantageous kinematics (e.g., the elastomer core may follow the motion of the spine and the domed surfaces may produce in vivo like translation and/or rotation.). In one example (which example is intended to be illustrative and not restrictive), the intermediate elements 921a and 921b may be attached to respective anchor plates via any of a number of means, including dimensional interference (press-fit), adhesive, and/or threaded means. In another example (which example is intended to be illustrative and not restrictive), the intermediate elements 921a and 921b may be "free floating". In another embodiment one or more of the domes may be integrally formed with one or more of the anchor plates.

Figure 10B:
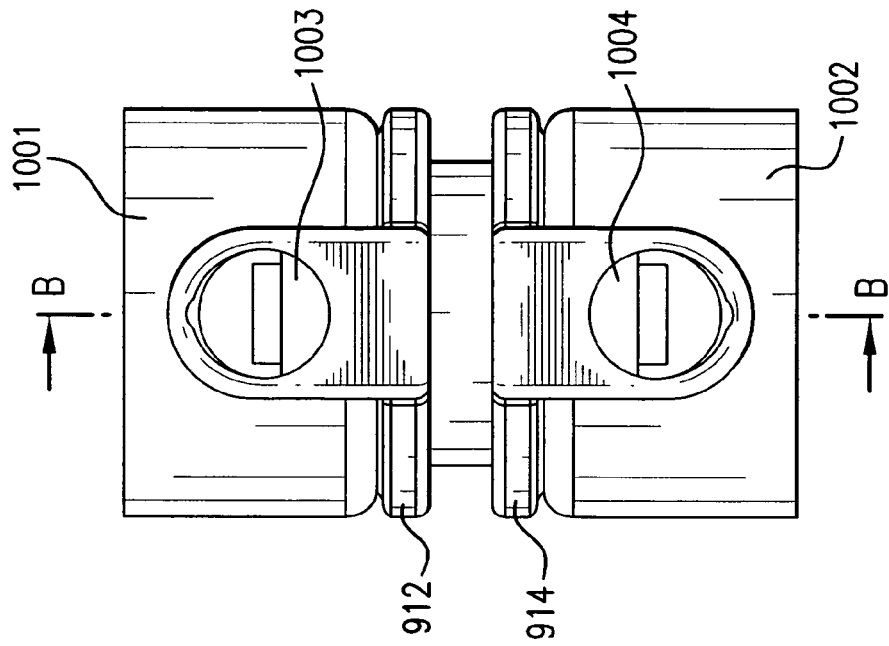
FIG. 10B shows an elevational view of the AID assembly of FIG. 9 (disposed between two vertebrae)
Figure 10A:
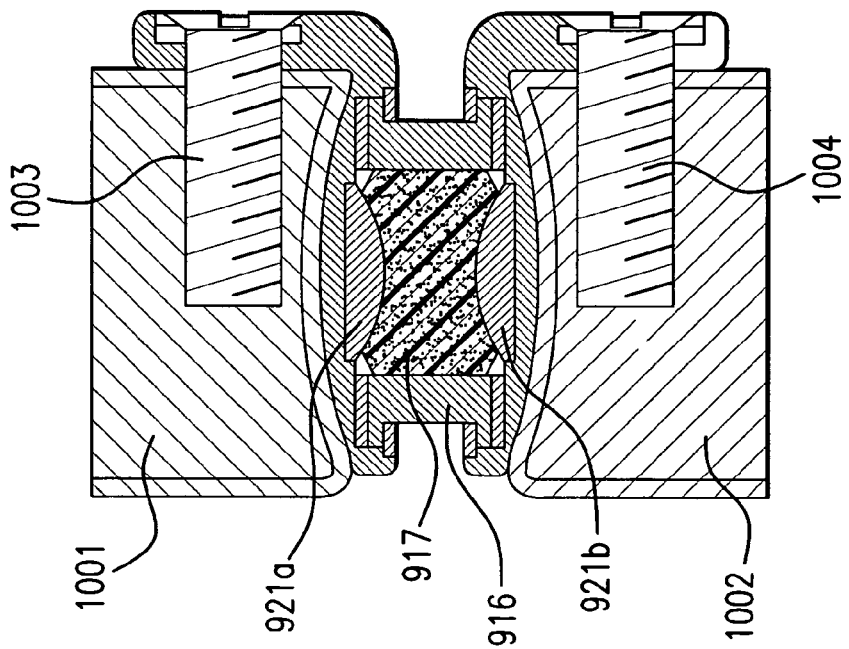
FIG. 10A shows a cross sectional view of the AID assembly of FIG. 9 (disposed between two vertebrae)

Referring now to FIG. 10A, a cross sectional view of the AID assembly of FIG. 9 (disposed between two vertebrae) is shown. Of note, the vertebrae are identified in this FIG. 10A as first vertebra 1001 and second vertebra 1002 and two fasteners (e.g., bone screws) are identified as elements 1003 and 1004 (other elements of this FIG. 10A are identified by the same reference numerals as the corresponding elements of FIG. 9).

Referring now to FIG. 10B, an elevational view of the AID assembly of FIG. 9 (disposed between two vertebrae is shown). Of note, elements of this FIG. 10B are identified by the same reference numerals as the corresponding elements of FIGS. 9 and 10A).

Referring now to FIG. 10C, a cross sectional view of an AID assembly similar to the AID assembly of FIG. 9 (disposed between two vertebrae) is shown. The vertebrae are identified in this FIG. 10C as first vertebra 1001 and second vertebra 1002 and two fasteners (e.g., bone screws) are identified as elements 1003 and 1004 (other elements of this FIG. 10C are identified by the same reference numerals as the corresponding elements of FIG. 9). Of note, this embodiment differs mainly from the embodiment of FIGS. 9, 10A and 10B in that this embodiment includes angled bone screws with hex drive interfaces.

Referring now to FIG. 10D, an elevational view of the AID assembly of FIG. 10C (disposed between two vertebrae) is shown. Of note, elements of this FIG. 10D are identified by the same reference numerals as the corresponding elements of FIG. 10C).

Figure 10E:
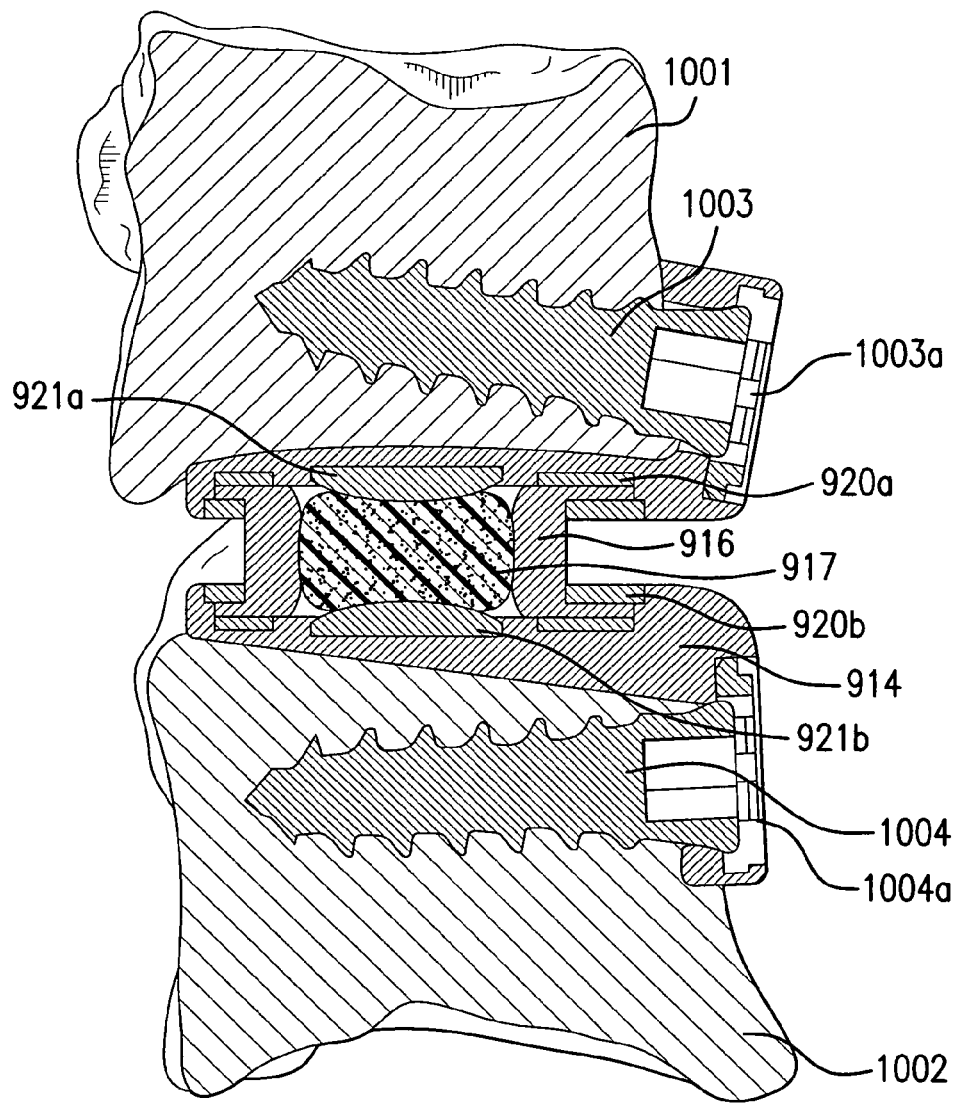
FIG. 10E shows a cross sectional view of the AID assembly of FIG. 10C (disposed between two vertebrae)

Referring now to FIG. 10E, a cross-sectional view of the AID assembly of FIGS. 10C and 10D is shown. Of note, elements of this FIG. 10E are identified by the same reference numerals as the corresponding elements of FIGS. 10C and 10D. Of further note, this view shows the torque lock washers 1003a and 1003b (used for fixing the bone screws 1003 and 1004 in place).

Figure 11:
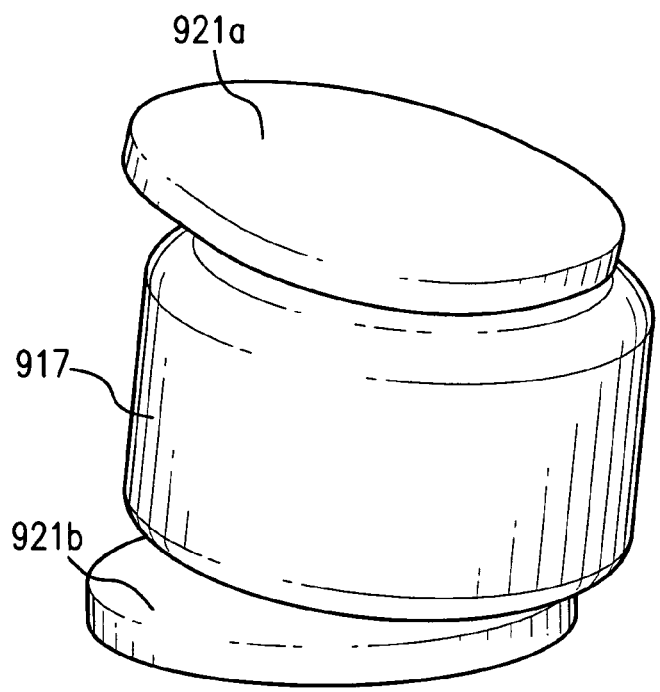
FIG. 11 shows a perspective view of certain interior parts of FIG. 9.

Referring now to FIG. 11, a perspective view of the intermediate elements 921a and 921b (e.g., PTFE "domes") and elastomer core 917 of FIG. 9 are shown.

Figure 12B:
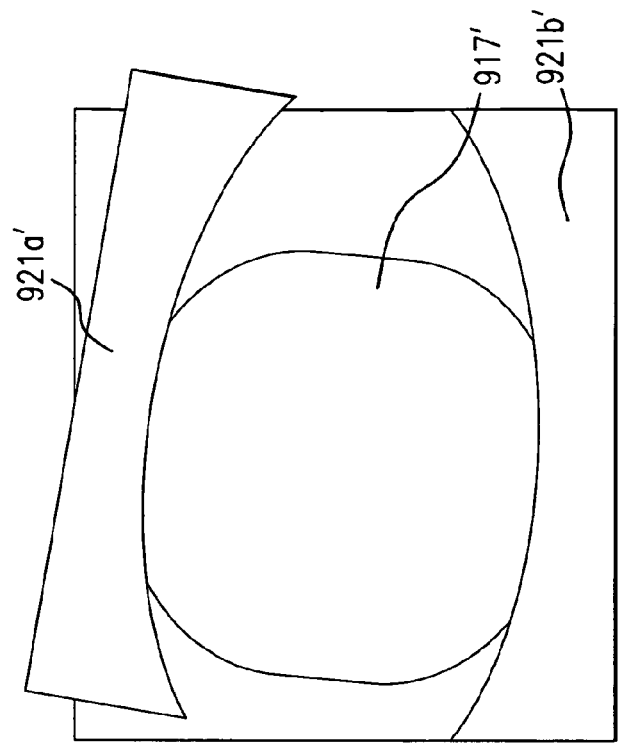
FIGS. 12A and 12B show a schematic view of an interior interface between parts of FIG. 9 (see FIG. 12A) and a schematic view of another embodiment of the interface (see FIG. 12B)
Figure 12A:
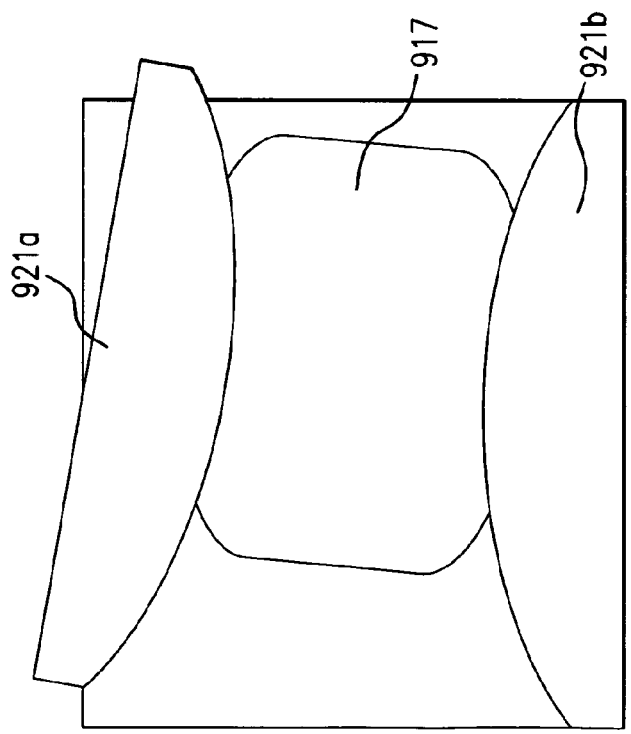

Referring now to FIGS. 12A and 12B, a schematic view of the interface between the intermediate elements 921a and 921b (e.g., PTFE "domes") and elastomer core 917 of FIG. 9 is shown (as FIG. 12A) and a schematic view of another embodiment of the interface between two intermediate elements 921a' and 921b' and elastomer core 917' is shown (as FIG. 12B). Of note, the configuration of FIG. 12A may result in the core following the motion of the spine as well as the promotion of shear translation, while the configuration of FIG. 12B may tend to resist shear translation.

Figure 13:
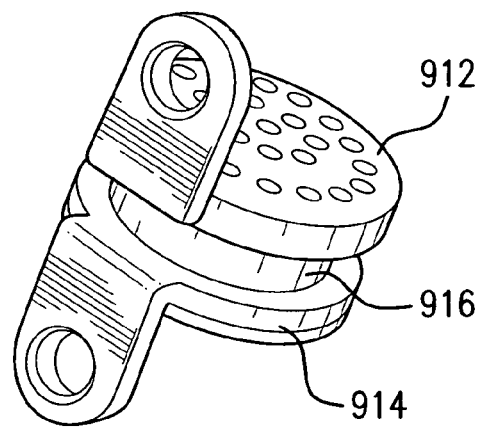
FIG. 13 shows a perspective view of the exterior of the AID assembly of FIG. 9.

Referring now to FIG. 13, a perspective view of the exterior of the AID assembly of FIG. 9 is shown.

Figure 14:
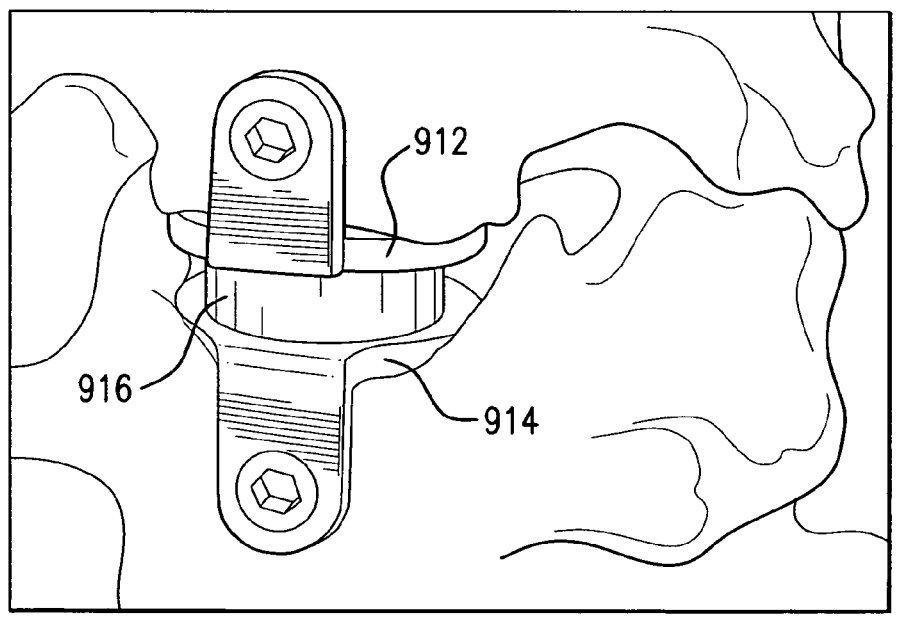
FIG. 14 shows a perspective view of the AID assembly of FIG. 9 (inserted between two vertebrae)

Referring now to FIG. 14, a perspective view of the AID assembly of FIG. 9 inserted between two vertebrae is shown.

Figure 15:
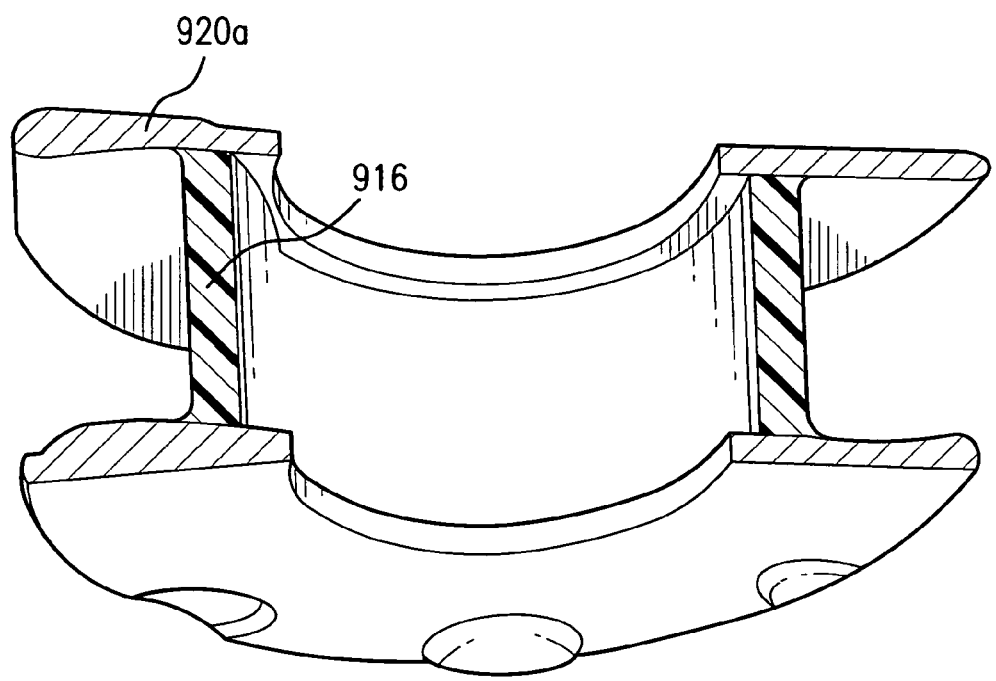
FIG. 15 shows a cross sectional view of an ePTFE column according to an embodiment of the present invention.

Referring now to FIG. 15, a cross sectional view of the ePTFE column 916 (of FIG. 9) welded to rigid flange 920a (of FIG. 9) is shown.

Figure 16B:
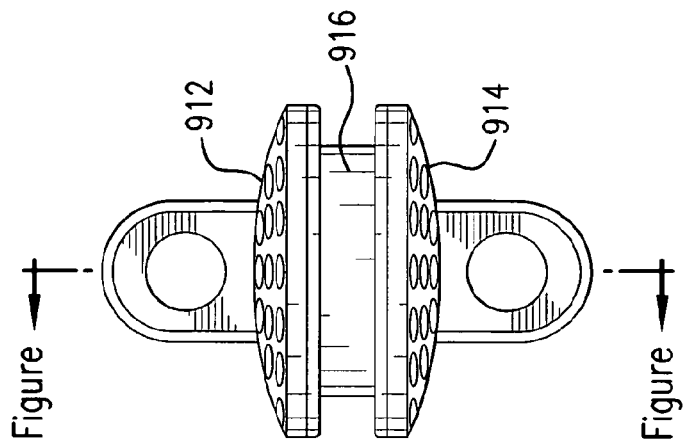
FIGS. 16A and 16B show another embodiment of the present invention (FIG. 16A is cross sectional view and FIG. 16B is an elevation view)
Figure 16A:
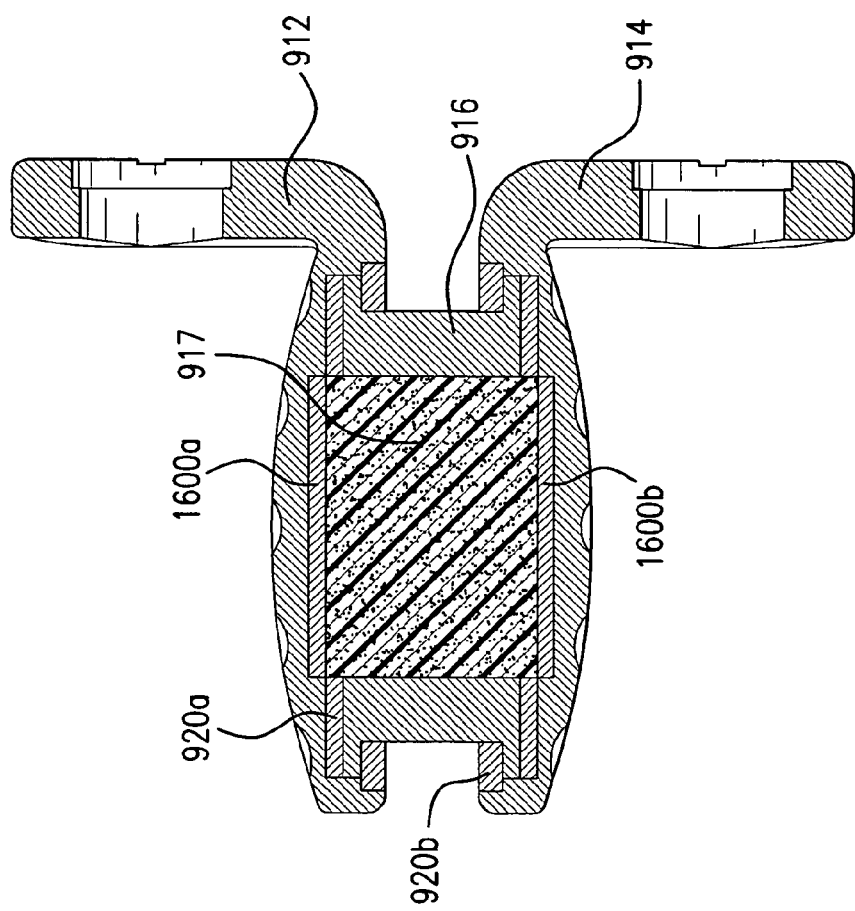

Referring now to FIG. 16A, a cross sectional view of an AID assembly similar to the AID assembly of FIG. 9 is shown. Similar elements of this FIG. 16A are identified by the same reference numerals as the corresponding elements of FIG. 9. Of note, this embodiment differs mainly from the embodiment of FIG. 9 in that this embodiment includes essentially flat "domes" 1600a and 1600b above and below the elastomer core.

Referring now to FIG. 16B, an elevational view of the AID assembly of FIG. 16A is shown. Of note, elements of this FIG. 16B are identified by the same reference numerals as the corresponding elements of FIG. 16A.

Figure 17B:
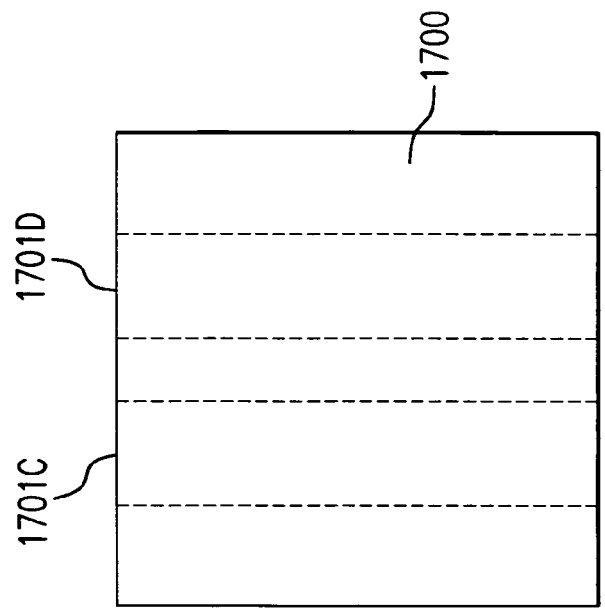
FIGS. 17A and 17B show another embodiment of the present invention (FIG. 17A is a top view and FIG. 17B is a side view)
Figure 17A:
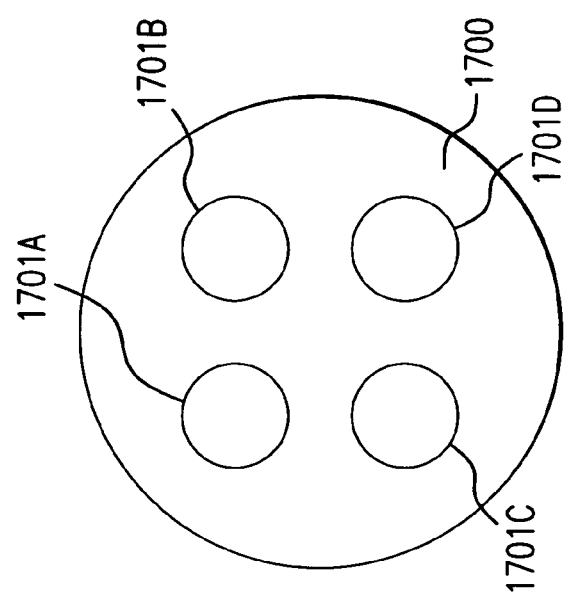

Referring now to FIGS. 17A and 17B, another embodiment of the present invention is shown in which ePTFE column 1700 includes a number of holes 1701A-1701D therethrough in which respective column filler elements (e.g., formed from an elastomer) are disposed (FIG. 17A is a top view and FIG. 17B is a side view). Of course, four holes are shown as an example only (which example is intended to be illustrative and not restrictive), and any desired number of holes may be used. Further, some or all of the holes may include the filler (e.g., some of the holes may be fully or partially empty).

Referring now to FIGS. 18A-18C, another embodiment of the present invention is shown in which ePTFE column 1800 includes a number of holes 1801A-1800E therethrough in which respective column filler elements (e.g., formed from an elastomer) are disposed (FIG. 18A is a top view, FIG. 18B is a side view and FIG. 18C is a perspective view). Of course, five holes are shown as an example only (which example is intended to be illustrative and not restrictive), and any desired number of holes may be used. Further, some or all of the holes may include the filler (e.g., some of the holes may be fully or partially empty).

Referring now to FIGS. 19A and 19B, another embodiment of the present invention is shown in which ePTFE column 1900 includes a number of holes 1901A-1901D therethrough in which respective column filler elements (e.g., formed from an elastomer) are disposed (FIG. 19A is a top view and FIG. 19B is a side view). Of course, four holes are shown as an example only (which example is intended to be illustrative and not restrictive), and any desired number of holes may be used. Further, some or all of the holes may include the filler (e.g., some of the holes may be fully or partially empty). Of note, the embodiment of these FIGS. 19A and 19B differs from the embodiments of FIGS. 17A, 17B, 18A, 18B and 18C in that in these FIGS. 19A and 19B the holes are not directly up and down between the top and bottom of the ePTFE column 1900.

Of note, this single composite structure embodiment (which includes multiple holes for containing elastomer therein) may help prevent tissue and/or bone growth between discrete columns.

Of further note, this embodiment (which includes multiple holes for containing elastomer therein) may have one or more holes (e.g., vertically-oriented spaces, or lumens, running through the structure) of different sizes and shapes, each of which may be empty or filled (fully or partially) with an elastomeric material for purposes of adjustment of the behavior of the structure so as to mimic the behavior of the in vivo intervertebral disc in modes of bending, compression and torsion, and combinations thereof. It is believed that the placement of these lumens within the structure further allows for precise control of the structure in modes of bending, compression and torsion, and combinations thereof. As an additional means of control, the lumens may be filled (fully or partially) with an elastomeric material of one or more different elastic modulus.

Figure 20A:
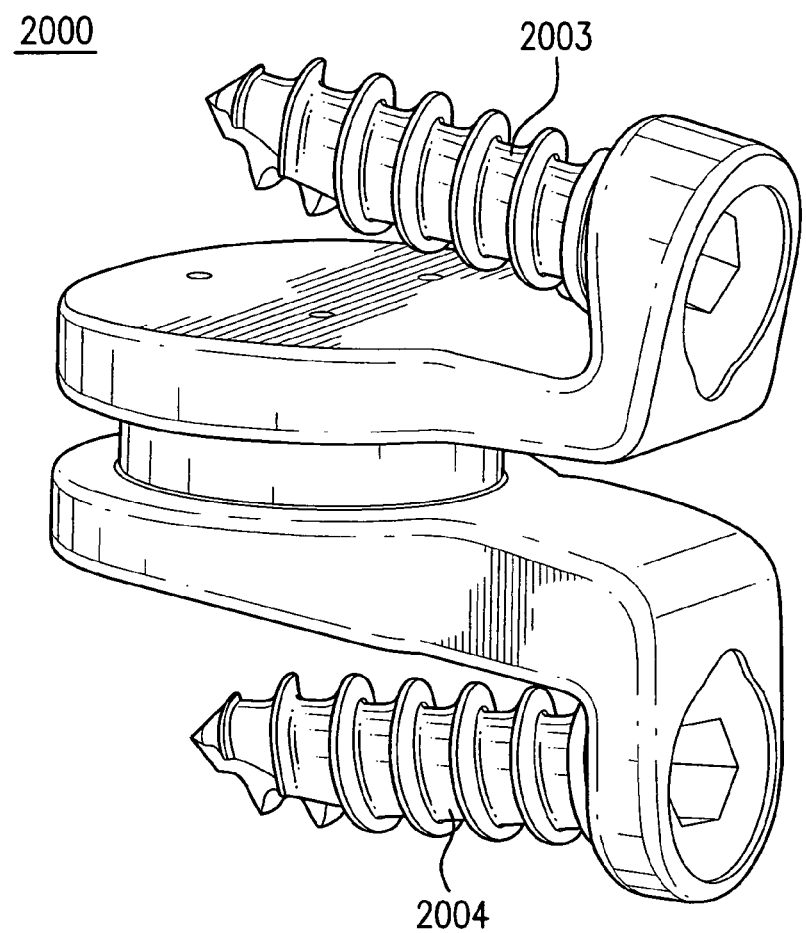
FIGS. 20A-20E show other embodiments of the present invention.
Figure 20B:
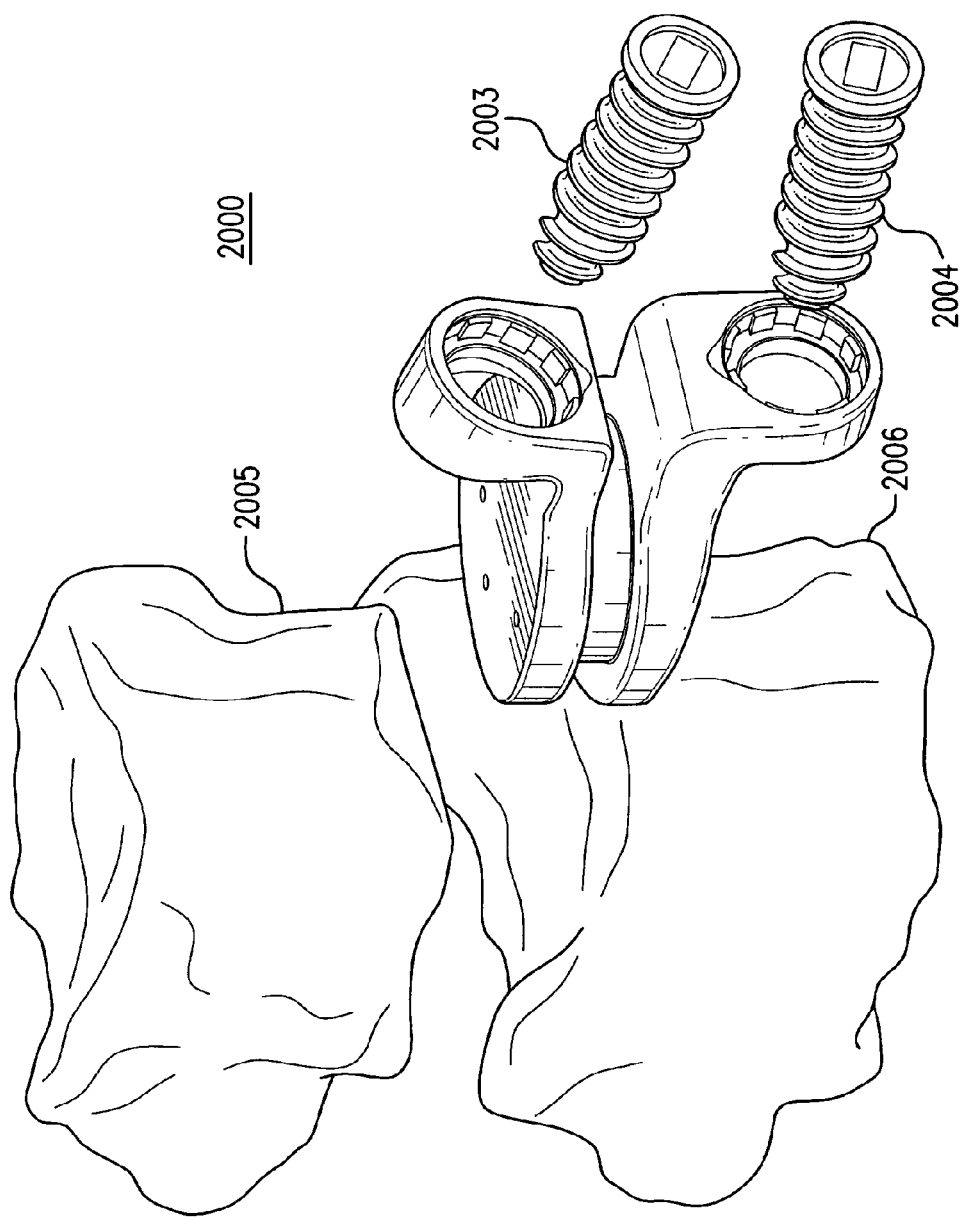
Figure 20C:
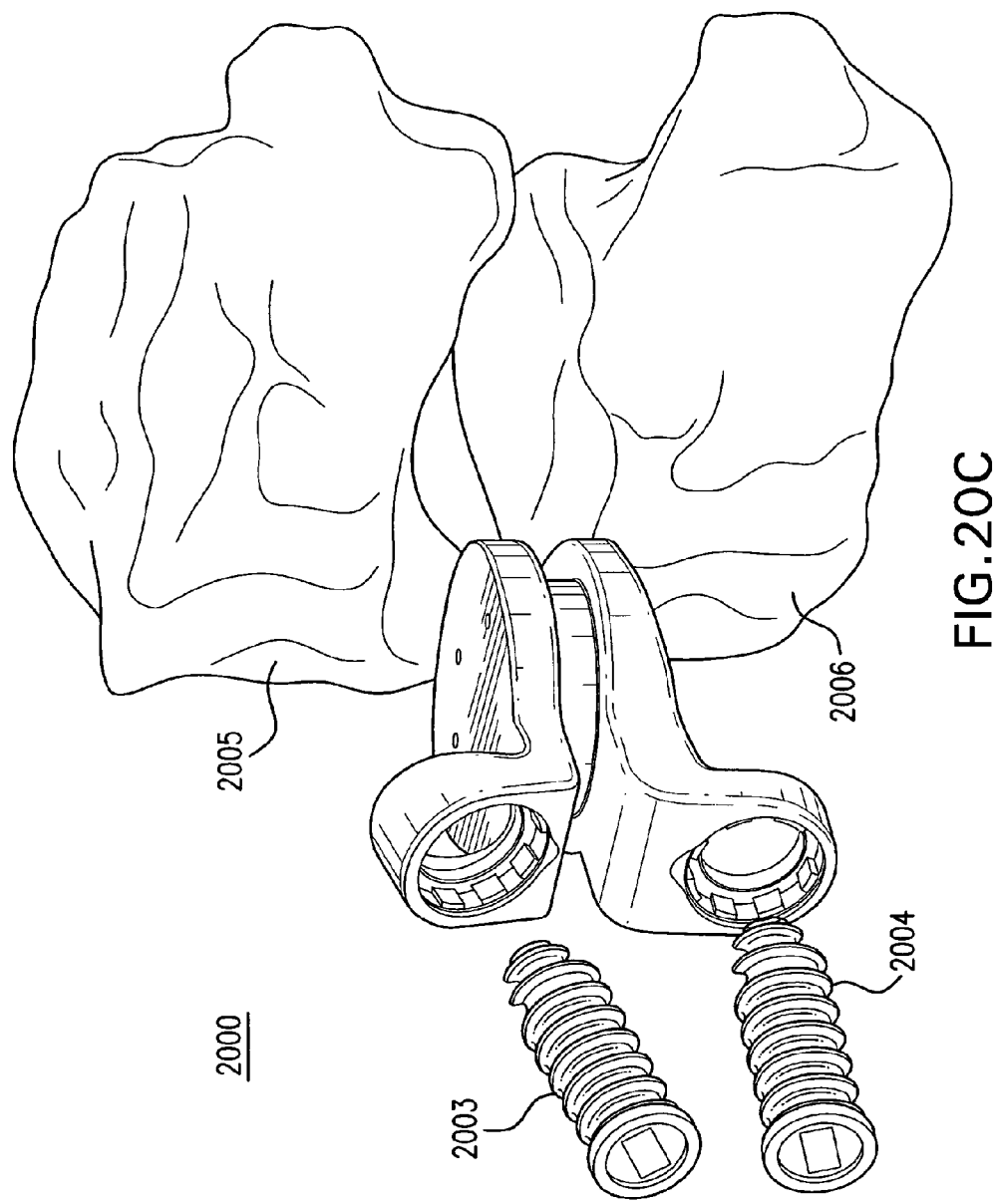
Figure 20D:
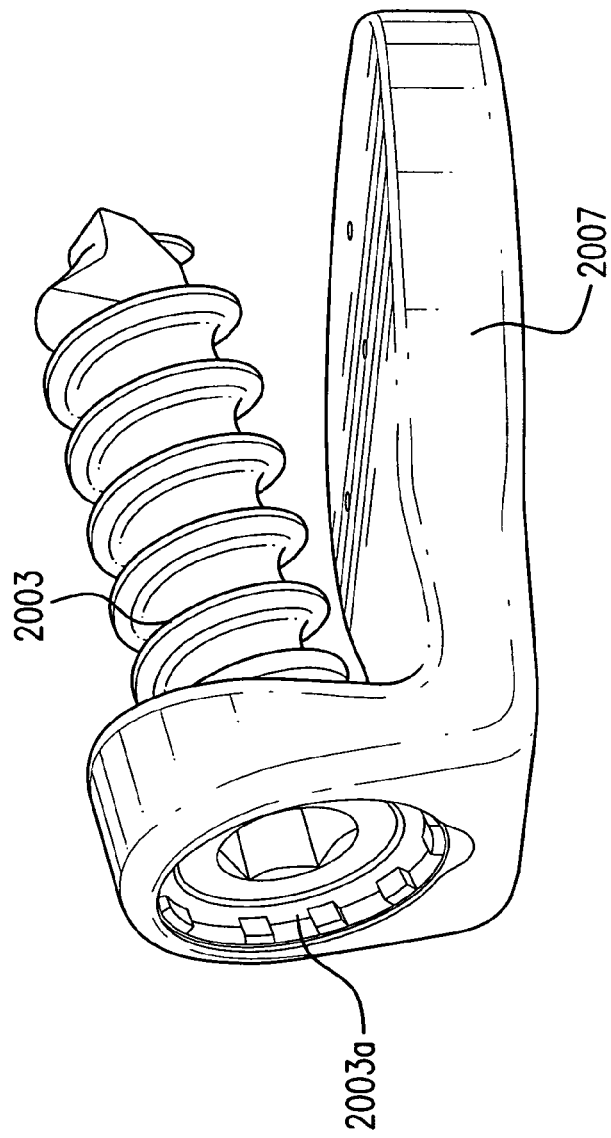
Figure 20E:
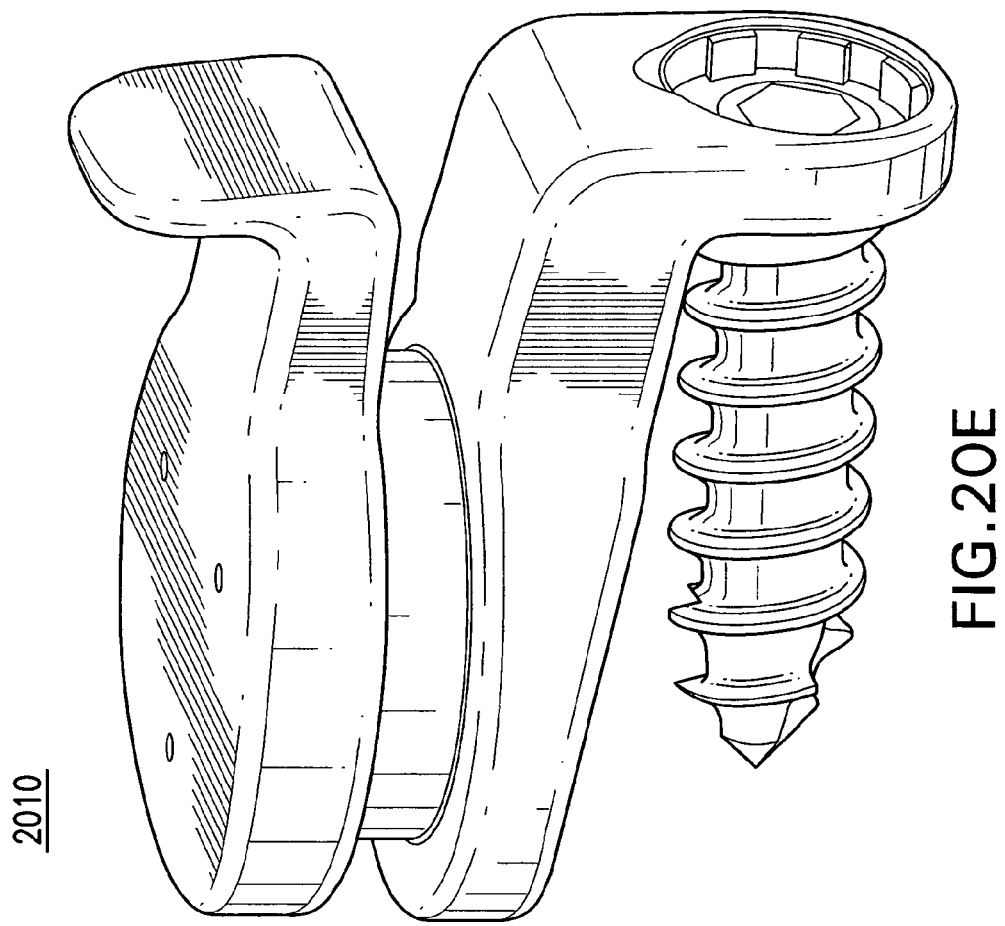

Referring now to FIGS. 20A-20E, exterior views of still further embodiments of the present invention are shown. More particularly, FIG. 20A shows a perspective view of AID assembly 2000 (this AID assembly 2000 utilizes two bone screws 2003 and 2004 for immediate fixation to the vertebrae); FIG. 20B shows an exploded perspective view of AID assembly 2000 along with vertebrae 2005 and 2006 (between which AID assembly 2000 would be placed); FIG. 20C shows an exploded perspective view of AID assembly 2000 along with vertebrae 2005 and 2006 (this view is similar to FIG. 20B, but from a different angle); FIG. 20D shows a closer perspective view of a portion of AID assembly 2000 of FIG. 20A (this view shows one anchor plate 2007 and associated bone screw 2003 and torque washer 2003a); and FIG. 20E shows a perspective view of AID assembly 2010 (which AID assembly 2010 utilizes only one bone screw).

Figure 21A:
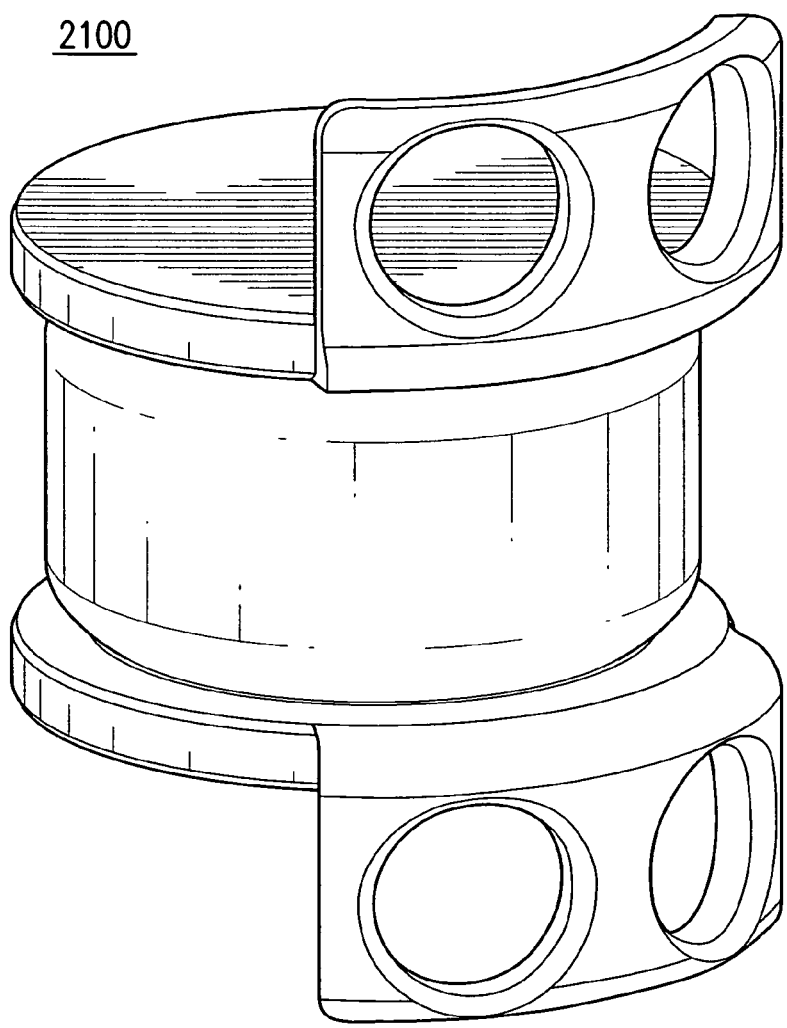
Figure 21B:
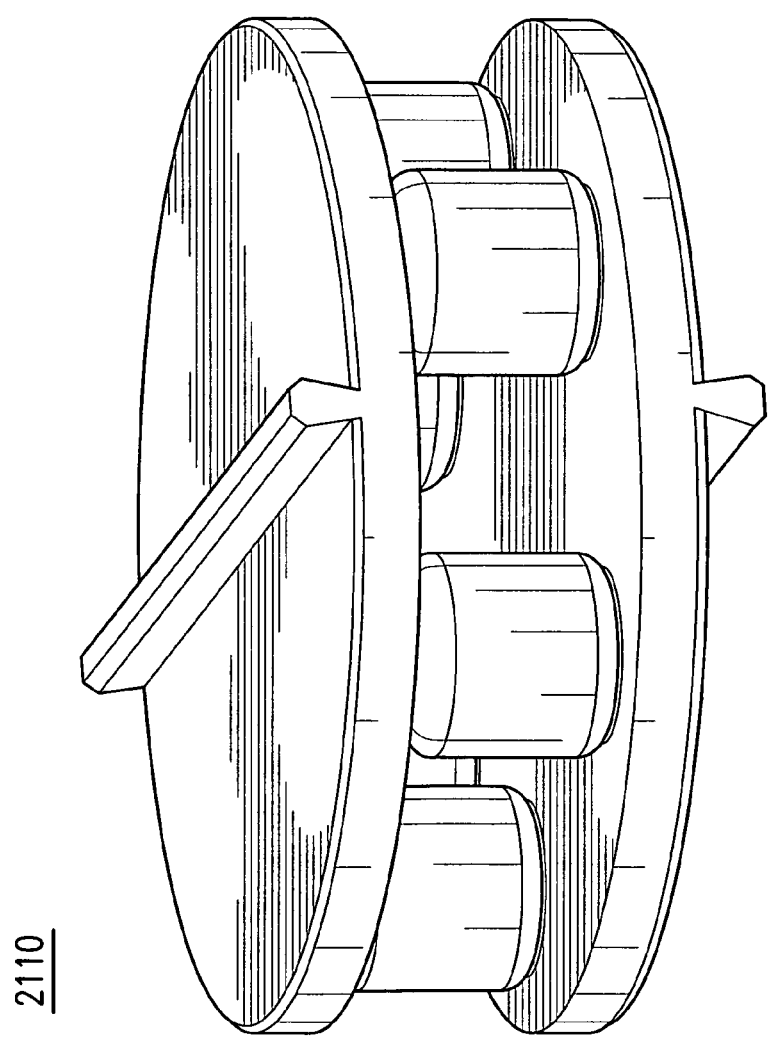
Figure 21C:
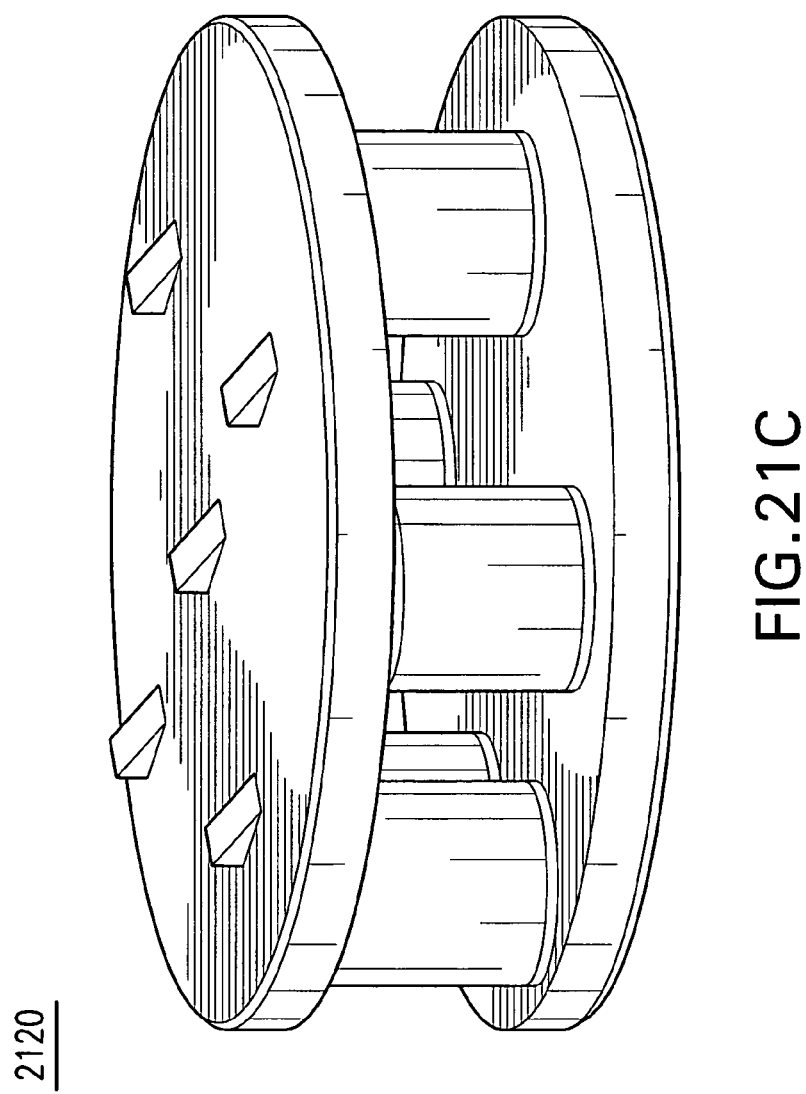

Referring now to FIGS. 21A-21C, exterior views of still further embodiments of the present invention are shown. More particularly, FIG. 21A shows a perspective view of anterior cervical AID assembly 2100 (this AID assembly 2100 utilizes four bone screws (not shown) for immediate fixation to the vertebrae); FIG. 21B shows a perspective view of anterior lumbar AID assembly 2110 (this AID assembly 2110 utilizes dovetail interfaces for immediate fixation to the vertebrae); and FIG. 21C shows a perspective view of anterior lumbar AID assembly 2120 (this AID assembly 2120 utilizes angled gripping elements for immediate fixation to the vertebrae).

Figure 22C:
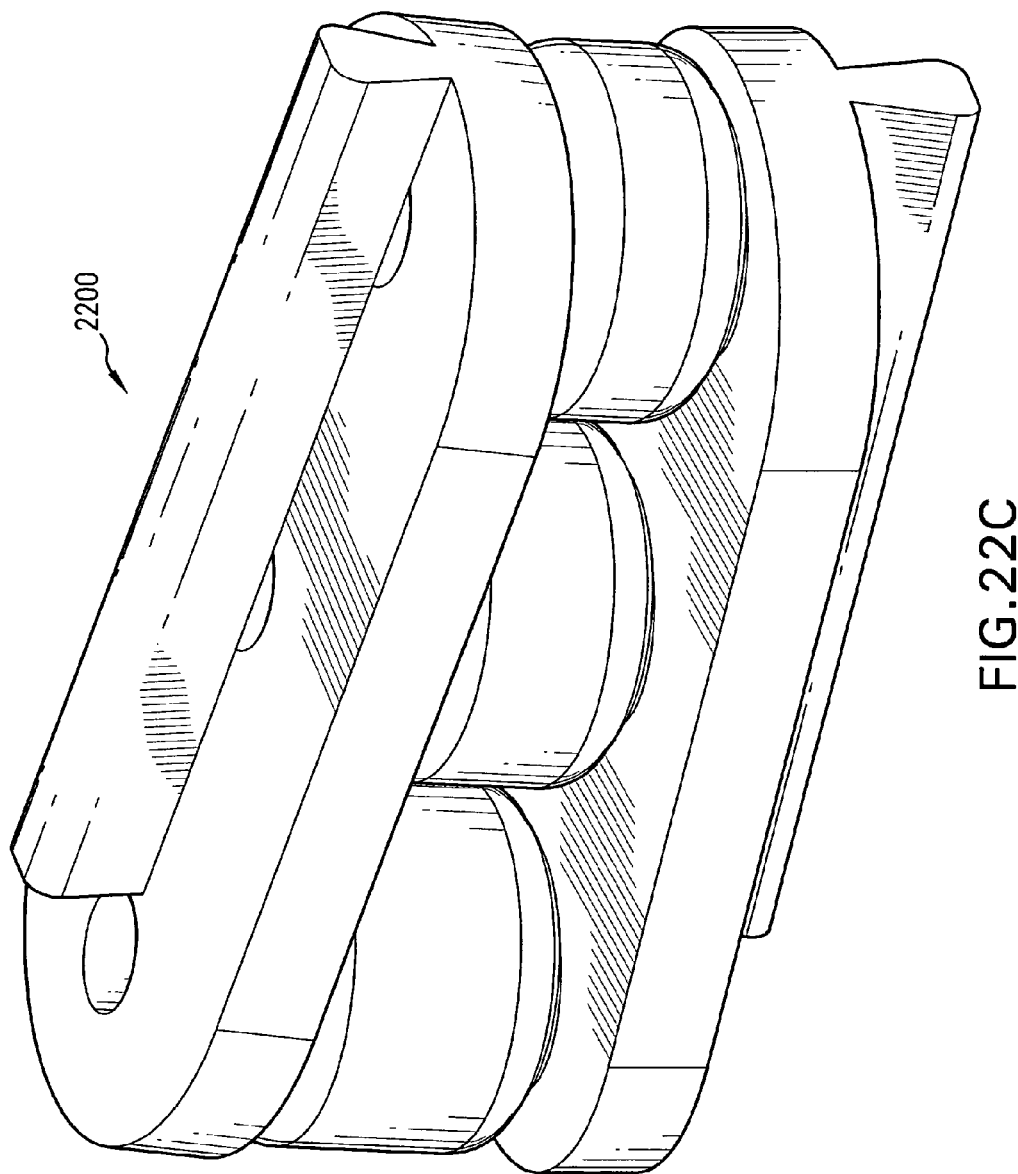
Figure 22D:
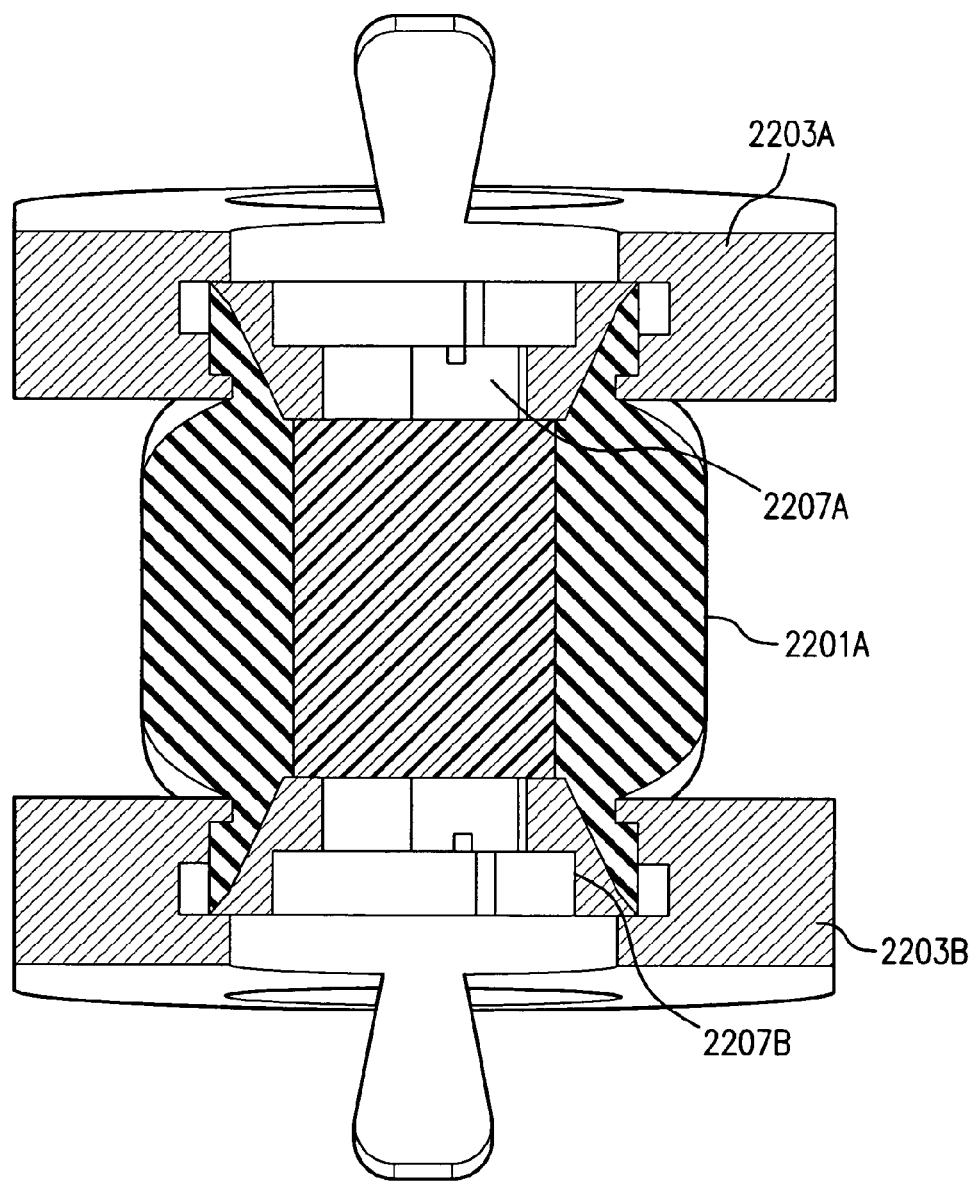
Figure 22E:
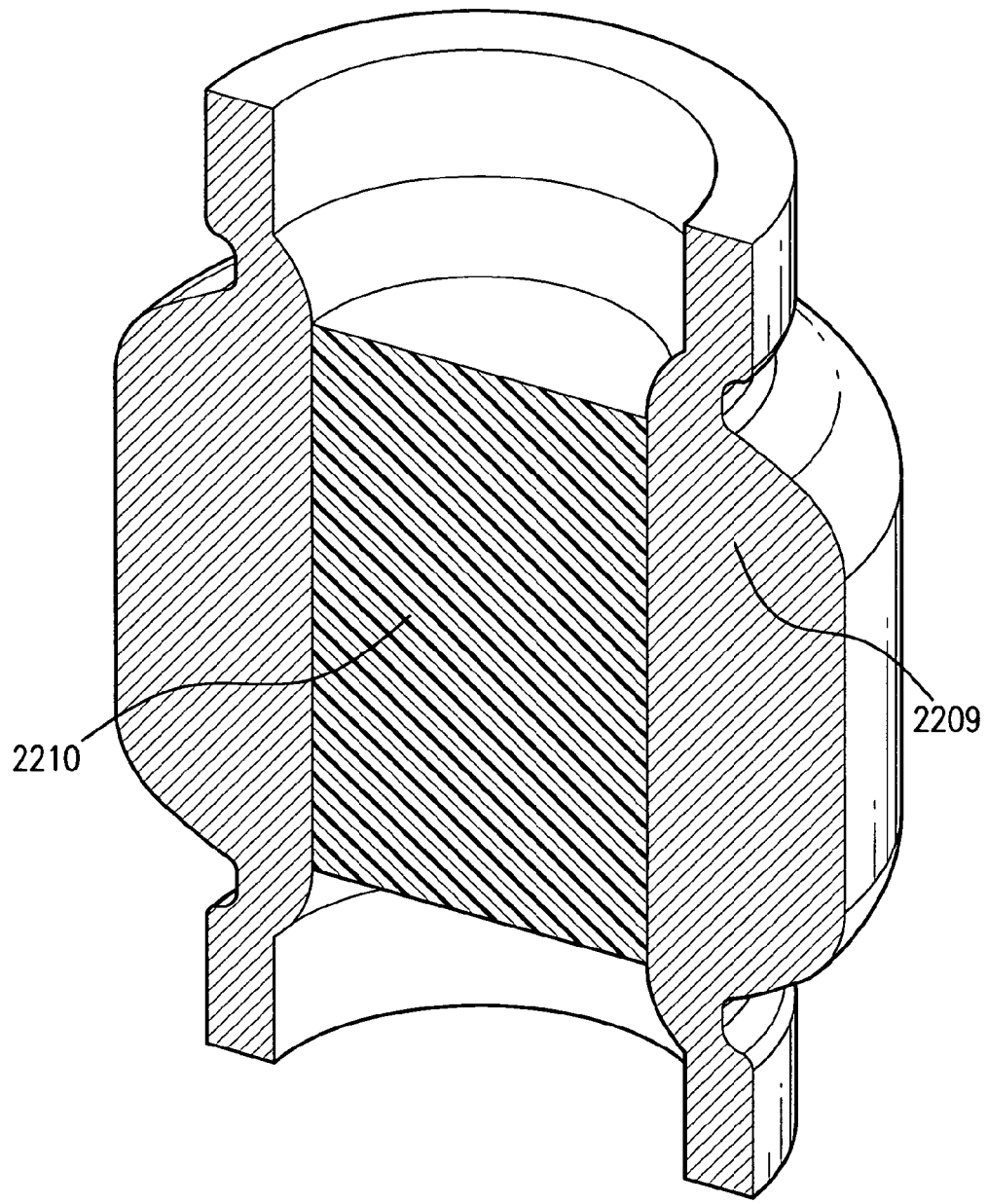

Referring now to FIGS. 22A-22C, views of still further embodiments of the present invention are shown. More particularly, FIG. 22A shows a side view of AID assembly 2200 (this AID assembly 2200 utilizes an essentially linear line of three composite structures 2201A-2201C mounted to anchor plates 2003A and 2203B; FIG. 22B shows another view of AID assembly 2200 of FIG. 22A (the dovetail interfaces 2205A and 2205B for immediate fixation to the vertebrae are shown more clearly in this view); FIG. 22C shows a perspective view of AID assembly 2200 of FIGS. 22A and 22B; FIG. 22D is a cross-sectional view of AID assembly 2200 as shown in FIG. 22B (as seen in this FIG. 22D, a connection between anchor plate 2003A and a composite structure is shown using screw in ferrule 2207A and a connection between anchor plate 2003B and the composite structure is shown using screw in ferrule 2207B; and FIG. 22E shows a cross-sectional view of a composite structure (showing column (e.g., ePTFE column) 2209 and column filler (e.g., thermoplastic polyurethane core) 2210).

Figure 23A:
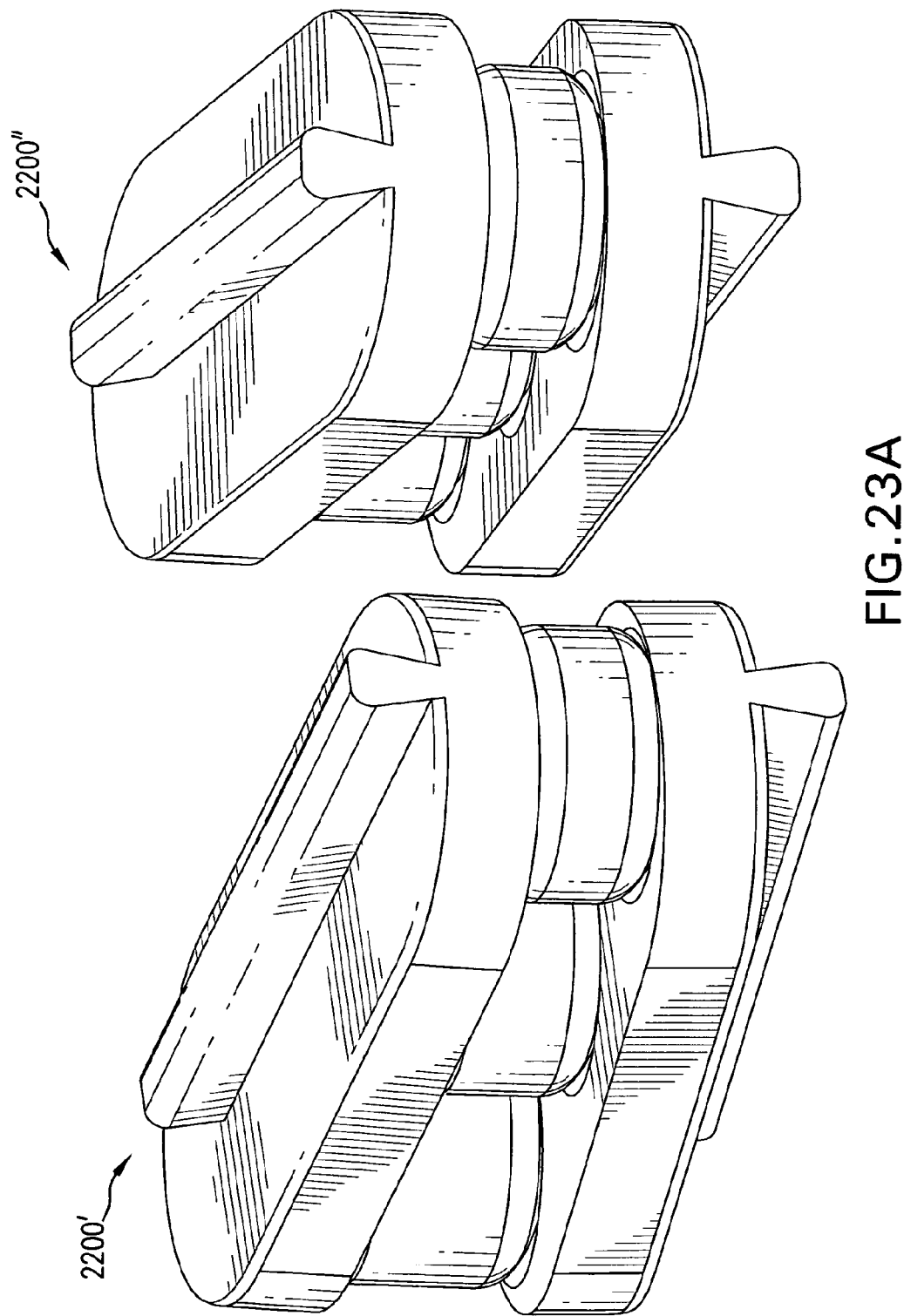
FIGS. 23A and 23B show other embodiments of the present invention.
Figure 23B:
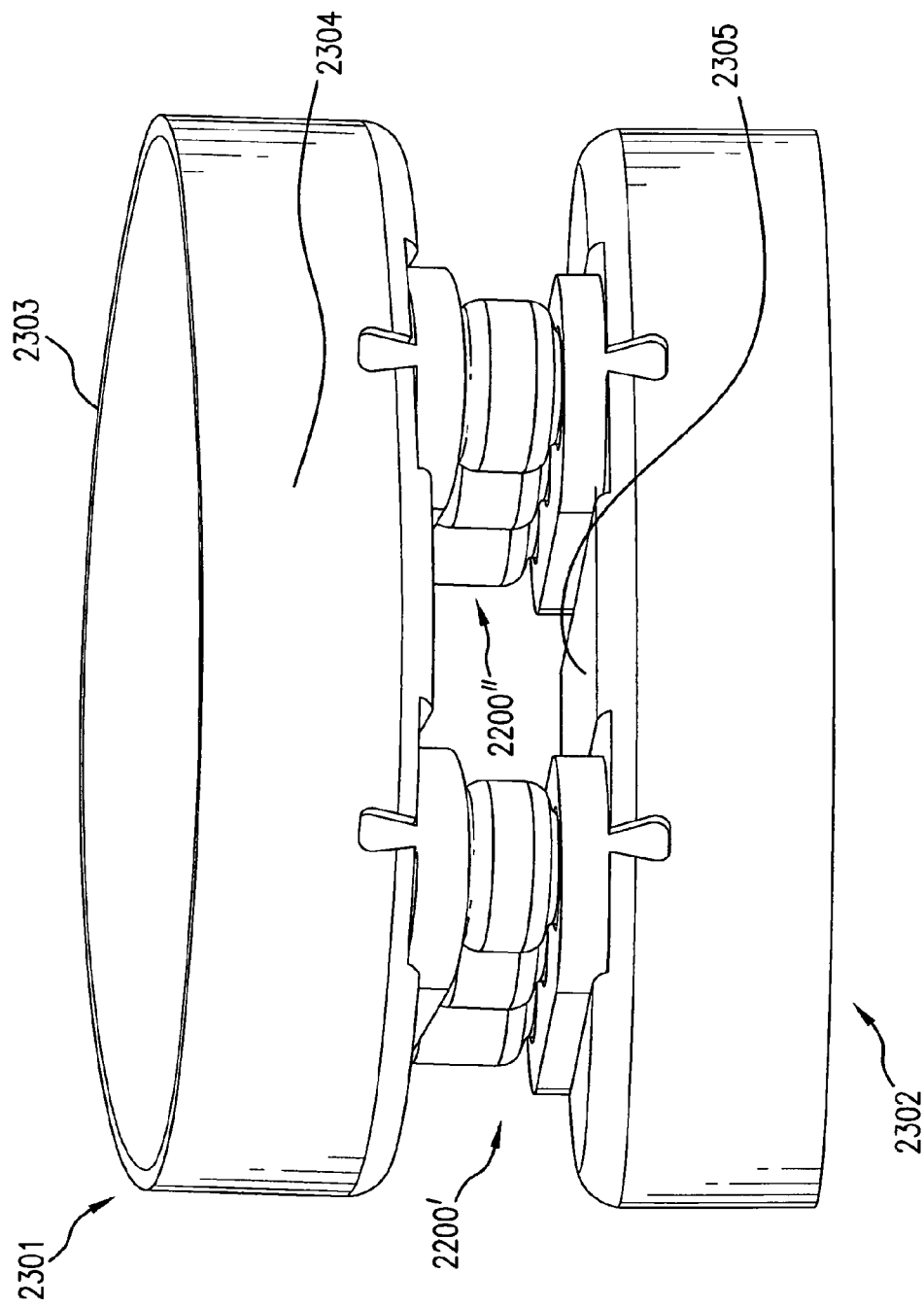

Referring now to FIGS. 23A and 23B, views of two of the AID assemblies of FIGS. 22A-22D are shown. More particularly, FIG. 23A shows a perspective view of posterior lumbar AID assembly 2200' and 2200"; and FIG. 23B shows a perspective view of posterior lumbar AID assembly 2200' and 2200" implanted between vertebra 2301 and 2302 (2303 represents cancellous bone; 2304 represents cortical shell; and 2305 represents vertebral endplate).

Figure 24:
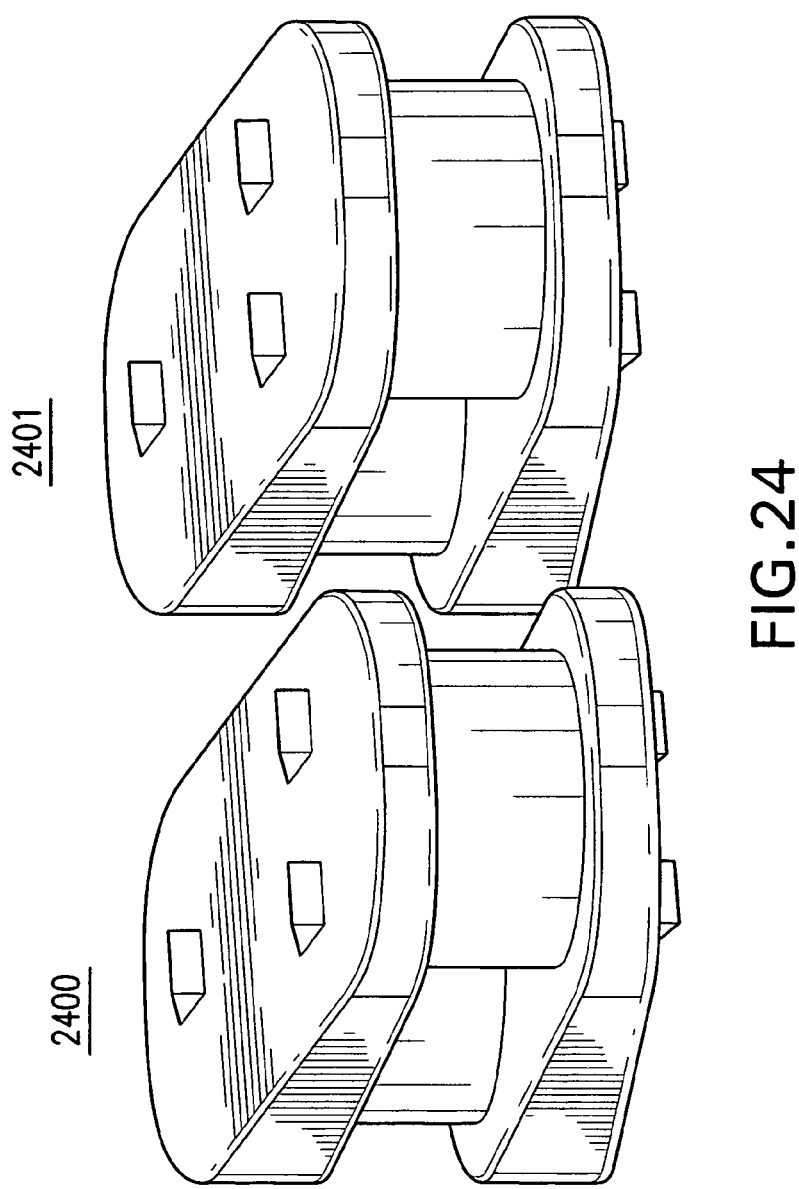
FIG. 24 shows another embodiment of the present invention.

Referring now to FIG. 24, a view of a still further embodiment of the present invention is shown. More particularly, FIG. 24 shows a perspective view of posterior lumbar AID assemblies 2400 and 2401 (angled protrusions aid in immediate fixation to the vertebrae).

Figure 25C:
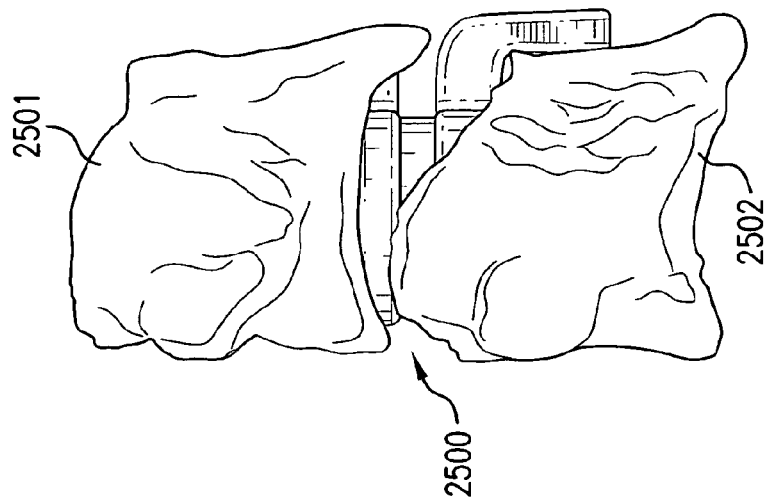
FIGS. 25A-25C and 26A-26C show other embodiments of the present invention.
Figure 25B:
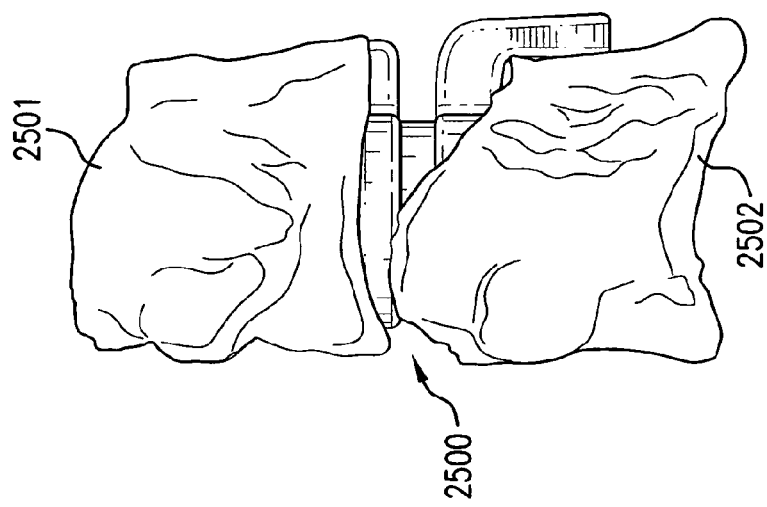
Figure 25A:
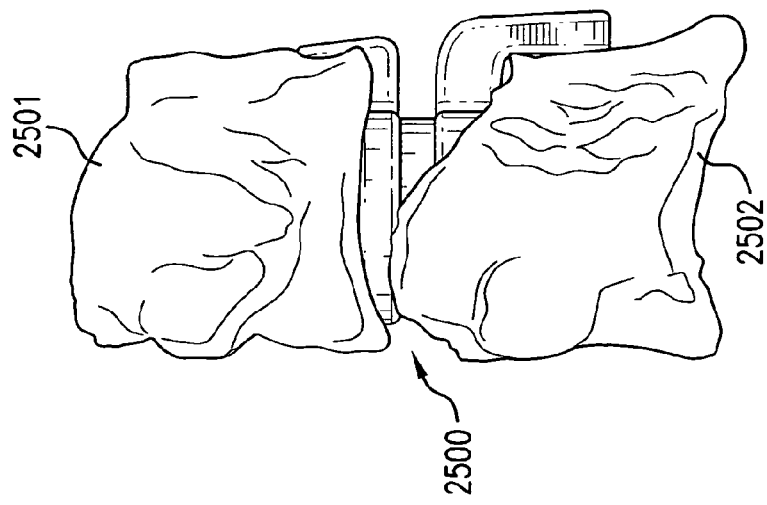
Figure 26A:
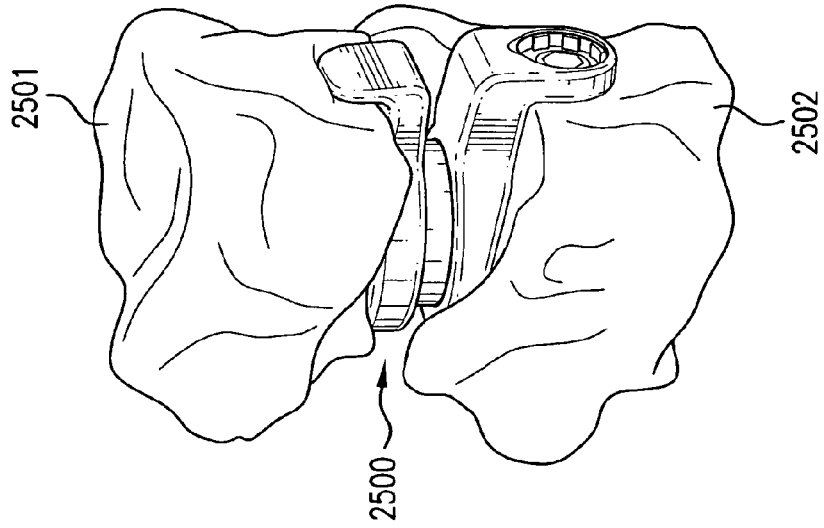
Figure 26B:
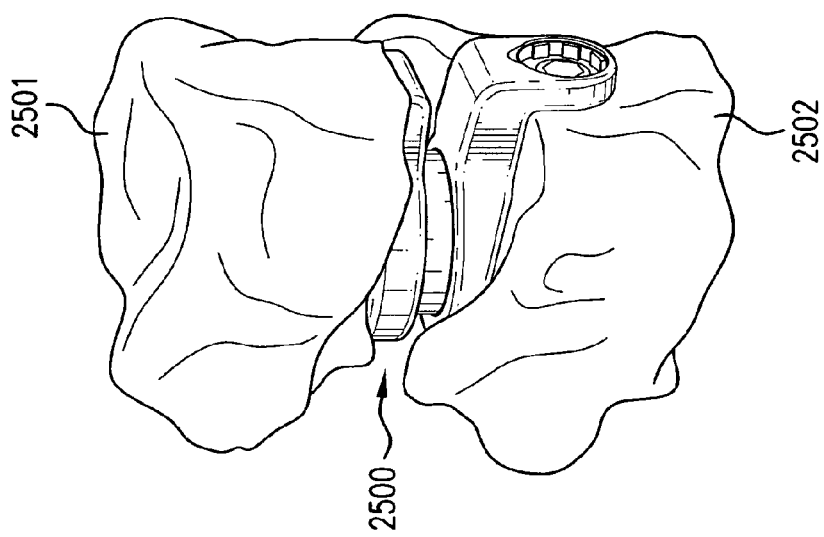
Figure 26C:
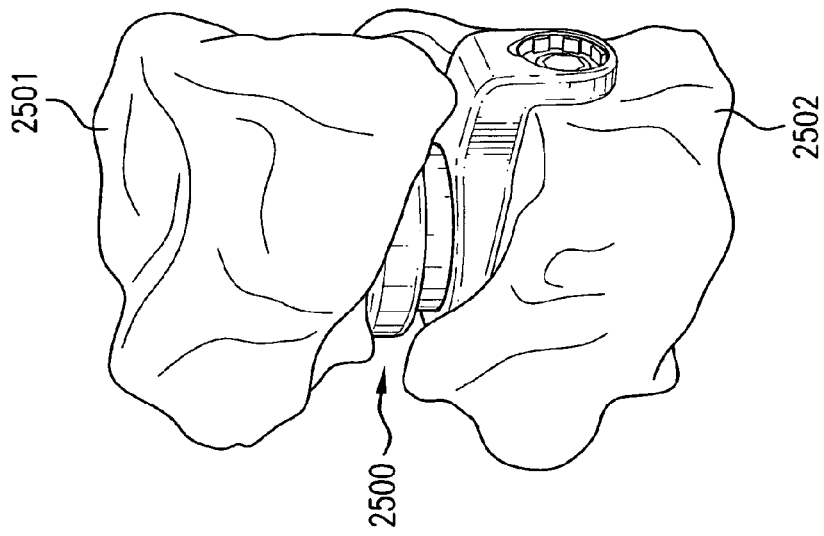

Referring now to FIGS. 25A-25C and 26A-26C, various views AID assembly 2500 implanted between vertebrae 2501 and 2502 are shown. More particularly, FIGS. 25A and 26A show, respectively, side and perspective views of the AID assembly as initially implanted between the vertebrae; FIGS. 25B and 26B show, respectively, side and perspective views of the AID assembly as implanted between the vertebrae at a later time and as being partially overgrown by bone growth; and FIGS. 25C and 26C show, respectively, side and perspective views of the AID assembly as implanted between the vertebrae at a still later time and as being more overgrown by bone growth.

Figure 27:
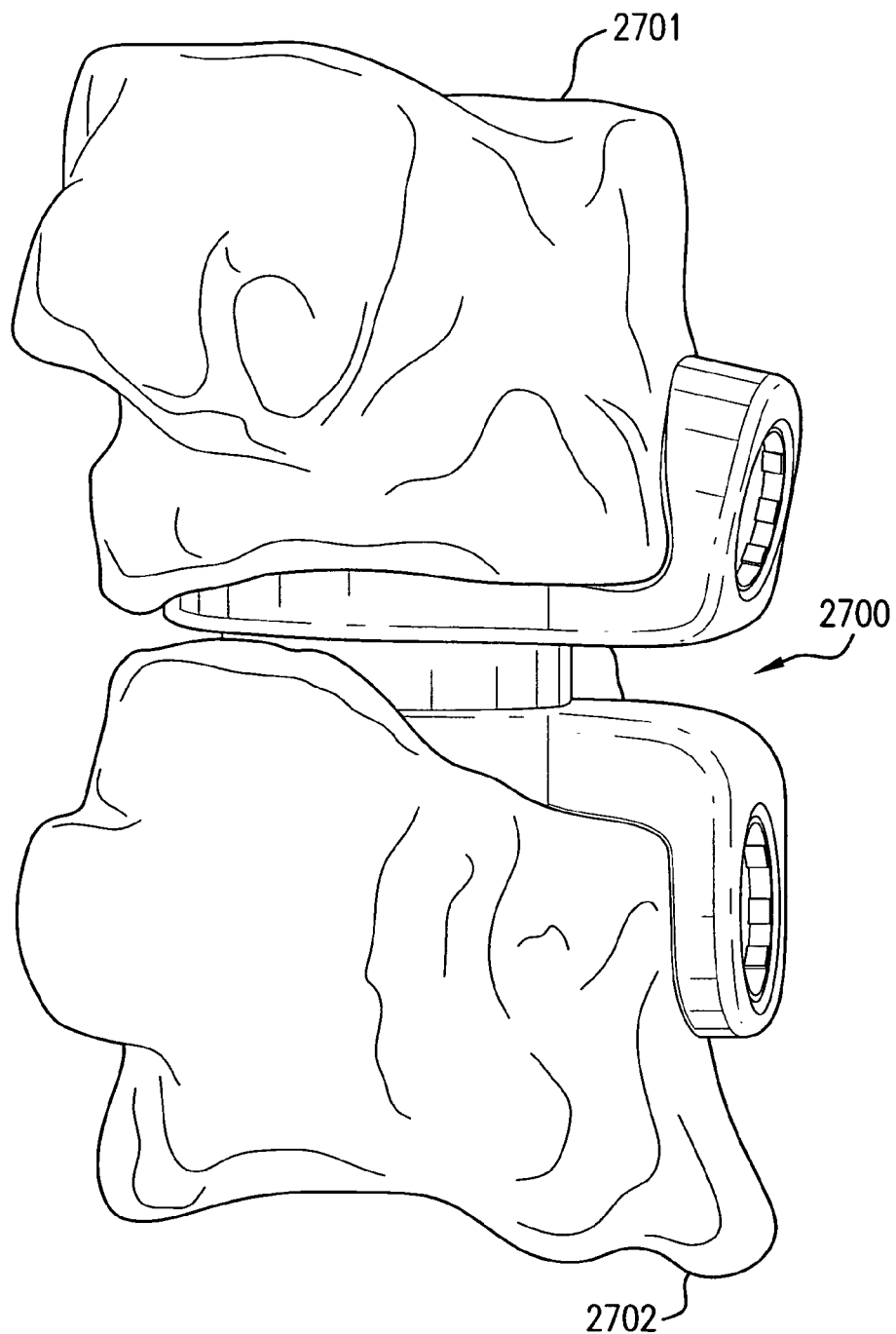
FIG. 27 shows another embodiment of the present invention.

Referring now to FIG. 27, a view of a still further embodiment of the present invention is shown. More particularly, FIG. 27 shows a perspective view of AID assembly 2700 implanted between vertebrae 2701 and 2702.

Figure 28A:
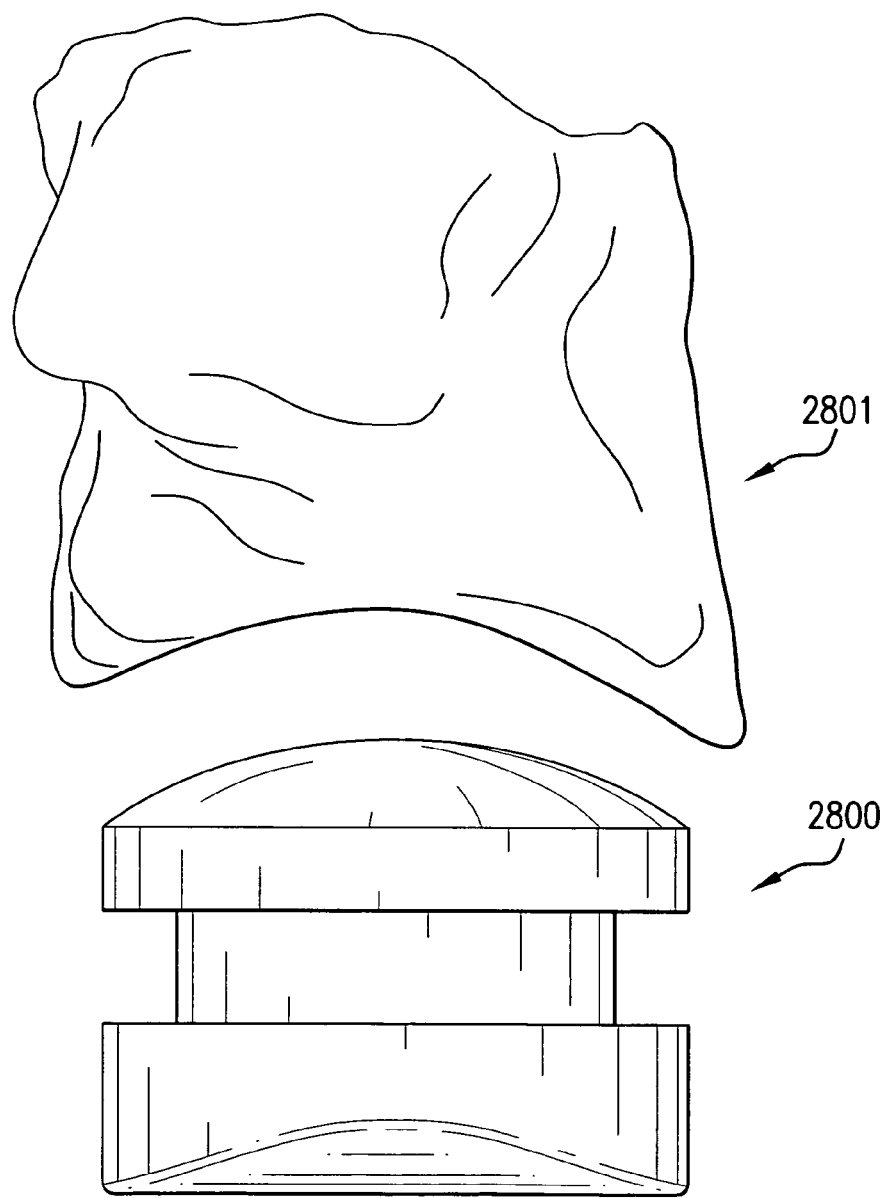
FIGS. 28A and 28B show other embodiments of the present invention.
Figure 28B:
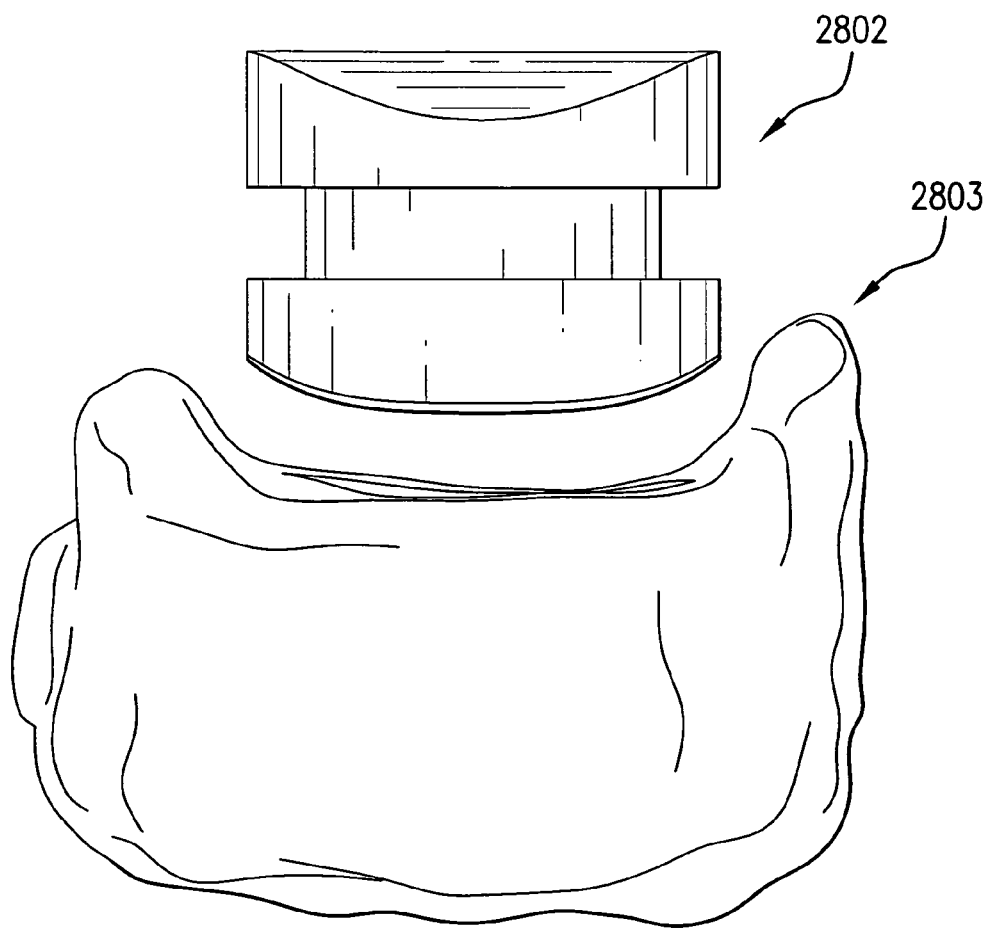

Referring now to FIGS. 28A and 28B, views of still further embodiments of the present invention are shown. More particularly, FIG. 28A shows a cephalad shape match between a vertebra interface portion of AID assembly 2800 and vertebra 2801; and FIG. 28B shows a caudad shape match between a vertebra interface portion of AID assembly 2802 and vertebra 2803.

Figure 29A:
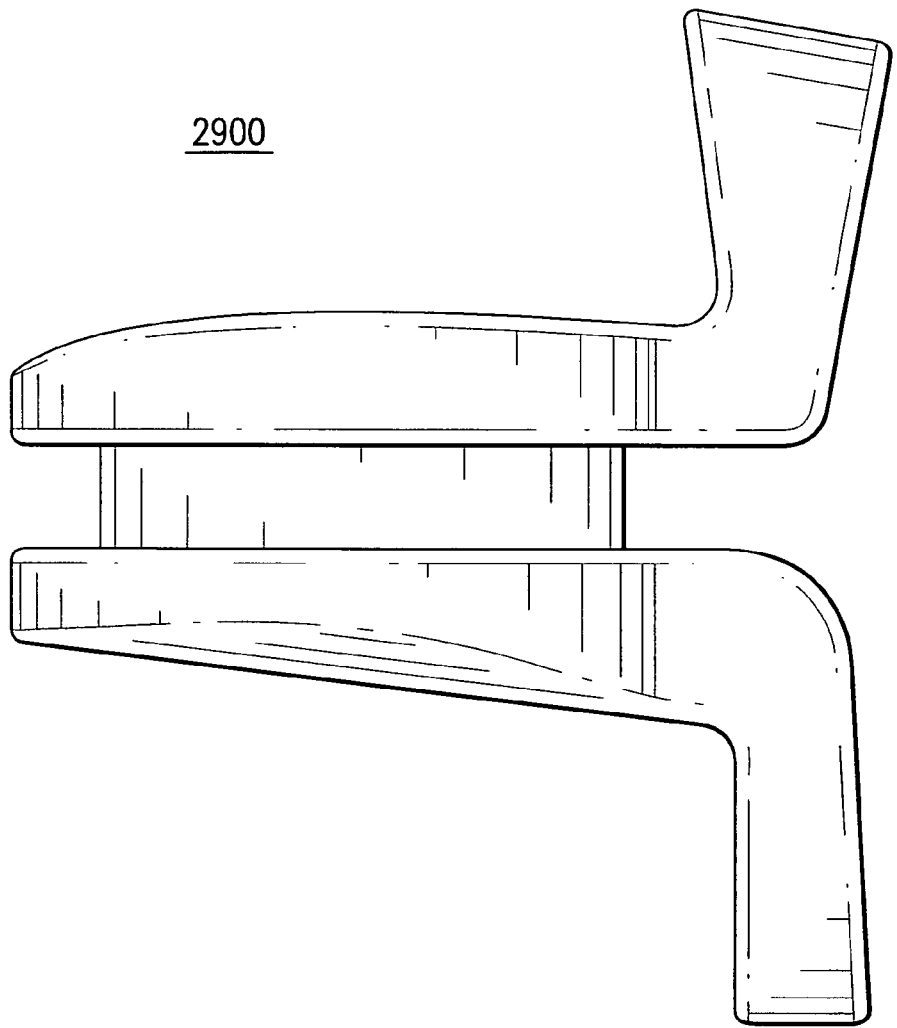
FIGS. 29A and 29B show other embodiments of the present invention.
Figure 29B:
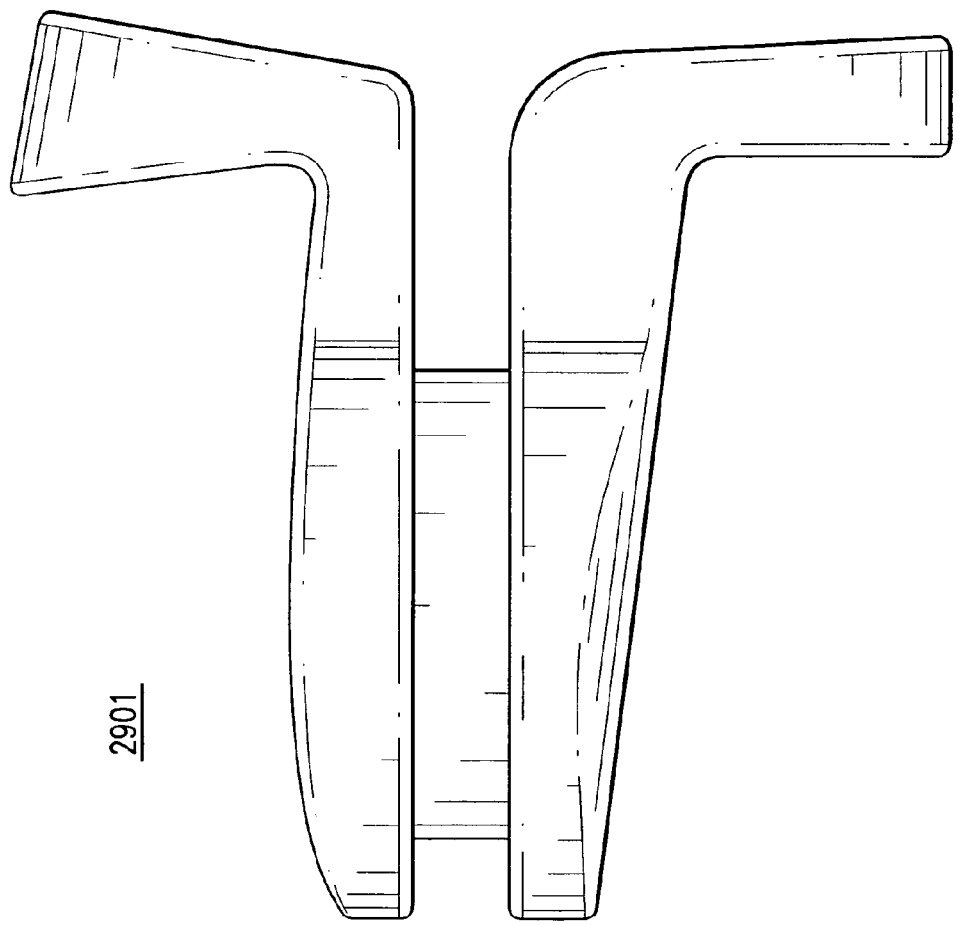

Referring now to FIGS. 29A and 29B, views of still further embodiments of the present invention are shown. More particularly, FIG. 29A shows AID assembly 2900 (having a relatively short A-P dimension); and FIG. 29B shows AID assembly 2901 (having a relatively long A-P dimension).

Figure 30A:
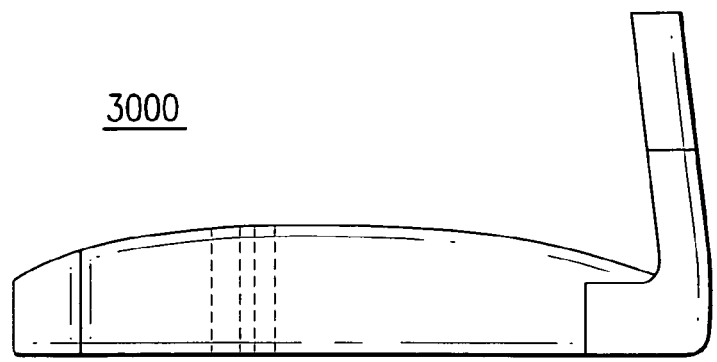
FIGS. 30A-30C show other embodiments of the present invention.
Figure 30B:
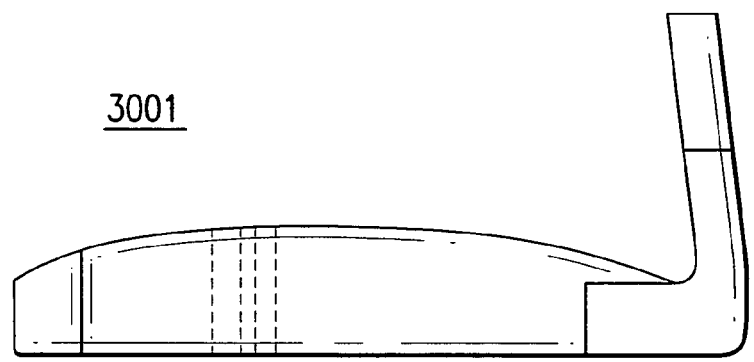
Figure 30C:
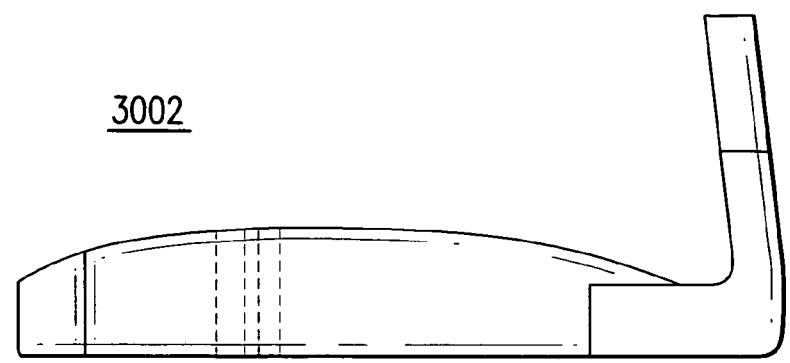

Referring now to FIGS. 30A-30C, views of still further embodiments of the present invention are shown. More particularly, FIG. 30A shows AID assembly 3000 (having a relatively short A-P dimension); and FIG. 30B shows AID assembly 3001 (having a medium length A-P dimension); and FIG. 30C shows AID assembly 3002 (having a relatively long A-P dimension).

Figure 31B:
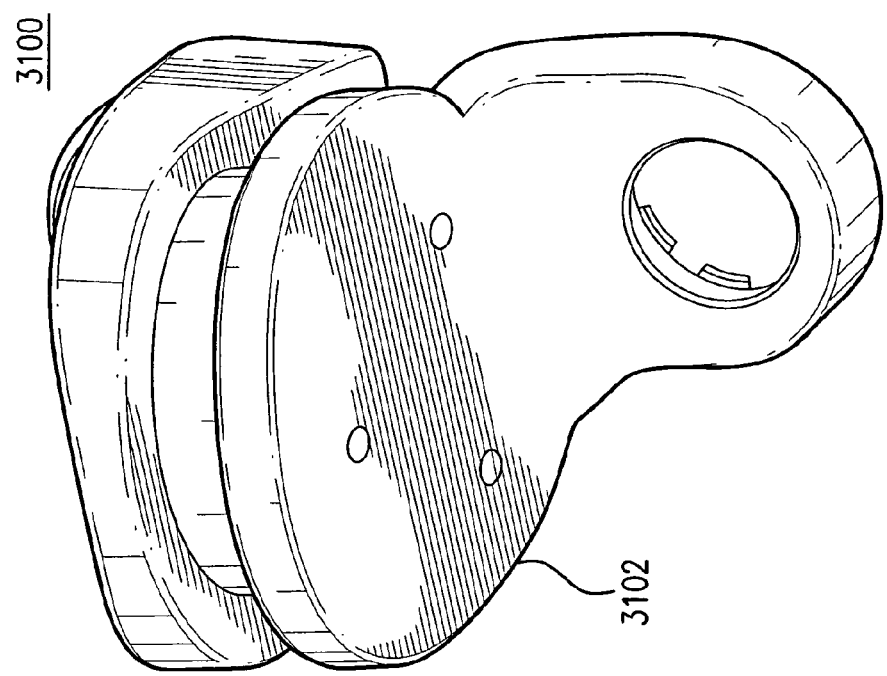
FIGS. 31A-31C show other embodiments of the present invention.
Figure 31A:
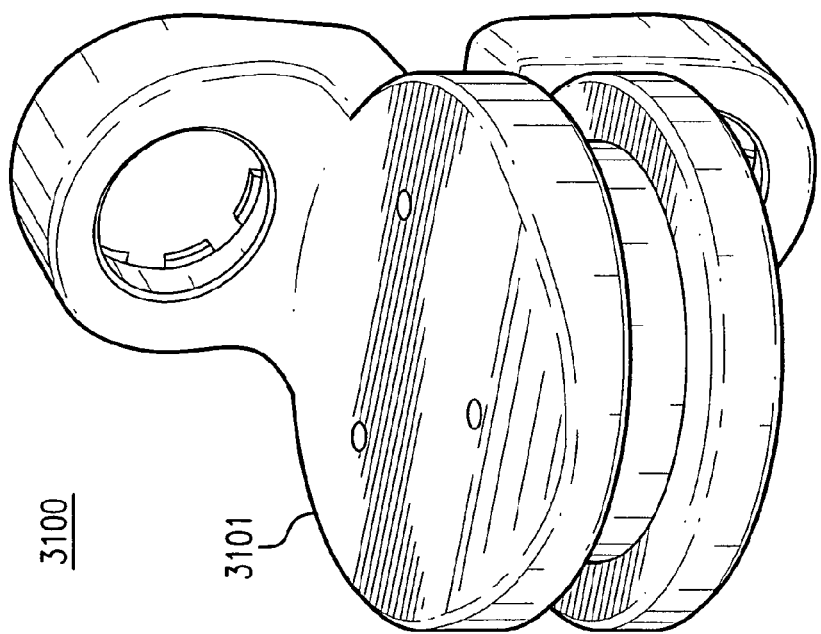
Figure 31C:
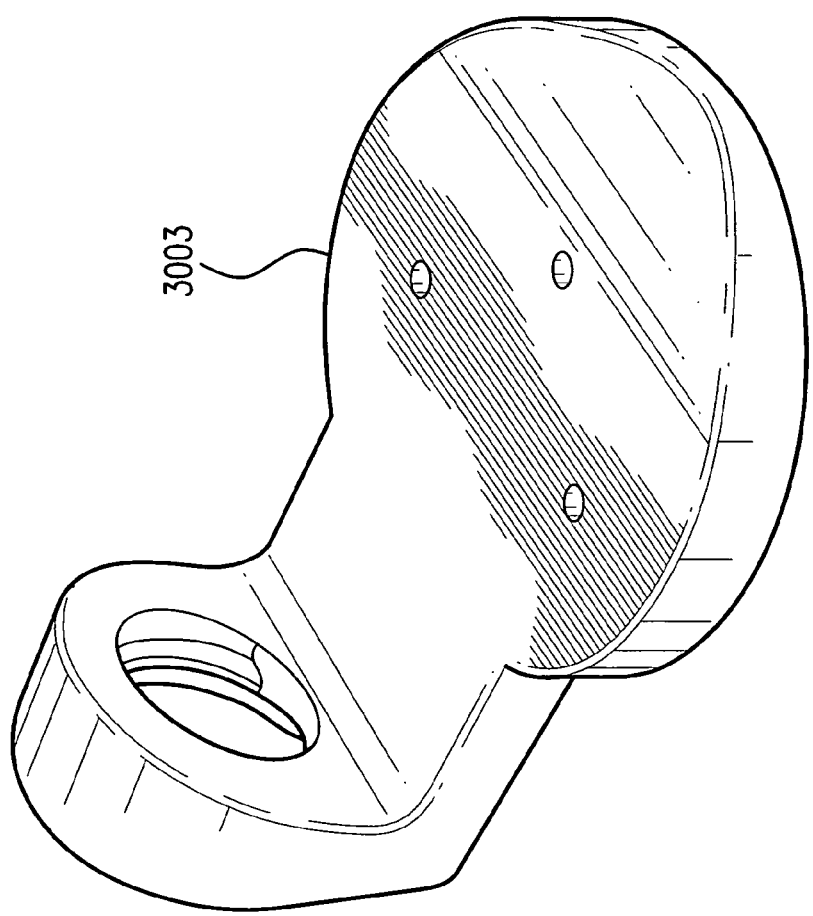

Referring now to FIGS. 31A-31C, views of still further embodiments of the present invention are shown. More particularly, FIG. 31A shows AID assembly 3100 (surface treatment 3001 at an anchor plate/vertebra interface is seen in this Figure); FIG. 31B shows AID assembly 3100 (surface treatment 3002 at an anchor plate/vertebra interface is seen in this Figure); and FIG. 31C shows one anchor plate of an AID assembly (surface treatment 3003 at an anchor plate/vertebra interface is seen in this Figure).

Figure 32B:
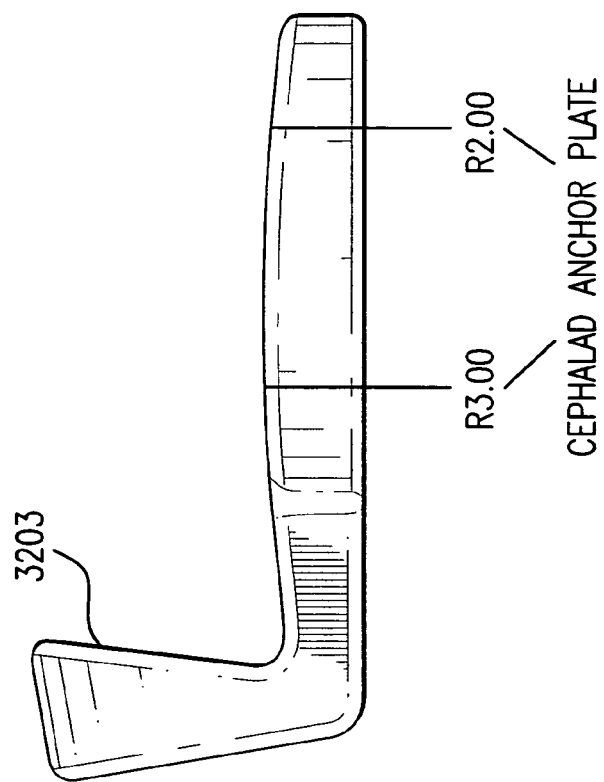
FIGS. 32A and 32B show other embodiments of the present invention.
Figure 32A:
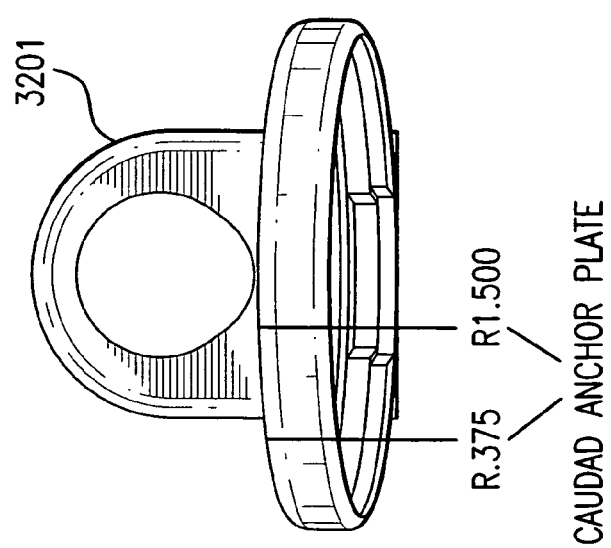

Referring now to FIGS. 32A and 32B, views of still further embodiments of the present invention are shown. More particularly, FIG. 32A shows example radii associated with a bone-contacting surface of Caudad Anchor Plate 3201 and FIG. 32B shows example radii associated with a bone-contacting surface of Cephalad Anchor Plate 3203.

Figure 33A:
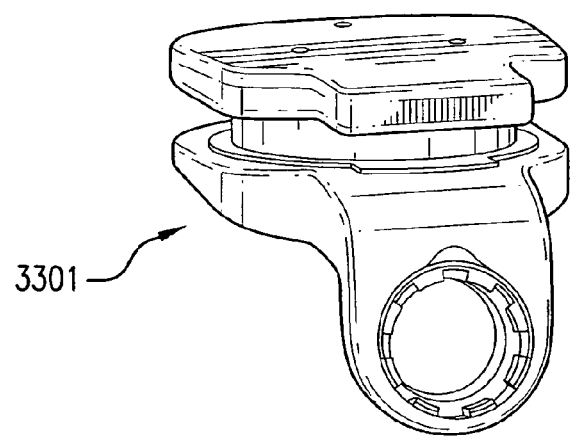
FIGS. 33A-33C show other embodiments of the present invention.
Figure 33B:
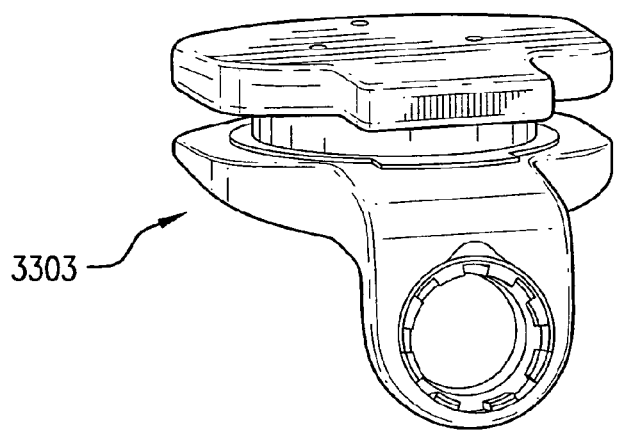
Figure 33C:
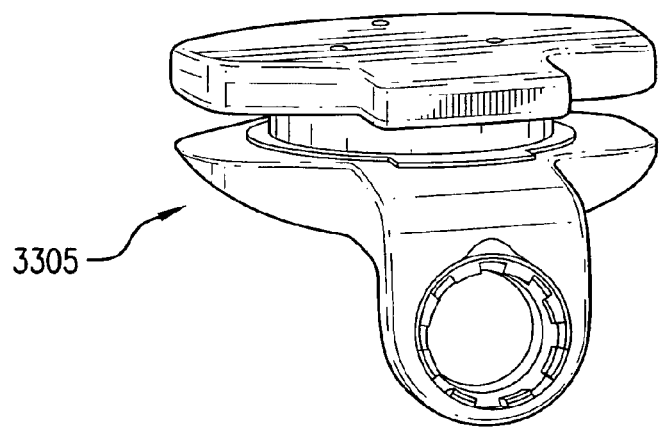

Referring now to FIGS. 33A-33C, views of still further embodiments of the present invention are shown. More particularly, these figures show that the AID may come variety of 'widths'. For example, FIG. 33A shows AID assembly 3301 having a "narrow" width, FIG. 33B shows AID assembly 333 having a "regular" width and FIG. 3CA shows AID assembly 3305 having a "wide" wide.

Of note, such multiple "widths" (and/or multiple "lengths", as described above) could provide the potential for the greatest amount of surface contact between the device and the vertebral endplate, thus lowering the contact stresses and reducing the potential for subsidence (gradual "sinking" of the device into the adjoining vertebral bodies).

Additionally, it is noted that during the surgical preparation of the vertebral endplate, a surgeon may scrape/score the bony surface in order to promote bone growth with the intention of securing ultimate fixation between vertebra and implant. If the scraped/scored surface is larger than the implanted device, there is a greater likelihood of bone growing up around the perimeter of the device, eventually causing bone bridging, fusing the spinal segment. A device with a surface that better matches the prepared endplate in terms of area coverage may help discourage this behavior.

In another embodiment the column (which may be formed of ePTFE or any other desired material) may be an essentially solid chord or piece of material.

In another embodiment the column (which may be formed of ePTFE and/or any other desired material(s)) may be an essentially solid combination of materials.

In another embodiment the ePTFE may be provided with non-expanded regions, such as at the anchoring regions, for example.

In another embodiment a column (e.g., formed of ePTFE) could be extruded to have greater wall thickness on one side or end as opposed to another side or end. For example (which example is intended to be illustrative and not restrictive), the walls of the anterior side may be extruded thicker than the walls of the posterior side.

In another embodiment the AID assembly may be customized to provide any desired articulation, kinematic behavior, dynamic behavior and/or static properties for any given application (e.g., implantation site) and/or patient (e.g., gender, age, height, weight, activity level). For example (which examples are intended to be illustrative and not restrictive):

1. The articulation, kinematic behavior, dynamic behavior and/or static properties exhibited by the column(s) may be modified by varying the density of the nodes of the ePTFE.
2. The articulation, kinematic behavior, dynamic behavior and/or static properties exhibited by the column filler (e.g., elastomer) may be modified by varying the density and/or composition of the elastomer.
3. The articulation, kinematic behavior, dynamic behavior and/or static properties exhibited by the AID assembly may be modified by varying (for individual components (e.g., ePTFE column, column filler, intermediate elements, anchor plates)):
    a) column height;
    b) column width (e.g., diameter);
    c) column cross-section (shape and/or area);
    d) column wall thickness;
    e) column stiffness modulus;
    f) filler height;
    g) filler width (e.g., diameter);
    h) filler cross-section (shape and/or area);
    i) filler stiffness modulus;
    j) anchor plate material;
    k) anchor plate shape;
    l) anchor plate stiffness modulus;
    m) intermediate element material
    n) shape (e.g., curvature) of an interface between the filler and an anchor plate or intermediate element
4. The articulation, kinematic behavior, dynamic behavior and/or static properties exhibited one or more composite structures in a multiple composite structure AID assembly may be modified by varying one or more parameters discussed at paragraph 3, above, to render one or more of the composite structures stiffer than one or more of the other composite structures in order to add stiffness locally and to aid in mimicry of in vivo non-homogeneous stiffness topography (e.g., the in vivo topography relating to the area of relatively higher stiffness in the posterior region of the vertebral body versus the relatively lower stiffness in the anterior region of the vertebral body).
5. In the context of a multiple composite structure AID assembly, one or more of the composite structures may be positioned appropriately between the anchor plates as follows:
    a) one or more composite structures may be placed an increased distance from the center of the implant (e.g., to aid in increasing torsional stiffness of the implant);
    b) lateral positioning of one or more composite structures may be used (e.g., to aid in controlling lateral bending stiffness of the implant); and/or c) fore/aft positioning of one or more composite structures may be used (e.g., to aid in controlling flexion/extension stiffness of the implant).

6. In the context of a multiple composite structure AID assembly, any desired number of composite structures may be utilized.

7. In the context of a multiple hole composite structure, the articulation, kinematic behavior, dynamic behavior and/or static properties exhibited may be controlled in a similar manner as discussed at paragraphs 4-6, above, with regard to the multiple composite structure AID (e.g., the spacing between the holes may be varied, the size/cross-sectional area/cross-sectional shape of the holes may be varied, the position of the various holes may be varied, the number of holes may be varied etc.).

In another embodiment an artificial intervertebral disc is provided, comprising: a first anchor member; a second anchor member; and a composite structure disposed between the first anchor member and the second anchor member, which composite structure is comprised of a column formed of ePTFE and a column filler formed of an elastomer.

In one example the composite structure may be configured such that the composite structure has associated therewith, in at least one axis, a load versus deflection behavior substantially similar to that of a substantially healthy human intervertebral disc.

In another example the load versus deflection behavior may be selected from the group including (but not limited to): (a) dynamic behavior, which dynamic behavior is a function of a time rate application of load; (b) kinematic behavior; and (c) static behavior.

In another example the load versus deflection behavior may include a non-linear relationship between an amount of force required to compress the composite structure and a deflection of the composite structure.

In another example a stiffness of the composite structure may increase as the composite structure is compressed.

In another example column may have a hole therethrough.

In another example at least one of the column and the hole in the column may have a substantially circular cross-section.

In another example each of the column and the hole in the column may have a substantially circular cross-section.

In another example the column filler may be disposed within the hole in the column.

In another example the elastomer may be selected from the group including (but not limited to): (a) a silicone; (b) a urethane; and (c) a thermoplastic elastomer In another example the composite structure may be attached to at least one of the first member and the second member.

In another example the composite structure may be attached by a mechanism selected from the group including (but not limited to): (a) compressing a portion of the column radially between a compression ferrule fitted in the hole in the column and a first mating surface of one of the first member and the second member, which first mating surface is formed by a hole through one of the first member and the second member; and (b) flaring an end of the column and compressing the flared portion of the column between a capturing component and a second mating surface of one of the first member and the second member.

In another example the column may be inserted through the hole in one of the first member and the second member before the end of the column is flared.

In another example the capturing component may be attached to one of the first member and the second member by a mechanism selected from the group including (but not limited to): (a) a mechanism for threading the capturing component to one of the first member and the second member; (b) a mechanism for adhesively bonding the capturing component to one of the first member and the second member (c) a mechanism for press-fitting the capturing component to one of the first member and the second member; and (d) a mechanism for affixing the capturing component to one of the first member and the second member via at least one threaded fastener.

In another example the column may have a first end and a second end and at least one end of the column may be attached to a flange by a mechanism selected from the group including (but not limited to): (a) fusion welding; (b) chemical bonding; and (c) ultrasonic welding.

In another example the column maybe treated with a material which aids in the attachment to the flange, which treatment may be selected from the group including (but not limited to): (a) impregnating the column with the material; and (b) coating the column with the material.

In another example the flange may be attached to at least one of the first member and the second member by a mechanism selected from the group including (but not limited to): (a) capture behind a press-fit capture ring; (b) threading the flange onto at least one of the first member and the second member; and (c) attaching the flange to at least one of the first member and the second member via at least one threaded fastener.

In another example the column may be impregnated with a material that aids in preventing at least one of (but not limited to): (a) biological ingrowth into the column; and (b) biological attachment to the column.

In another example the column may be coated with a material that aids in preventing at least one of (but not limited to): (a) biological ingrowth into the column; and (b) biological attachment to the column.

In another example the artificial intervertebral disc may be configured to be implanted by at least one method selected from the group including (but not limited to): (a) posterior implantation; and (b) anterior implantation.

In another embodiment an artificial intervertebral disc is provided, comprising: a first anchor member; a second anchor member; and at least two composite structures disposed between the first anchor member and the second anchor member, wherein a first one of the composite structures is comprised of a first column formed of ePTFE and a first column filler formed of an elastomer and a second one of the composite structures is comprised of a second column formed of ePTFE and a second column filler formed of an elastomer.

In one example the first composite structure and the second composite structure may be configured such that the first composite structure and the second composite structure have associated in combination therewith, in at least one axis, a load versus deflection behavior substantially similar to that of a substantially healthy human intervertebral disc.

In another example the load versus deflection behavior may be selected from the group including (but not limited to): (a) dynamic behavior, which dynamic behavior is a function of a time rate application of load; (b) kinematic behavior; and (c) static behavior.

In another example the load versus deflection behavior may include a non-linear relationship between an amount of force required to compress the first composite structure and the second composite structure and a deflection of the first composite structure and the second composite structure.

In another example a stiffness of each of the first composite structure and the second composite structure may increase as each of the first composite structure and the second composite structure is compressed.

In another example the artificial intervertebral disc may be configured to be implanted by at least one method selected from the group including (but not limited to): (a) posterior implantation; and (b) anterior implantation.

In another embodiment an artificial intervertebral disc is provided, comprising: a first anchor member; a second anchor member; and a substantially solid chord of ePTFE disposed between the first anchor member and the second anchor member.

In another embodiment an artificial intervertebral disc is provided, comprising: a first assembly including: (a) a first anchor member; (b) a second anchor member; and (c) a composite structure disposed between the first anchor member of the first assembly and the second anchor member of the first assembly, which composite structure of the first assembly is comprised of a column formed of ePTFE and a column filler formed of an elastomer; and a second assembly including: (a) a first anchor member; (b) a second anchor member; and (c) a composite structure disposed between the first anchor member of the second assembly and the second anchor member of the second assembly, which composite structure of the second assembly is comprised of a column formed of ePTFE and a column filler formed of an elastomer.

In another embodiment the column (e.g., formed of ePTFE) and/or the column filler may contain a compression element (e.g., a spring (e.g., constructed of a biocompatible material, such as titanium)).

Of note, the materials used in constructing the AID assembly may be strong, durable and biocompatible. For example (which example is intended to be illustrative and not restrictive), the anchor plates, ferrules, compression flanges, and/or springs may be constructed of titanium 6AL4V ELI (extra low interstitial), a titanium alloy containing 6% aluminum and 4% vanadium. ePTFE, which may be used to construct the columns, is a biocompatible material. Any additional elastomeric or non-elastomeric materials utilized in the assembly may be biocompatible. One of ordinary skill in the art would readily appreciate the other materials that could be used to construct implants according to the present invention.

In another embodiment the column(s) (e.g., formed of ePTFE) may be coated (e.g., to help prohibit the growth of tissue and/or bone on the column(s), within the interstices of the nodes and/or between the fibrils in the column(s)). In one example (which example is intended to be illustrative and not restrictive), the coating may be silicone, urethane, any desired biocompatible elastomer layer and/or any combination thereof.

In another embodiment the column(s) (e.g., formed of ePTFE) may be impregnated with the filler (e.g., the elastomer).

In another embodiment the device may resist shear translation and flexion of the spine may produce shear at one or more adjacent joints (e.g., a superior adjacent joint).

In another embodiment flexion/extension may produce shear translation and rotation of a superior vertebral body.

In another embodiment each of the first anchor plate and the second anchor plate includes a respective inner vertebra contacting surface for contacting an inner face of a vertebra (the vertebral endplate) and a respective outer vertebrae contacting surface for contacting an outer face of the vertebra (the substantially vertical outer surface on the anterior, posterior, or lateral sides of the vertebra).

In another embodiment the flange may be attached to the anchor by a welded capture ring.

In another embodiment the fastener hole(s) may include feature(s) or mechanism(s) therein for locking the fastener(s) in place, for the purpose of: (a) preventing the fastener from backing out; and/or (b) preventing the angular relation between the axis of the fastener and the axis of the through-hole from changing.

In another embodiment one or more of the anchor member surfaces may be shaped to substantially match adjacent vertebral endplate surfaces to allow for minimal "carpentry" (or bone removal/shaping) during surgery to achieve good contact area (e.g. in cervical spine, the cephalad (towards the head) surface of the implant may be convex in the A-P (anterior-posterior) direction to match the A-P concavity in the vertebral endplate on the caudad (towards the feet) end of the vertebral body cephalad to the disc space and the caudad surface of the implant may be convex laterally to match the lateral concavity in the vertebral endplate on the cephalad end of the vertebral body caudal to the disc space).

In another embodiment one or more pieces of the AID may be sterilized separately, or a final AID unit may be sterilized as a unit. In one specific example (which example is intended to be illustrative and not restrictive), a final AID unit may be placed in a pouch and then sterilized (through the pouch).

Various structural features of the invention, and methods for installing an AID assembly, and for stabilizing the AID assembly, have been described. In this regard, it is believed that when the AID assembly of the present invention is inserted between vertebral bodies and subjected to customary loads, the AID assembly may perform similar to the way in which a healthy intervertebral disc would perform. Of note, the implants of the present invention may provide one or more of the following attributes when inserted in the body (e.g., between vertebrae):

- Essentially the same articulation as a healthy intervertebral disc (e.g., intervertebral lumbar disc, intervertebral cervical disc, intervertebral thoracic disc) may be realized;
- Essentially the same kinematic behavior as a healthy intervertebral disc (e.g., intervertebral lumbar disc, intervertebral cervical disc, intervertebral thoracic disc) may be realized;
- Essentially the same dynamic behavior as a healthy intervertebral disc (e.g., intervertebral lumbar disc, intervertebral cervical disc, intervertebral thoracic disc) may be realized;
- The static properties of the implant and a healthy intervertebral disc (e.g., intervertebral lumbar disc, intervertebral cervical disc, intervertebral thoracic disc) may be substantially identical;
- The implant may be biocompatible;
- The device may be implanted by posterior and/or anterior approaches;
- The device may install in a relatively short period of time (e.g., around 90 minutes);
- The device may exhibit positive results in fatigue tests (e.g., the device may be usable after $10 \times 10^6$ cycles);
- The device may survive static loading, shear loading and testing to induce expulsion;
- The device may fixate relatively rapidly to vertebral bodies;
- The device may minimize contact stress with vertebral bodies at the device interface; and
- The device may be auto-clavable.

In other embodiments the AID assembly may include one or more of the following features:

The device may have lordosis (lordotic angle) built in (in one example the lordotic angle may place the composite structure substantially coincident with the axis of the functional spinal unit ("FSU"))

The anchor plate(s) may have surface treatment(s) to encourage osseointegration (bony ingrowth) to establish ultimate fixation to vertebral endplates. Such surface treatments may include (but not be limited to): electrochemical etch; plasma-sprayed Ti; sintered metallic beads or shards; bioactive/osseoinductive/osseoconductive ceramic coating (e.g., hydroxyapatite (HA))

The device may employ no screws, a single screw or multiple screws for fixation

The device may include features to establish immediate fixation to vertebral endplates. Such features may include (but not be limited to): screw(s); keel(s); serration(s) (e.g., backward-facing serrations or angled bosses to 'bite' into place); sharp protrusion(s); finger(s)/protrusion(s) that can be deployed once device is in place The device may dampen strain energy via compliant composite structure(s)

The columns (e.g., ePTFE column(s)) may be reinforced. Such reinforcement may include (but not be limited to): exterior reinforcement; interior reinforcement; circumferential rib(s)/band(s); spiral ribbing/banding; rib(s)/band(s) of PTFE, nitinol, metal; rib(s)/band(s) disconnected from column; rib(s)/band(s) connected to column; fusion weld; as part of extrusion process A connection between a column and an anchor plate may include a frictional component, for example, due to compressive force capturing column/flange to plate (friction may be enhanced by roughened surface geometry (e.g., on mating anchor plate surface))

A capturing component may be welded to an anchor plate

Holes in an anchor plate may enhance ability of sterilization (e.g., with EtO gas)

The column (e.g., ePTFE column) may be designed such that when the AID assembly is in neutral condition (e.g., not flexed or twisted) the ePTFE is somewhere in the middle of its elongation ratio (not fully compressed or elongated). Further, extreme fibers of ePTFE column may still be within elongation ratio even when device is at extreme limits of angular displacement (e.g., fully flexed, extended, laterally bent, or axially twisted)

The column (e.g., formed of ePTFE) surrounding the column filler may constrain the radial bulge of the column filler during compression, enhancing the molecular stacking of the material, causing the load-deflection response of the composite structure to be non-linear, like a healthy disc The bi-concave core may ride the convex dome surfaces such that the core follows the motion of the 'leading' anchor plate, promoting motion that mimics the shear displacement in an intact disc during bending The AID assembly may have multiple height options to appropriately match the height of disc being replaced and allowing for appropriate distraction to the segment during and after surgery to decompress anatomy, e.g. foraminal nerves (addressing the pathology)

The AID assembly may have multiple sizes (e.g., in the anterior-posterior (A-P) dimension), allowing for proper placement of the composite structure coincident with the axis of the FSU In another embodiment the column of the composite structure (e.g., an ePTFE column) is affixed to the anchor plates to form a structural unit (this is, the column forms a structural "bridging link" between the anchor plates).

In another embodiment the AID assembly is not pre-stressed. Since the AID assembly of this embodiment is not pre-stressed, the column filler (e.g., elastomer) will not exhibit any significant amount of "creep". In addition, the AID assembly of this embodiment will, at times, be under essentially no stress (e.g., when the patient using the AID assembly is lying down). Of note, this is similar behavior to a natural disc. Of further note, when the column is formed of ePTFE, the AID assembly of this embodiment may be capable of operating without being pre-stressed because of the properties of ePTFE.

In another embodiment the ePTFE column may be sintered in tension.

In another embodiment an AID assembly may be constructed by taking ePTFE, fusion welding PTFE to the ePTFE and sintering at the same time (while the ePTFE is held in an elongated position).

In another embodiment the ePTFE may be supplied in an unsintered state and subsequently sintered during the construction of the AID assembly.

In another embodiment the ePTFE may be supplied in a sintered (or partially sintered) state and subsequently sintered again during the construction of the AID assembly.

Of note, when a column is utilized without a column filler (e.g., in the form of an essentially homogeneous structure), such a column may be integrated into the AID assembly (e.g., in terms of attachment to the anchor plates, patient customization) in essentially the same manner as a composite structure discussed herein.

While a number of embodiments of the present invention have been described, it is understood that these embodiments are illustrative only, and not restrictive, and that many modifications may become apparent to those of ordinary skill in the art. For example, one or more components may be constructed of Ti, cobalt chromium, surgical steel and/or any combination thereof. Further, customization may be carried out using multiple, interchangeable components (e.g., interchangeable composite structures). Further still, the customization may be carried out using a family of standard parts. Further still, customization of the AID assembly may be done at the place of manufacture (e.g., by a technician at the factory) and/or at the place of implantation (e.g., by a surgeon at the hospital). Further still, the vertebra contacting side of the anchor members (i.e., the side of the anchor members facing the "upper" and "lower" faces of the vertebrae) may include gripping, tissue ingrowth promoting and/or bone ingrowth promoting elements, such as, for example (which examples are intended to be illustrative and not restrictive), grooves, teeth, protrusions, depressions or any combination thereof. Further still, the mounting tabs associated with the anchor members (which mounting tabs may contact the vertebrae on the generally vertical "outer" faces thereof) may interface with the vertebrae along a planar interface, a curved interface, or a combination thereof. Further still, the mounting tabs may include gripping, tissue ingrowth promoting and/or bone ingrowth promoting elements such as described above. Further still, the column filler (e.g., elastomer) within the column (e.g., ePTFE column) may be of sufficient hardness as to form a distinct "core" within the column (such that the core fills essentially the entire space within the column or the core fills less than the entire space within the column (e.g., having one or more voids above the core, below the core and/or around the core between the core and the column)). Further still, the column filler (e.g., elastomer) within the column (e.g., ePTFE column) may be of insufficient hardness as to form a distinct "core" within the column but may instead fill the column in a more or less "fluid" manner (such that the column filler fills essentially the entire space within the column or the column filler fills less than the entire space within the column (e.g., having one or more voids above the column filler, below the column filler and/or around the column filler between the core and the column). Further still, the filler (e.g., elastomer) may be extruded/injected onto the column(s). Further still, the filler (e.g., elastomer) may protrude out from the top, bottom and/or side(s) of the column. Further still, the protruding filler (e.g., elastomer) may be used to aid in attachment of the composite structure to the anchor plate (e.g., the protruding elastomer may be attached directly or indirectly (via an intermediate element) to an anchor plate using any desired attachment mechanism). Further still, the attachment of the column (s) and/or composite structure(s) to the anchor plates may be carried out using a press fit, a rotary swage, welding (e.g., spot or continuous), a number of discrete interference dings, a forced interference fit, a threaded fit, a punch mechanism at a seam between parts and/or any other desired method (as well, of course, as any combination thereof). Further still, the device may be shaped as desired, such as having a circular shape, an oval shape or a kidney shape, for example (this could be effected by providing a desired shape to any of the components (e.g., the anchor plates and/or the column(s) and/or the composite structure(s))). Further still, the composite structure(s) may essentially fill the space between the anchor plates or there may be empty space between the composite structure(s). Further still, the column filler, the material used to coat the column(s) and/or the material impregnated into the column(s) may be any desired compressible, elastic compressible, extrudable and/or flowable material (or combination thereof). Further still, the load/deflection curves associated with the present invention may result from underlying data having applied thereto any desired type of curve fitting (e.g., polynomial curve fitting to the second or third power).

What is claimed is:

1. An artificial intervertebral disc, comprising:
   a first anchor member;
   a second anchor member, the first and second anchor members having opposing internal surfaces facing one another;
   at least a first dome element with at least one curved face; and
   a composite structure;
   wherein the composite structure is comprised of a column comprising ePTFE and a column filler comprising an elastomer;
   wherein the composite structure is disposed between the opposing internal surfaces of the first anchor member and the second anchor member with the first dome element between at least a portion of the column filler and the internal surface of the first anchor member such that a curved interface exists between the first dome element and the column filler and such that movement of the first anchor member and second anchor member relative to one another causes the first dome element to move relative to the column filler and such that the first dome element has convex curvature that corresponds to a concave curvature of the column filler; and
   wherein the curved interface is spaced apart from the internal surface of the second anchor member.

2. The artificial intervertebral disc of claim 1, further comprising: a second dome element with at least one curved face; wherein the composite structure is disposed between the first anchor member and the second anchor member with the first dome element between at least a portion of the column filler and the first anchor member and with the second dome element between at least a portion of the column filler and the second anchor member such that a curved interface exists between the column filler and each of the first dome element and the second dome element and such that movement of the first anchor member and second anchor member relative to one another causes the first dome element and the second dome element to move relative to the column filler.

3. The artificial intervertebral disc of claim 2, wherein: (a) the interface between the first dome element and the column filler is curved such that the first dome element has a convex surface at the interface and the column filler has a concave surface at the interface; and (b) the interface between the second dome element and the column filler is curved such that the second dome element has a convex surface at the interface and the column filler has a concave surface at the interface.

4. The artificial intervertebral disc of claim 3, wherein the first dome element is formed at least in part from a material selected from the group consisting of PTFE, UHMWPE, a polyethylenet, polished metal, and a high-lubricity, low-wear material and the second dome element is formed at least in part from a material selected from the group consisting of PTFE, UHMWPE, a polyethylene, polished metal, and a high-lubricity, low-wear material.

5. The artificial intervertebral disc of claim 1, wherein the composite structure is configured such that the composite structure has associated therewith, in at least one axis, a load versus deflection behavior similar to that of a healthy human intervertebral disc.

6. The artificial intervertebral disc of claim 5, wherein the load versus deflection behavior is selected from the group consisting of: (a) dynamic behavior, which dynamic behavior is a function of a time rate application of load, (b) kinematic behavior, and (c) static behavior.

7. The artificial intervertebral disc of claim 5, wherein the load versus deflection behavior includes a non-linear relationship between an amount of force required to compress the composite structure and a deflection of the composite structure.

8. The artificial intervertebral disc of claim 7, wherein a stiffness of the composite structure increases as the composite structure is compressed.

9. The artificial intervertebral disc of claim 1, wherein the column has a hole longitudinally therethrough.

10. The artificial intervertebral disc of claim 9, wherein at least one of the column and the hole in the column has a cross-section which is selected from the group consisting of circular, oval, and kidney-shaped.

11. The artificial intervertebral disc of claim 10, wherein at least one of the column and the hole in the column has a circular cross-section.

12. The artificial intervertebral disc of claim 11, wherein the hole in the column has a circular cross-section.

13. The artificial intervertebral disc of claim 12, wherein the column filler is disposed within the hole in the column.

14. The artificial intervertebral disc of claim 13, wherein the column filler is disposed within the hole in the column and the column filler has a cross section corresponding to the cross-section of the hole in the column.

15. The artificial intervertebral disc of claim 1, wherein the elastomer is selected from the group consisting of (a) a silicone, (b) a urethane, (c) a thermoplastic elastomer, (d) an elastomer alloy, and (e) a polyurethane/polycarbonate alloy.

16. The artificial intervertebral disc of claim 1, wherein at least one of the first anchor member and the second anchor member is formed at least in part from a material selected from the group consisting of (a) titanium, (b) cobalt chromium, and (c) surgical stainless steel.

17. The artificial intervertebral disc of claim 1, wherein the column is impregnated with a material that aids in preventing at least one of: (a) biological ingrowth into the column, and (b) biological attachment to the column.

18. The artificial intervertebral disc of claim 1, wherein the column is coated with a material that aids in preventing at least one of: (a) biological ingrowth into the column, and (b) biological attachment to the column.

19. The artificial intervertebral disc of claim 1, wherein each of the first anchor member and the second anchor member includes a respective inner vertebra contacting surface for contacting a vertebral endplate and a respective outer vertebrae contacting surface for contacting a vertical outer surface of the vertebra.

20. The artificial intervertebral disc of claim 19, wherein the inner vertebra contacting surface of at least one of the first anchor member and the second anchor member is curved.

21. The artificial intervertebral disc of claim 20, wherein the inner vertebra contacting surface of each of the first anchor member and the second anchor member is curved.

22. The artificial intervertebral disc of claim 21, wherein the inner vertebra contacting surface of each of the first anchor member and the second anchor member is curved away from one another.

23. The artificial intervertebral disc of claim 22, wherein the inner vertebra contacting surface of each of the first anchor member and the second anchor member is shaped to match adjacent vertebral endplate surfaces to minimize bone removal during implantation.

24. The artificial intervertebral disc of claim 23, wherein the surface of the first anchor member is curved to match the vertebral endplate on the caudad end of the vertebral body cephalad to the disc space; and the surface of the second anchor member is curved to match the lateral concavity in the vertebral endplate on the cephalad end of the vertebral body caudal to the disc space.

25. The artificial intervertebral disc of claim 19, wherein the outer vertebra contacting surface of at least one of the first anchor member and the second anchor member is planar.

26. The artificial intervertebral disc of claim 25, wherein the outer vertebra contacting surface of each of the first anchor member and the second anchor member is planar.

27. The artificial intervertebral disc of claim 19, wherein the outer vertebra contacting surface of at least one of first anchor member and the second anchor member includes a hole therethrough for receiving a fastener.

28. The artificial intervertebral disc of claim 27, wherein the outer vertebra contacting surface of each of the first anchor member and the second anchor member includes a hole therethrough for receiving a fastener.

29. The artificial intervertebral disc of claim 28, wherein at least one of the fastener holes include a mechanism for locking a respective fastener in place, for at least one of the purposes of: (a) preventing the fastener from backing out, and (b) preventing the angular relation between an axis of the fastener and an axis of the hole from changing.

30. The artificial intervertebral disc of claim 28, wherein the configuration of the hole is selected from the group consisting of: (a) normal to the respective outer vertebra contacting surface, and (b) angled relative to the respective outer vertebra contacting surface.

31. The artificial intervertebral disc of claim 1, wherein the artificial intervertebral disc is configured to be implanted by at least one method selected from the group consisting of: (a) posterior implantation, and (b) anterior implantation.

32. The artificial intervertebral disc of claim 1, wherein the artificial intervertebral disc is configured to be implanted in an area of the body selected from the Group consisting of: (a) a lumbar area, (b) a cervical area, and (c) a thoracic area.

33. The artificial intervertebral disc of claim 1, wherein the artificial intervertebral disc is sterilizable by means ethylene oxide gas.

34. The artificial intervertebral disc of claim 33, wherein at least one hole is placed in at least one of the first anchor member and second anchor member to facilitate the ingress of the ethylene oxide sterilization gas.

35. The artificial intervertebral disc of claim 34, wherein a plurality of holes are placed in each of the first anchor member and second anchor member to facilitate the ingress and egress of the ethylene oxide sterilization gas.

36. The artificial intervertebral disc of claim 1, wherein the curved interface spaced apart from the internal surface of the second anchor member defines an apex, the apex being a point on the first dome element that is the shortest distance away from the internal surface of the second anchor member, along the curved interface.

37. An artificial intervertebral disc, comprising:
at least a first anchor member;
at least a second anchor member;
at least a first set of dome elements, the first set of dome elements including an upper dome element and a lower dome element, each of the upper dome element and lower dome element of the first set of dome elements having at least one curved face;
at least a second set of dome elements, the second set of dome elements including an upper dome element and a lower dome element, each of the upper dome element and lower dome element of the second set of dome elements having at least one curved face; and
at least two composite structures;
wherein each composite structure is comprised of a column comprised of ePTFE and a column filler comprised of an elastomer;
wherein a first one of the composite structures is disposed between the first anchor member and the second anchor member with the upper dome element of the first set of dome elements between at least a portion of the column filler of the first one of the composite structures and the first anchor member and the lower dome element of the first set of dome elements between at least a portion of the column filler of the first one of the composite structures and the second anchor member such that a curved interface exists between the upper dome element of the first set of dome elements and the column filler of the first one of the composite structures and a curved interface exists between the lower dome element of the first set of dome elements and the column filler of the first one of the composite structures and such that movement of the first anchor member and second anchor member relative to one another causes the upper dome element of the first set of dome elements and the lower dome element of the first set of dome elements to move relative to the column filler of the first one of the composite structures; and
wherein a second one of the composite structures is disposed between the first anchor member and the second anchor member with the upper dome element of the second set of dome elements between at least a portion of the column filler of the second one of the composite structures and the first anchor member and the lower dome element of the second set of dome elements between at least a portion of the column filler of the second one of the composite structures and the second anchor member such that a curved interface exists between the upper dome element of the second set of dome elements and the column filler of the second one of the composite structures and a curved interface exists between the lower dome element of the second set of dome elements and the column filler of the second one of the composite structures and such that movement of the first anchor member and second anchor member relative to one another causes the upper dome element of the second set of dome elements and the lower dome element of the second set of dome elements to move relative to the column filler of the second one of the composite structures.

38. An artificial intervertebral disc, comprising:
a first anchor member;
a second anchor member, the first and second anchor members having opposing internal surfaces facing one another;
a set of dome elements, the set of dome elements including an upper dome element and a lower dome element, each of the upper dome element and lower dome element of the set of dome elements having at least one curved face; and
a composite structure; wherein the composite structure is comprised of a column comprised of ePTFE and a column filler comprised of an elastomer;
wherein the composite structure is disposed between the opposing internal surfaces of the first anchor member and the second anchor member with the upper dome element of the set of dome elements between at least a portion of the column filler of the composite structure and the internal surfaces of the first anchor member and the lower dome element of the set of dome elements between at least a portion of the column filler of the composite structure and the internal surfaces of the second anchor member such that a curved interface exists between the upper dome element of the set of dome elements and the column filler of the composite structure and a curved interface exists between the lower dome element of the set of dome elements and the column filler of the composite structure and such that movement of the first anchor member and second anchor member relative to one another causes the upper dome element of the set of dome elements and the lower dome element of the set of dome elements to move relative to the column filler of the composite structure;
wherein the curved interface between the upper dome element and the column filler is spaced apart from the internal surface of the second anchor member; and
wherein the curved interface between the lower dome element and the column filler is spaced apart from the internal surface of the first anchor member.

39. The artificial intervertebral disc of claim 38, wherein
the curved interface between the upper dome element and the column filler spaced apart from the internal surface of the second anchor member defines an upper apex, the upper apex being a point on the upper dome element that is the shortest distance away from the internal surface of the second anchor member, along the curved interface between the upper dome element and the column filler and
the curved interface between the lower dome element and the column filler spaced apart from the internal surface of the first anchor member defines a lower apex, the lower apex being a point on the lower dome element that is the shortest distance away from the internal surface of the first anchor member by the shortest distance, along the curved interface between the lower dome element and the column filler.

40. An artificial intervertebral disc, comprising:
a first assembly including: at least a first anchor member;
at least a second anchor member;
at least a first set of dome elements, the first set of dome elements including an upper dome element and a lower dome element, each of the upper dome element and lower dome element of the first set of dome elements having at least one curved face;
at least a second set of dome elements, the second set of dome elements including an upper dome element and a lower dome element, each of the upper dome element and lower dome element of the second set of dome elements having at least one curved face; and
at least two composite structures;
wherein each composite structure is comprised of a column comprised of ePTFE and a column filler comprised of an elastomer;
wherein a first one of the composite structures is disposed between the first anchor member and the second anchor member with the upper dome element of the first set of dome elements between at least a portion of the column filler of the first one of the composite structures and the first anchor member and the lower dome element of the first set of dome elements between at least a portion of the column filler of the first one of the composite structures and the second anchor member such that a curved interface exists between the upper dome element of the first set of dome elements and the column filler of the first one of the composite structures and a curved interface exists between the lower dome element of the first set of dome elements and the column filler of the first one of the composite structures and movement of the first anchor member and second anchor member relative to one another causes the upper dome element of the first set of dome elements and the lower dome element of the first set of dome elements to move relative to the column filler of the first one of the composite structures; and
wherein a second one of the composite structures is disposed between the first anchor member and the second anchor member with the upper dome element of the second set of dome elements between at least a portion of the column filler of the second one of the composite structures and the first anchor member and the lower dome element of the second set of dome elements between at least a portion of the column filler of the second one of the composite structures and the second anchor member such that a curved interface exists between the upper dome element of the second set of dome elements and the column filler of the second one of the composite structures and a curved interface exists between the lower dome element of the second set of dome elements and the column filler of the second one of the composite structures and movement of the first anchor member and second anchor member relative to one another causes the upper dome element of the second set of dome elements and the lower dome element of the second set of dome elements to move relative to the column filler of the second one of the composite structures; and a second assembly including: at least a first anchor member; at least a second anchor member; at least a first set of dome elements, the first set of dome elements including an upper dome element and a lower dome element, each of the upper dome element and lower dome element of the first set of dome elements having at least one curved face; at least a second set of dome elements, the second set of dome elements including an upper dome element and a lower dome element, each of the upper dome element and lower dome element of the second set of dome elements having at least one curved face; and at least two composite structures; wherein each composite structure is comprised of a column comprised of ePTFE and a column filler comprised of an elastomer; wherein a first one of the composite structures is disposed between the first anchor member and the second anchor member with the upper dome element of the first set of dome elements between at least a portion of the column filler of the first one of the composite structures and the first anchor member and the lower dome element of the first set of dome elements between at least a portion of the column filler of the first one of the composite structures and the second anchor member such that a curved interface exists between the upper dome element of the first set of dome elements and the column filler of the first one of the composite structures and a curved interface exists between the lower dome element of the first set of dome elements and the column filler of the first one of the composite structures and movement of the first anchor member and second anchor member relative to one another causes the upper dome element of the first set of dome elements and the lower dome element of the first set of dome elements to move relative to the column filler of the first one of the composite structures; and wherein a second one of the composite structures is disposed between the first anchor member and the second anchor member with the upper dome element of the second set of dome elements between at least a portion of the column filler of the second one of the composite structures and the first anchor member and the lower dome element of the second set of dome elements between at least a portion of the column filler of the second one of the composite structures and the second anchor member such that a curved interface exists between the upper dome element of the second set of dome elements and the column filler of the second one of the composite structures and a curved interface exists between the lower dome element of the second set of dome elements and the column filler of the second one of the composite structures and movement of the first anchor member and second anchor member relative to one another causes the upper dome element of the second set of dome elements and the lower dome element of the second set of dome elements to move relative to the column filler of the second one of the composite structures.

41. An artificial intervertebral disc, comprising:
a first anchor member;
a second anchor member, the first and second anchor members having opposing internal surfaces facing one another;
at least a first dome element with at least one curved face; and
a bridge member;
wherein the bridge member is disposed between the opposing internal surfaces of the first anchor member and the second anchor member with the first dome element between at least a portion of the bridge member and the internal surface of the first anchor member such that a curved interface exists between the first dome element and the bridge member and movement of the first anchor member and second anchor member relative to one another causes the first dome element to move relative to the bridge member;
wherein the curved interface is spaced apart from the internal surface of the second anchor member.

42. The artificial intervertebral disc of claim 41, further comprising: a second dome element with at least one curved face; wherein the bridge member is disposed between the first anchor member and the second anchor member with the first dome element between at least a portion of the bridge member and the first anchor member and with the second dome element between at least a portion of the bridge member and the second anchor member such that a curved interface exists between the bridge member and each of the first dome element and the second dome element and movement of the first anchor member and second anchor member relative to one another causes the first dome element and the second dome element to move relative to the bridge member.

43. The artificial intervertebral disc of claim 42, wherein: (a) the interface between the first dome element and the bridge member is curved such that the first dome element has a convex surface at the interface and the bridge member has a concave surface at the interface; and (b) the interface between the second dome element and the bridge member is curved such that the second dome element has a convex surface at the interface and the bridge member has a concave surface at the interface.

44. The artificial intervertebral disc of claim 41, wherein the curved interface spaced apart from the internal surface of the second anchor member defines an apex, the apex being a point on the first dome element that is the shortest distance away from the internal surface of the second anchor member, along the curved interface.

45. An artificial intervertebral disc, comprising:
at least a first anchor member and a second anchor member, the first and second anchor members having opposing internal surfaces facing one another;
at least a first dome element with at least one curved face;
at least one composite structure; and
at least a first bonding element formed of a material selected from the group consisting of FEP, PFA, and modified PTFE;
wherein the composite structure is comprised of a column formed of ePTFE and a column filler formed of an elastomer;
wherein the composite structure is disposed between the opposing internal surfaces of the first anchor member and the second anchor member with the first dome element between at least a portion of the column filler and the internal surface of the first anchor member such that a curved interface exists between the first dome element and the column filler and movement of the first anchor member and second anchor member relative to one another causes the first dome element to move relative to the column filler;
wherein the curved interface is spaced apart from the internal surface of the second anchor member; and
wherein at least a first portion of the ePTFE column is welded to the first bonding element to form a first bonded assembly at a first end of the ePTFE column; and wherein the first bonded assembly is attached to at least one of the first anchor member and the second anchor member.

46. The artificial intervertebral disc of claim 45, wherein the curved interface spaced apart from the internal surface of the second anchor member defines an apex, the apex being a point on the first dome element that is the shortest distance away from the internal surface of the second anchor member, along the curved interface.

47. An artificial intervertebral disc, comprising:
at least a first anchor member and a second anchor member, the first and second anchor members having opposing internal surfaces facing one another;
at least a first dome element with at least one curved face;
at least one composite structure; and
at least a first bonding element formed of a material selected from the group consisting of FEP, PFA, and modified PTFE;
wherein the composite structure is comprised of a column formed of ePTFE and a column filler formed of an elastomer, wherein the ePTFE column has at least one hole therein;
wherein the composite structure is disposed between the opposing internal surfaces of the first anchor member and the second anchor member with the first dome element between at least a portion of the column filler and the internal surface of the first anchor member such that a curved interface exists between the first dome element and the column filler and movement of the first anchor member and second anchor member relative to one another causes the first dome element to move relative to the column filler;
wherein the curved interface is spaced apart from the internal surface of the second anchor member;
wherein the column filler is disposed in the at least one hole defined in the ePTFE column to form a composite structure, wherein the elastomer extends beyond at least a part of the ePTFE column; and
wherein the composite structure is mounted to at least one of the first anchor member and the second anchor member.

48. The artificial intervertebral disc of claim 47, wherein the curved interface spaced apart from the internal surface of the second anchor member defines an apex, the apex being a point on the first dome element that is the shortest distance away from the internal surface of the second anchor member, along the curved interface.

49. An artificial intervertebral disc, comprising:
at least a first anchor member and a second anchor member, the first and second anchor members having opposing internal surfaces facing one another;
at least a first dome element with at least one curved face;
at least one composite structure; and
at least a first bonding element formed of a material selected from the group consisting of FEP, PFA, and modified PTFE;
wherein the composite structure is comprised of a column formed of ePTFE and a column filler formed of an elastomer, wherein the ePTFE column has at least one hole therein and the hole travels along a path in the ePTFE column including at least one bend;
wherein the composite structure is disposed between the opposing internal surfaces of the first anchor member and the second anchor member with the first dome element between at least a portion of the column filler and the internal surface of the first anchor member such that a curved interface exists between the first dome element and the column filler and movement of the first anchor member and second anchor member relative to one another causes the first dome element to move relative to the column filler;
wherein the curved interface is spaced apart from the internal surface of the second anchor member;
wherein the column filler formed of an elastomer is disposed in the hole in the ePTFE column to form the composite structure, wherein the bend in the path aids in maintaining the elastomer in the hole.

50. The artificial intervertebral disc of claim 49, wherein the curved interface spaced apart from the internal surface of the second anchor member defines an apex, the apex being a point on the first dome element that is the shortest distance away from the internal surface of the second anchor member, along the curved interface.

51. An artificial intervertebral disc, comprising:
a first anchor member;
a second anchor member; and
a bridge member, the bridge member including a column filler disposed therein;
wherein the bridge member is disposed between the first anchor member and the second anchor member; and
wherein the bridge member exhibits a compressive property which mimics a compressive property of a healthy human intervertebral disc, the compressive property being characterized by a non-linear relationship between an amount of force required to compress the bridge member and a deflection of the bridge member.

52. The artificial intervertebral disc of claim 51, wherein the bridge member is formed from one material.

53. The artificial intervertebral disc of claim 51, wherein the bridge member is formed from a plurality of materials.

54. The artificial intervertebral disc of claim 51, wherein the bridge member is attached to at least one of the first anchor member and the second anchor member.

55. The artificial intervertebral disc of claim 51, wherein the bridge member is attached to each of the first anchor member and the second anchor member.

56. The artificial intervertebral disc of claim 51, wherein the compressive property of the bridge member which mimics the compressive property of the healthy human intervertebral disc is defined by a function which is largely parabolic.

57. The artificial intervertebral disc of claim 51, wherein the bridge member is in an unstressed condition when no load is being applied to the bridge member.

58. An artificial intervertebral disc for implantation in a patient via a posterior approach, comprising:
a first assembly including:
a first anchor member;
a second anchor member; and
a bridge member, wherein the bridge member is disposed between the first anchor member of the first assembly and the second anchor member of the first assembly; and
a second assembly including:
a first anchor member;
a second anchor member; and
a second bridge member, wherein the second bridge member is disposed between the first anchor member of the second assembly and the second anchor member of the second assembly;
wherein the bridge member of the first assembly and the bridge member of the second assembly combine to exhibit a compressive property which mimics a compressive property of a healthy human intervertebral disc, the compressive property being characterized by a non-linear relationship between an amount of force required to compress the bridge member and a deflection of the bridge member.

59. The artificial intervertebral disc of claim 58, wherein the bridge member of the first assembly is formed from one material and the bridge member of the second assembly is formed from one material.

60. The artificial intervertebral disc of claim 58, wherein the bridge member of the first assembly is formed from a plurality of materials and the bridge member of the second assembly is formed from plurality of materials.

61. The artificial intervertebral disc of claim 58, wherein the bridge member of the first assembly is attached to at least one of the first anchor member of the first assembly and the second anchor member of the first assembly and the bridge member of the second assembly is attached to at least one of the first anchor member of the second assembly and the second anchor member of the second assembly.

62. The artificial intervertebral disc of claim 58, wherein the bridge member of the first assembly is attached to each of the first anchor member of the first assembly and the second anchor member of the first assembly and the bridge member of the second assembly is attached to each of the first anchor member of the second assembly and the second anchor member of the second assembly.

* * * * *